(12) United States Patent
Honda et al.

(10) Patent No.: US 6,328,692 B1
(45) Date of Patent: Dec. 11, 2001

(54) DEVICE FOR CONTROLLING AN AMOUNT OF LIGHT OF A LIGHTING UNIT FOR AN ENDOSCOPE

(75) Inventors: Ryoji Honda, Yamagata-ken; Makoto Takada; Tadashi Takahashi, both of Tokyo, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/256,229

(22) Filed: Feb. 24, 1999

Related U.S. Application Data

(62) Division of application No. 08/917,083, filed on Aug. 25, 1997, now Pat. No. 5,984,862, which is a division of application No. 08/512,399, filed on Aug. 8, 1995, now abandoned.

(30) Foreign Application Priority Data

| Aug. 8, 1994 | (JP) | 6-185832 |
| Aug. 22, 1994 | (JP) | 6-196362 |
| Aug. 22, 1994 | (JP) | 6-196363 |
| Aug. 22, 1994 | (JP) | 6-196364 |
| Aug. 22, 1994 | (JP) | 6-196365 |
| Aug. 25, 1994 | (JP) | 6-200682 |
| Aug. 29, 1994 | (JP) | 6-203164 |

(51) Int. Cl.[7] ................................................ A61B 1/06
(52) U.S. Cl. ................................. 600/180; 600/178
(58) Field of Search ........................... 600/160, 109, 600/178–180; 348/68, 69, 72; 362/276, 277, 282–284, 322–324

(56) References Cited

FOREIGN PATENT DOCUMENTS 64-31115 * 2/1989 (JP).

* cited by examiner

Primary Examiner—John P. Leubecker
(74) Attorney, Agent, or Firm—Greenblum & Bernstein, P.L.C.

(57) ABSTRACT

A device for controlling an amount of light of a lighting unit for use in an endoscope, used to view an image of an object. The device includes a light shield for shielding light generated by a light source and transmitted to the endoscope. A stepping motor drives the light shield for a series of predetermined time intervals. Brightness of the image is detected during each of the time intervals and pulses are generated during each of the time intervals. A desired brightness of the image is input. The number of pulses generated is determined in accordance with the input desired brightness of the image. The pulses generated are used to drive the stepping motor in each of the plurality of time intervals.

11 Claims, 42 Drawing Sheets

FIG. 6

| INPUT BRIGHTNESS LEVEL - IBL | 1 | 2 | 3 | 4 | 5 | 6 | 7 | 8 | 9 | 10 |
|---|---|---|---|---|---|---|---|---|---|---|
| REFERENCE VALUE - RV | 16 | 24 | 32 | 40 | 51 | 64 | 81 | 102 | 128 | 161 |

FIG. 7

| IRV - BVI | NO. OF OUTPUT PULSES | |
|---|---|---|
| | TABLE 1 | TABLE 2 |
| $01_H$ - $07_H$ | $1_H$ | $1_H$ |
| 08 - 0F | 2 | 2 |
| 10 - 1F | 4 | 3 |
| 20 - 3F | 8 | 4 |
| 40 - 5F | 10 | 6 |
| 60 - 8F | 20 | A |
| 90 - BF | 38 | 10 |
| C0 - FF | 50 | 18 |

FIG. 21

| ANGLE OF ROTATION | 0° | ~ | 15° | ~ | 30° |
|---|---|---|---|---|---|
| COUNT c | 0 | ~ | 60 | ~ | 120 |
| APERTURE SIZE | LARGE | | MEDIUM | | SMALL |

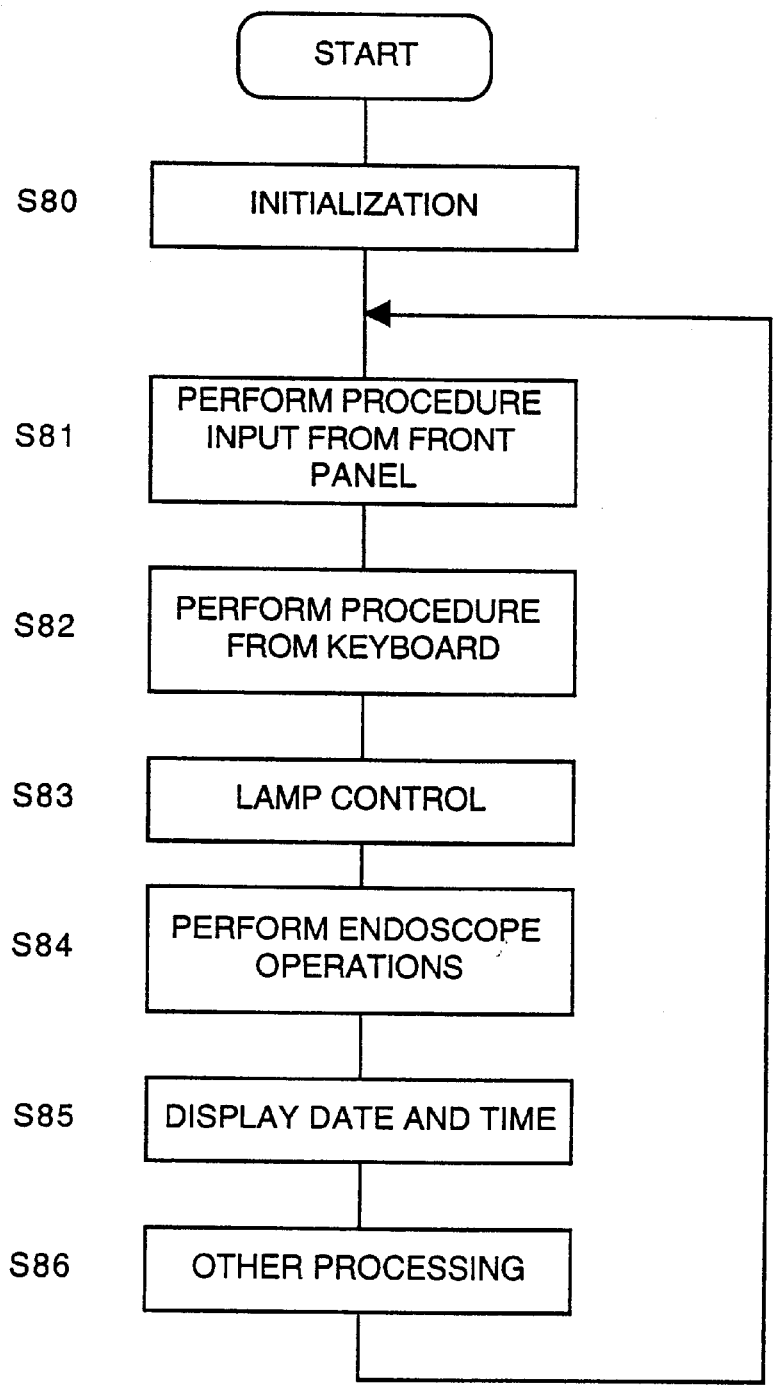

50 msec

ENDOSCOPE USED
FOR DIGESTIVE
SYSTEM 80 msec

ENDOSCOPE NOT
USED FOR
DIGESTIVE SYSTEM

FIG. 27

| BRIGHTNESS VALUE | 0 ~35 | 35 ~70 | 70 ~110 | 110 ~150 | 150 ~ 200 |
|---|---|---|---|---|---|
| CHANGE IN BRIGHTNESS LEVEL Δy | 8 | 7 | 6 | 5 | 4 |
| INPUT BRIGHTNESS LEVEL | 1,2,3 | 4,5,6 | 7,8 | 9 | 10 |

FIG. 30

| ANGLE OF ROTATION θ | 0 ~16 | 16 ~23 | 23 ~28 |
|---|---|---|---|
| CHANGE IN BRIGHTNESS LEVEL Δy | 3 OR 4 | 5 OR 6 | 7 OR 8 |

FIG. 32

| TYPE OF ENDOSCOPE | ANGLE OF ROTATION θ | CHANGE IN BRIGHTNESS LEVEL Δy |
|---|---|---|
| A | 0 ~23 | ≤ 6 |
| A | 23 ~28 | 7, 8 |
| B | 0 ~20 | ≤ 4 |
| B | 20 ~28 | 5 |
| C | 0 ~28 | ≤ 3 |

FIG. 34

| BRIGHTNESS VALUE | 0 ~70 | 70 ~150 | 150 ~ 200 |
|---|---|---|---|
| CHANGE IN BRIGHTNESS LEVEL Δy | ≤ 4 | ≤ 3 | ≤ 2 |
| INPUT BRIGHTNESS LEVEL | 1 ~ 6 | 7 ~ 9 | 10 |

FIG. 37

| ANGLE OF ROTATION θ | 0 ~16 | 16 ~23 | 23 ~28 |
|---|---|---|---|
| CHANGE IN BRIGHTNESS LEVEL Δy | ≤ 2 | ≤ 3 | ≤ 4 |

FIG. 39

| ENDOSCOPE TYPE | ANGLE OF ROTATION θ | CHANGE IN BRIGHTNESS LEVEL Δy |
|---|---|---|
| A | 0 ~23 | ≤ 3 |
|   | 23~28 | ≤ 4 |
| B | 0~20 | ≤ 2 |
|   | 20~28 | ≤ 3 |
| C | 0~28 | ≤ 1.5 |

FIG. 43

PREVIOUS q1

| 1 | 0 | 0 | 1 | 1 | 1 | 0 | 0 |

LSB

SHIFT 1 BIT TO THE LEFT

PRESENT q1

| 1 | 0 | 0 | 1 | 1 | 1 | 0 | 0 | 0 |

LSB

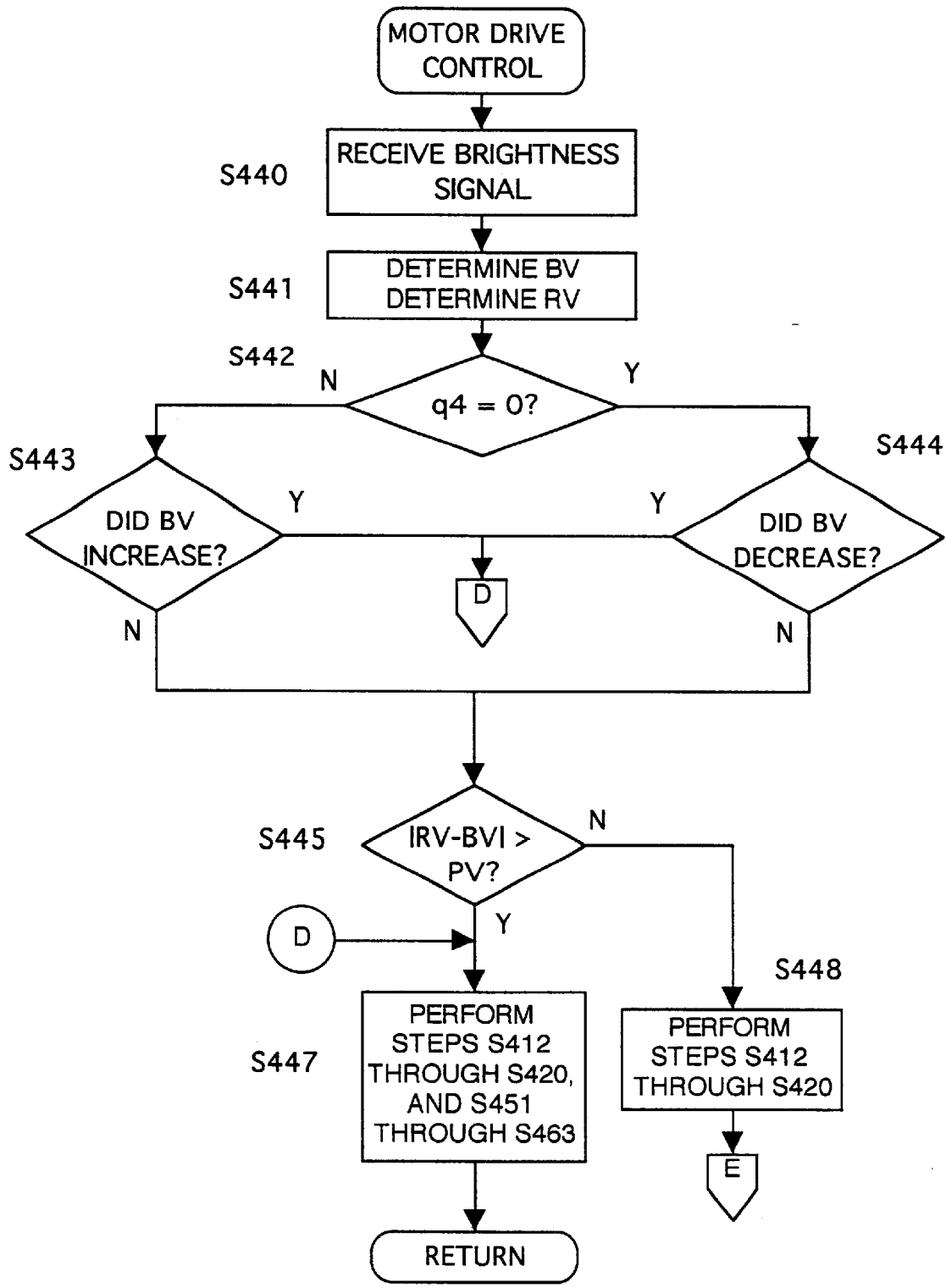

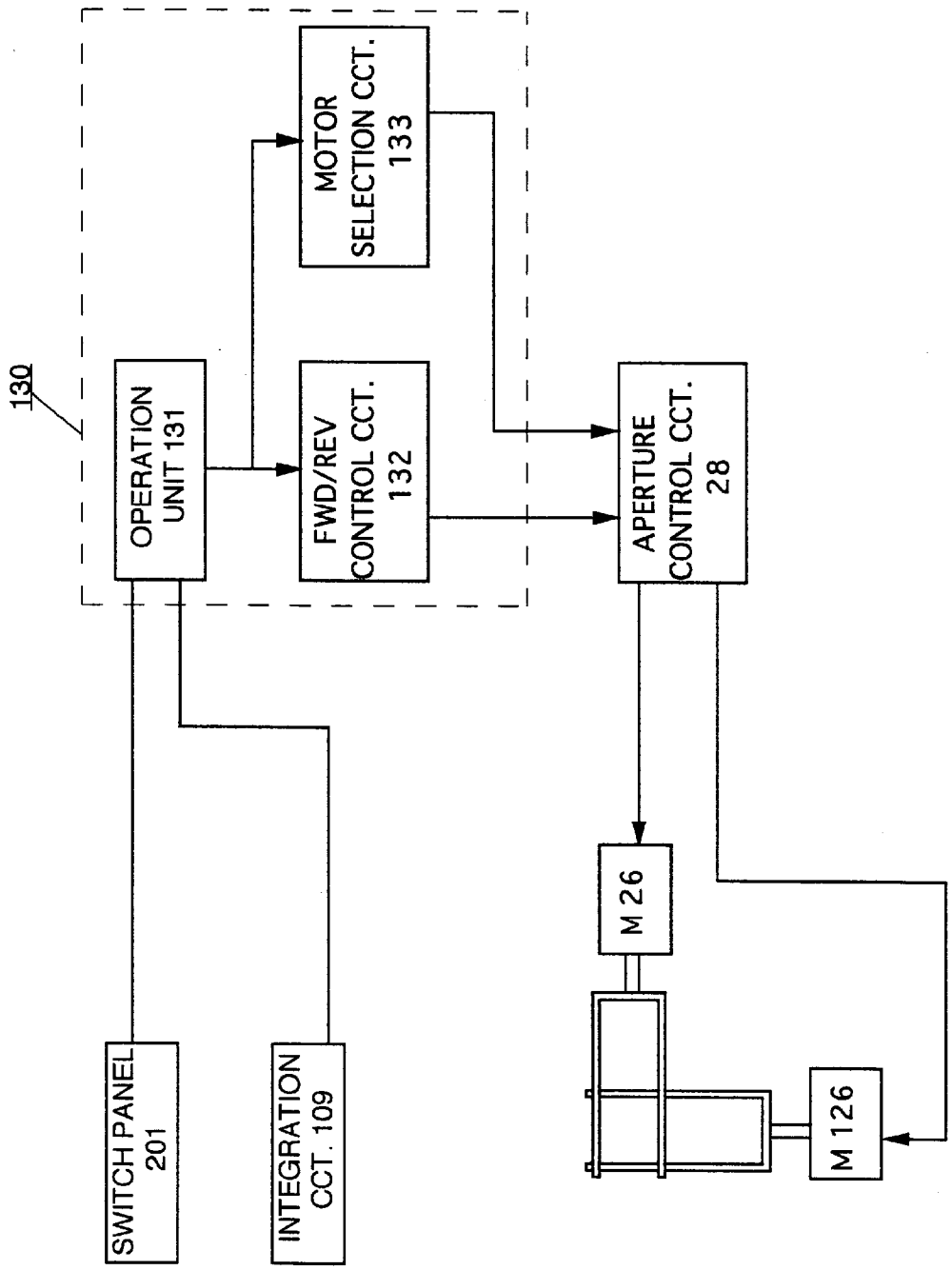

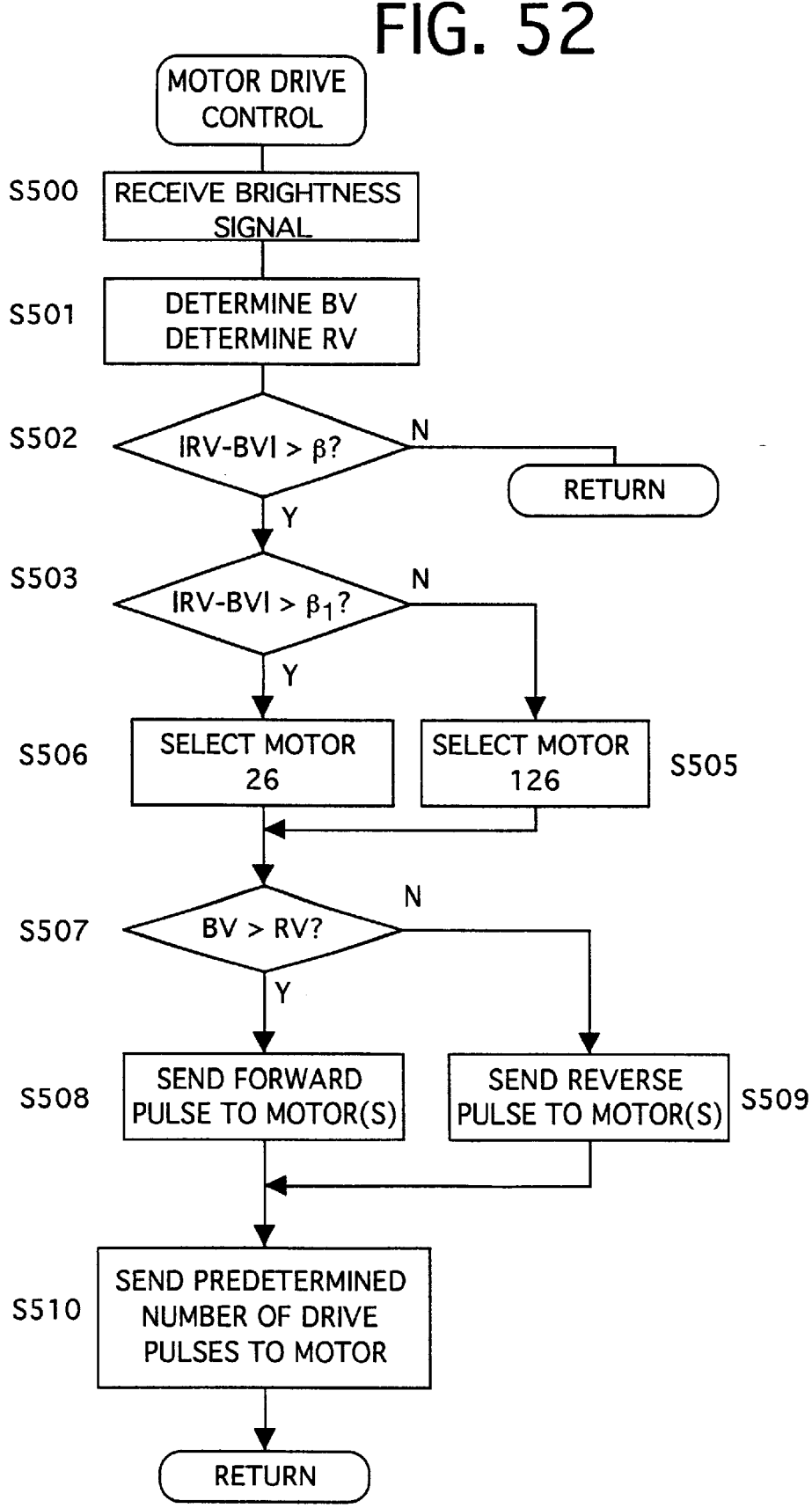

DEVICE FOR CONTROLLING AN AMOUNT OF LIGHT OF A LIGHTING UNIT FOR AN ENDOSCOPE

This application is a Divisional of U.S. application Ser. No. 08/917,083, filed Aug. 25, 1997, now U.S. Pat. No. 5,984,862, which is a Divisional application of U.S. application Ser. No. 08/512,399, filed Aug. 8, 1995, now abandoned, the contents of which are herein incorporated by reference in its entirety.

BACKGROUND OF THE INVENTION

1. Field of the Invention

The present invention is related to a device for controlling an amount of light transmitted from a light source of a video processor which functions as a lighting unit for an endoscope.

2. Background of the Invention

In an endoscope, light is transmitted from a light source using a light wave guide, such as an optical fiber cable, in order to illuminate an object to be observed. In order to adjust the brightness of the observed image, a device for controlling an amount of light transmitted from a light source to an incident surface of the light wave guide, is employed. In a conventional endoscope, the light amount controlling device has a light shield which is rotated about an axis by a stepping motor. The rotation of the light shield controls the amount of light from the light source that is incident on the incident surface of the optical fiber cable. With this type of light amount controlling device, the brightness of the observed image is detected periodically. Then, the position of the light shield is adjusted such that the brightness of the observed image is within an allowed brightness range.

Conventionally, the amount of light transmitted from the light source to the endoscope is controlled by applying the same number of pulses to the input of the stepping motor during each interrupt procedure (see FIG. 11A). Therefore, the stepping motor and the light shield are rotated by the same angular amount during each interrupt procedure. The process of detecting the brightness level, and driving the stepping motor to rotate the light shield is repeated until the detected brightness is again within the allowed brightness range.

However, in the conventional endoscope, since the number of driving pulses sent to the motor is constant during the execution of each interrupt procedure, if the number of pulses is set to a relatively small value, then the light shield will be moved slowly. This results in an increase in the response time of the light amount controlling device.

As shown in FIG. 11A, for example, each drive pulse rotates the motor 0.5 degrees, three drive pulses are sent during each interrupt. The interrupts are executed every 50 ms. Thus, in order to rotate the stepping motor 10 degrees, seven interruption procedures are required for a total time of 0.35 seconds. Further, since the number of pulses must be in multiples of three, the number of drive pulses cannot be 20, the optimum number, but must be 18 or 21. Therefore, the light shield cannot be moved to the optimum position.

In order to decrease the response time of the light amount controlling device, the number of driving pulses sent to the stepping motor can be increased. However, in this case, the light shield will be moved through a large angle of rotation and thus it may not be possible to adjust the amount of light such that the brightness level falls within the allowed brightness range. This will result in the control system becoming unstable with unwanted back-and-forth oscillations (hereinafter referred to as hunting) occurring.

Further, as different types of endoscopes have different allowed brightness ranges, different numbers of driving pulses are required in order to properly adjust the amount of light transmitted from the light source.

Furthermore, for one type of endoscope, if the sending of a predetermined number of pulses to the stepping motor does not cause hunting, in another endoscope, the predetermined number of pulses may not be sufficiently low, and hunting may occur. Therefore, since the light source may be connected with various types of endoscopes, the number of pulses may be set to the minimum number required for all types of endoscopes in order to avoid the hunting problem. As a result, the speed at which the brightness level can be adjusted for the types of endoscopes is reduced.

SUMMARY OF THE INVENTION

It is therefore an object of the present invention to provide a device for controlling the amount of light produced by a lighting unit for use in an endoscope, in which the amount of light can be adjusted quickly and accurately without causing hunting.

According to one aspect of the present invention, there is provided a device for controlling an amount of light of a lighting unit for use in an endoscope, the endoscope being used to view an image of an object. The device includes a mechanism for shielding light generated by a light source and transmitted to the endoscope. A stepping motor drives the light shielding means for a plurality of predetermined time intervals. A mechanism detects a brightness of the image during each of the predetermined time intervals. Pulses are generated during each of the predetermined time intervals. The number of the pulses generated control an amount of driving of the stepping motor in each of the plurality of predetermined time intervals. The number of pulses generated by the pulse generating mechanism is determined in accordance with a difference between the brightness of the image detected during each of the predetermined time intervals and a desired brightness of the image.

Therefore, a different number of pulses is generated when the difference in brightness of the detected image and the desired brightness changes. Preferably, when the brightness difference is large, a large number of pulses is generated, and therefore the light shielding means is moved quickly. Then when the brightness difference is small, and the detected brightness if almost within an allowed brightness range, the number of pulses generated is small. Therefore, the light shielding means is moved in smaller steps and hunting can be prevented.

In a preferred embodiment, a memory stores a first table of numbers of pulses to be generated corresponding to a plurality of brightness ranges. Each of the brightness ranges are a range of differences between the detected brightness of the image and the desired brightness of the image. The memory can be a ROM or other static memory. Further, there is a unique number of pulses stored for each brightness range. Therefore, depending on the difference in brightness between the detected image and an input brightness level set by an operator, the number of pulses sent to the stepping motor will be different.

Since many types of endoscopes may be used with the lighting unit, the memory of the preferred embodiment stores a second table of numbers of pulses to be generated which correspond to the plurality of brightness ranges. The second table of numbers of pulses is different from the first table of numbers of pulses, and corresponds to another type of endoscope.

Further, the device includes a selector for selecting one of the first and second tables.

In another preferred embodiment, the endoscope has a memory for storing the type of the endoscope. The selector selects either the first or second table in response to the type of the endoscope stored in the memory.

This allows for easy selectability of the endoscope and facilitates operation of the device when used with the respective endoscope. Furthermore, the device is optimized for each endoscope that is attached thereto.

In another preferred embodiment, the selector is manually actuable for selecting the type of endoscope.

According to a second aspect of the present invention, there is provided a device for controlling a device for controlling an amount of light of a lighting unit for an endoscope, the endoscope being used to view an image of an object. The device includes a mechanism for shielding light generated by a light source and transmitted to the endoscope. A stepping motor drives the light shielding mechanism by a predetermined driving amount for a plurality of time intervals. A mechanism sets a duration of the time interval to have one of a plurality of time values.

Therefore, by changing the time interval for driving the light shielding means, the time required for adjusting the amount of light can be reduced, even if the amount of driving of the stepping motor is made small to prevent hunting.

In a preferred embodiment, the endoscope type is stored in a memory and the duration of the time interval is set in accordance with the type of the endoscope. Therefore, the operation of the device can be optimized for each type of endoscope.

In another preferred embodiment, the time interval is set in accordance with the position of a manually operable switch. This adds flexibility to the operation of the device, and allows operation to be optimized for endoscopes that do not have the type stored in memory.

According to a third aspect of the present invention, there is provided a device for controlling an amount of light of a lighting unit for use in an endoscope, the endoscope being used to view an image of an object. The device includes a mechanism for shielding light generated by a light source and transmitted to the endoscope. A stepping motor drives the light shielding mechanism for a plurality of predetermined time intervals. A mechanism detects a brightness of the image during each of the predetermined time intervals. A predetermined number of pulses is generated during each of the predetermined time intervals, the predetermined number of pulses being transmitted to the stepping motor during each of the predetermined time intervals. An angular position of the light shielding means is determined. A phase of excitation of the stepping motor is varied in response to the determined angular position.

Therefore, by changing the number of phases of excitation of the stepping motor, the drive amount of the stepping motor in a given predetermined time interval can be changed.

In a preferred embodiment, the stepping motor is driven with 2 phase excitation when the angular position is less than or equal to a predetermined angular position. Otherwise, the stepping motor is driven with 1–2 phase excitation (i.e., excitation alternating between single phase and two phase excitation at every pulse).

In another preferred embodiment, the phase of excitation of the stepping motor is further varied in response to the detected brightness of the image. In this case, even if the angular position is greater than the predetermined angular position, if the brightness of the image is larger than a predetermined value, the stepping motor is driven with 2 phase excitation to improve the speed at which the amount of light is reduced. This brings the detected image brightness into an allowed brightness range.

In another preferred embodiment, the phase of excitation of the stepping motor is varied in response to the endoscope type. This optimizes the performance of the device for each type of endoscope.

According to a fourth aspect of the present invention, there is provided a device for controlling an amount of light of a lighting unit for use in an endoscope, the endoscope being used to view an image of an object. The device includes a mechanism for shielding light generated by a light source and transmitted to the endoscope. A stepping motor drives the light shielding mechanism for a plurality of predetermined time intervals. A mechanism detects a brightness of the image during each of the predetermined time intervals. A mechanism inputs one of a plurality of desired brightness of the image. A predetermined number of pulses is generated during each of the predetermined time intervals, the predetermined number of pulses being transmitted to the stepping motor. One of a plurality of allowed brightness ranges of the image is set in accordance with the input desired brightness of the image. Then, the device determines whether the detected brightness is within the set allowed brightness range.

Therefore, in a preferred embodiment, when the desired input brightness of the image is high, the allowed brightness range is large. Since the change in brightness of the image per unit rotation of the light shielding mechanism is therefore small, the number of time intervals required to adjust the amount of light such that the detected image brightness is within the allowed brightness range is reduced.

In another preferred embodiment, an angular position of the light shielding mechanism is determined, and the allowed brightness range is set in response to the determined angular position of the light shielding mechanism.

In yet another preferred embodiment, the type of endoscope is determined and the allowed brightness range is also set in response to the determined endoscope type.

According to a fifth aspect of the present invention, there is provided a device for controlling an amount of light of a lighting unit for use in an endoscope, the endoscope being used to view an image of an object. The device includes a mechanism for shielding light generated by a light source and transmitted to the endoscope. A stepping motor drives the light shielding mechanism for a plurality of predetermined time intervals. A mechanism detects a brightness of the image during each of the predetermined time intervals. A mechanism inputs a desired brightness of the image. Pulses are generated during each of the predetermined time intervals; a number of the pulses generated are used to drive the stepping motor in each of the plurality of predetermined time intervals. The number of pulses generated by the pulse generator is determined in accordance with the input desired brightness of the image.

Therefore, since the change in brightness per unit rotation of the light shielding means increases as the brightness of the image decreases when the input brightness level is high, the light shielding mechanism can have a higher driving amount than when the brightness of the image is low. This will improve the speed at which the amount of light can be adjusted, without introducing a hunting problem.

Alternatively, the number of pulses generated can be determined in accordance with an angular position of the light shielding mechanism.

Optionally, the number of pulses generated can be further determined in accordance with the type of endoscope.

According to a sixth aspect of the present invention, there is provided a device for controlling an amount of light of a lighting unit for use in an endoscope, the endoscope being used to view an image of an object. The device includes a mechanism for shielding light generated by a light source and transmitted to the endoscope. A stepping motor drives the light shielding mechanism for a plurality of predetermined time intervals. A mechanism detects a brightness of the image during each of the predetermined time intervals. A mechanism detects hunting of the stepping motor. Pulses are generated during each of the predetermined time intervals, a number of the pulses generated being used to drive the stepping motor in each of the plurality of predetermined time intervals. A number of pulses generated by the pulse generator during each of the predetermined time intervals is determined in response to hunting being detected by the hunting detector, the determined number of pulses being reduced when the hunting is detected.

Therefore, if hunting is detected, by reducing the number of pulses sent to the stepping motor, the driving amount of the stepping motor is reduced, and the hunting problem can be overcome.

Optionally, the device determines whether the brightness of the image is larger than a desired brightness of the image. A first value is output if the detected brightness is larger than the desired brightness, and a second value if the detected brightness if not larger than the desired brightness. Each output value is stored in a register of a memory. The device then determines if hunting occurred by examining the registers of the memory. If the registers sequentially store both the first and second values, then hunting has occurred.

By using a memory to store the information, detection of hunting can be performed quickly, since the response time of the stepping motor does not effect the detection of hunting.

Alternatively, data relating to a direction (i.e., forward and reverse) of the stepping motor can be stored in a register of another memory. If the registers sequentially store both the forward and reverse data, then hunting has occurred.

According to a seventh aspect of the present invention, there is provided a device for controlling an amount of light of a lighting unit for use in an endoscope, the endoscope being used to view an image of an object. The device includes a plurality of light shields for shielding light generated by a light source and transmitted to the endoscope. A stepping motor drives the plurality light shields for a plurality of predetermined time intervals. A mechanism detects a brightness of the image during each of the predetermined time intervals. A predetermined number of pulses is generated during each of the predetermined time intervals. The pulses are used to control an amount of driving of the stepping motor in each of the plurality of predetermined time intervals. A difference between the brightness of the image detected and a desired brightness of the image determines which of the plurality of light shields is to be driven by the stepping motor.

Therefore, if the difference in brightness is large, two or more light shields may be moved, thereby increasing the speed at which the amount of light is varied. Conversely, if the difference in brightness is small, then only one light shield is moved to bring the detected image brightness into an allowed brightness range. Since the number of light shields driven can be changed at each time interval, the amount of light can initially be varied quickly, and then varied accurately in order to prevent hunting.

Alternatively, light shields having different effects on the change in brightness per degree of rotation can be employed. In this case, the light shields which has the greatest effect on the change in brightness per degree of rotation is driven in order to quickly change the detected image brightness. Then another light shield having less effect can be driven in order to change the detected image brightness more accurately, until the detected image brightness is in the allowed brightness range.

In the preferred embodiments, the light shields rotate on different axis of rotation.

BRIEF DESCRIPTION OF THE DRAWINGS

FIG. 6 shows a table of input brightness level values and corresponding reference values stored in a ROM of the microprocessor shown in FIG. 5;

FIG. 7 shows a table, stored in the ROM of the microprocessor shown in FIG. 5, showing a number of driving pulses output to a stepping motor of the light amount controlling device shown in FIG. 1, for different brightness ranges;

FIG. 8 shows a flowchart of a main program stored in the ROM of the microprocessor, shown in FIG. 5;

FIG. 21 shows a table, stored in the ROM of the microprocessor shown in FIG. 5, showing a relationship between a counter, an angle of rotation of the stepping motor, and a brightness of the lighting unit, according to the fourth embodiment of the present invention;

FIG. 27 is a table showing a relationship between a change in brightness of an object, and an angle of rotation of the stepping motor, corresponding to a graph A shown in FIG. 25;

FIG. 30 is a table showing a relationship between an angle of rotation of the stepping motor and a change in brightness level, according to a first modification of the fifth embodiment of the present invention;

FIG. 32 is a table showing the relationship between an angle of rotation of the stepping motor and a change in brightness of the lighting unit, for different types of endoscopes, according to a second modification of the fifth embodiment of the present invention;

FIG. 34 is a table showing a relationship between a change in brightness of an object, and an angle of rotation of the stepping motor, according to a sixth embodiment of the present invention;

FIG. 37 is a table showing a relationship between an angle of rotation of the stepping motor and a change in brightness level, according to a first modification of the sixth embodiment of the present invention;

FIG. 39 is a table showing the relationship between an angle of rotation of the stepping motor and a change in brightness of the lighting unit, for different types of endoscopes, according to a second modification of the sixth embodiment of the present invention;

FIG. 43 illustrates two registers used for storing data, employed in the seventh embodiment of the present invention;

FIGS. 46A and 46B show a flowchart of an interrupt procedure used to control a driving of the stepping motor of the light amount controlling device, according to a modification of the eighth embodiment of the present invention;

FIG. 49 shows a schematic diagram of a microprocessor used in the video processor shown in FIG. 47;

FIG. 52 shows a flowchart of an interrupt procedure used to control a driving of the stepping motor of the light amount controlling device, according to the modification of the ninth embodiment of the present invention.

DESCRIPTION OF THE EMBODIMENTS

Figure 1:
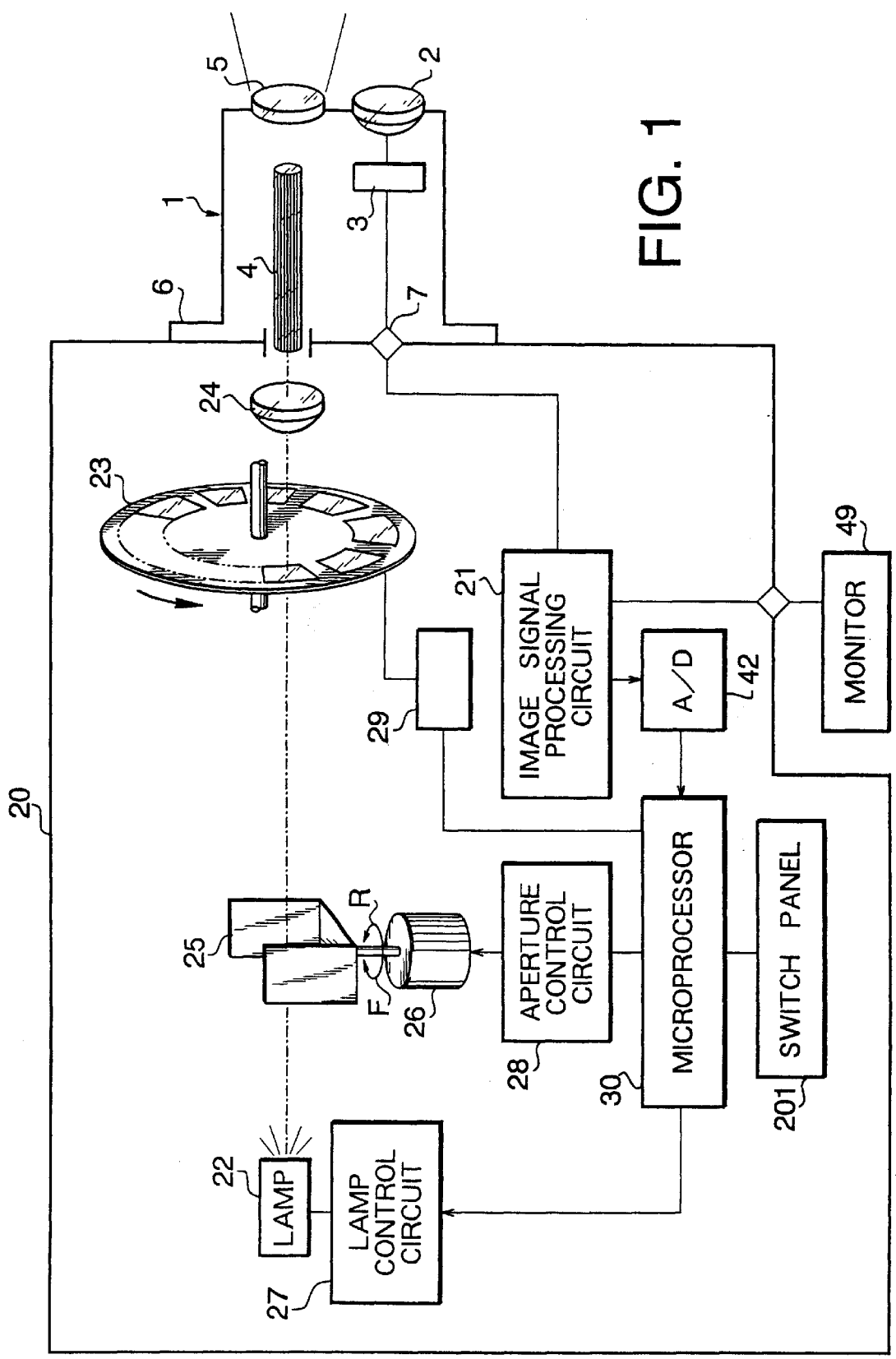
FIG. 1 shows a schematic diagram of an endoscope and video processor which functions as a lighting unit for the endoscope, employing a light amount controlling device of the present invention.

FIG. 1 shows a structure of an endoscope 1 attached to a video processor 20. The video processor 20 functions as a lighting unit for the endoscope 1. The endoscope 1 includes an objective lens 2 and an image receiving element 3, such as a CCD (Charge Coupled Device). Further, light from a lamp 22 of the video processor is directed by a light wave guide 4 (such as an optical fiber cable), and a lens 5, to be incident on an object that is to be viewed using the endoscope 1. The lens 5 increases the angular dispersion of the light emitted by the light wave guide 4.

A connector 6 of the endoscope 1 is detachably connected to video processor 1 20. The connector 6 includes an electronic connector 7, which electrically connects the image receiving element 3 to the video processor 20.

The video processor 20 includes an image signal processing circuit 21, the lamp 22, a lamp control circuit 27, a converging lens 24, a light shield 25, a motor 26, a motor control circuit 28, an A/D converter 42 and a microprocessor 30.

A switch panel 201 is provided with (1) an auto/manual switch for switching a control mode of the brightness of the observed screen between a manual mode and an automatic mode, and (2) an up/down switch for increasing/decreasing the brightness level of the observed screen over a range of 10 levels.

The image signal processing unit 21 receives an image signal from the image receiving element 3, processes the image signal and outputs a video signal to a monitor 49. Further, a brightness signal corresponding to the received image signal is transmitted to an A/D converter 42, and converted to a digital signal and sent to the microprocessor 30.

The lamp 22, which is controlled by the light source control circuit 27, emits light towards the light wave guide 4. The brightness level of the light emitted by the lamp 22 is modified in accordance with the position of the light shield plate 25 relative to the lamp 22. The light is then converged by the converging lens 24 and is incident on an RGB filter 23.

The light shield 25 is rotated about an axis by the motor 26. The rotation of the light shield 25 changes the cross-sectional area of the light flux that is transmitted from the lamp 22 to the converging lens 24. The motor 26 is a stepping motor, and is controlled by the motor control circuit 28.

The RGB filter 23 is disk shaped and rotates about an axis. The RGB filter 23 has red (R) filters, green (G) filters and blue (B) filters arranged sequentially around the disk. The rotation of the RGB filter 23 is controlled by the filter driving circuit 29.

The microprocessor 30 controls the operation of the video processor 20 and the endoscope 1.

Figure 2:
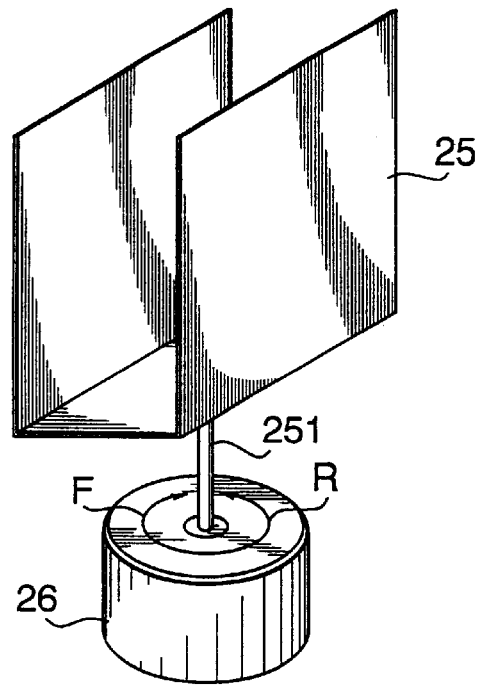
FIG. 2 is a perspective view of a light shield used in the light amount controlling device shown in FIG. 1.

FIG. 2 is a perspective view of the light shield 25 and the stepping motor 26. The light shield 25 is a thin plate having a U-shape. The bottom surface of the U-shaped plate is secured to a spindle 251 of the stepping motor 26. The axis of the spindle 251 is perpendicular to the optical axis of a light path L (see FIG. 3).

Figure 3:
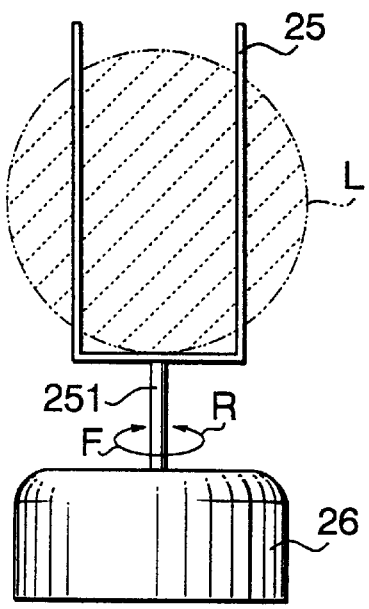
FIG. 3 is a side view of the light shield shown in FIG. 2.

FIG. 3 is a side view of the light shield 25 and the stepping motor 26 as viewed along the optical axis. As shown in FIG. 3, when the vertical surfaces of the light shield 25 are parallel to the optical axis, the light path L of the light is hardly shaded by the light shield 25.

By rotating the light shield 25, the amount of light transmitted from the lamp 22 to the converging lens 24 is changed.

Figure 4:
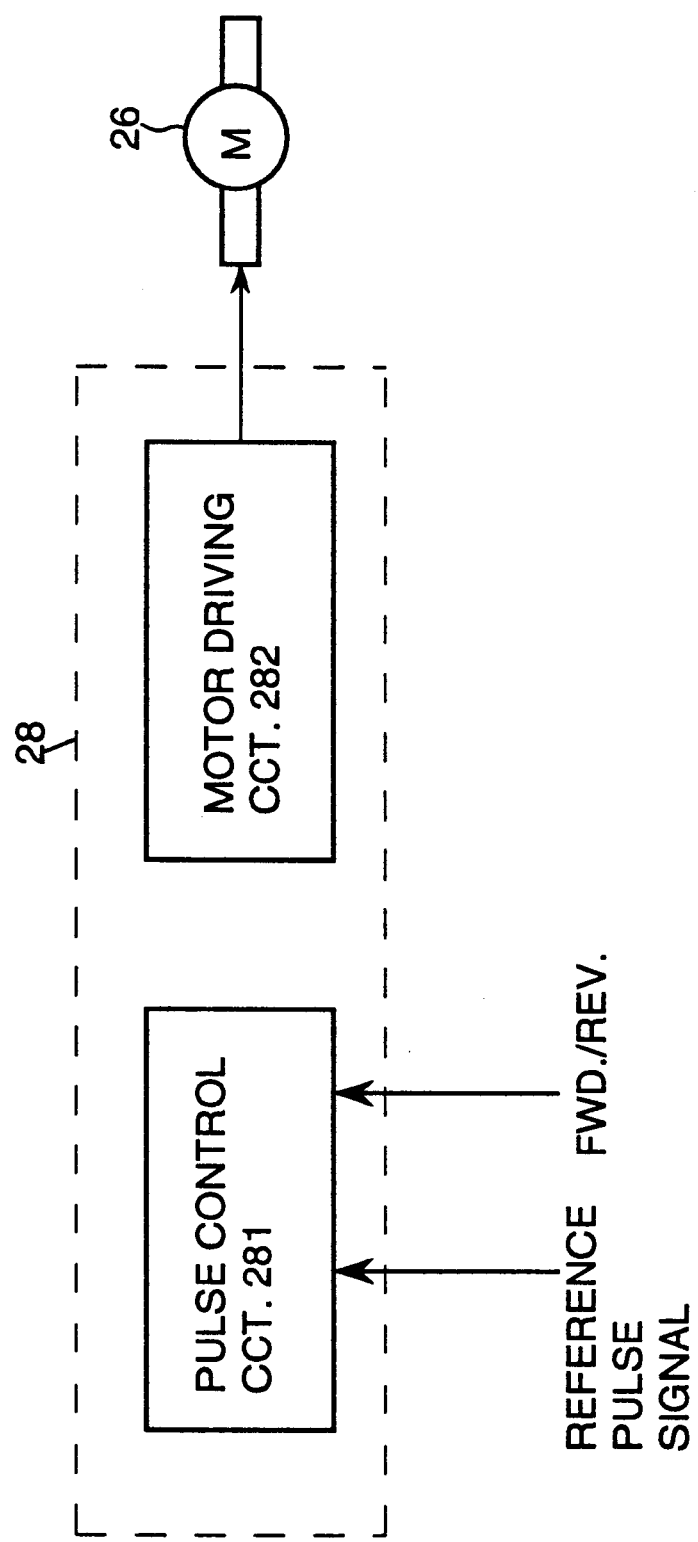
FIG. 4 shows a block diagram of a motor control circuit of the light amount controlling device shown in FIG. 1.

FIG. 4 shows a block diagram of the motor control circuit 28. The motor control circuit 28 includes a pulse control circuit 281 and a motor control circuit 282.

The pulse control circuit 281 receives a direction signal indicating a direction in which the stepping motor 26 is rotated, and a reference pulse signal. The reference pulse signal is modified and sent to the motor 26 from the CPU 30 through an I/O port 41. A phase switching signal determines whether a 2-phase excitation or 1–2 phase excitation method is used, when driving the stepping motor 26.

The direction signal indicates the direction that the stepping motor 26 is to be rotated. A forward direction signal results in the stepping motor 26 being rotated in a forward direction. The light shield 25 is also rotated in the forward direction, thereby reducing the amount of light emitted by the lighting unit along the light path L.

Conversely, a reverse signal results in the stepping motor 26 being rotated in a reverse direction. The light shield 25 is also rotated in the reverse direction, thereby increasing the amount of light emitted by the lighting unit along the light path L. In response to the received instruction signal, the motor driving circuit 282 outputs driving pulses according to a predetermined excitation method for driving the stepping motor 26 synchronously with the driving pulse signal transmitted from the pulse control circuit 281.

Figure 5:
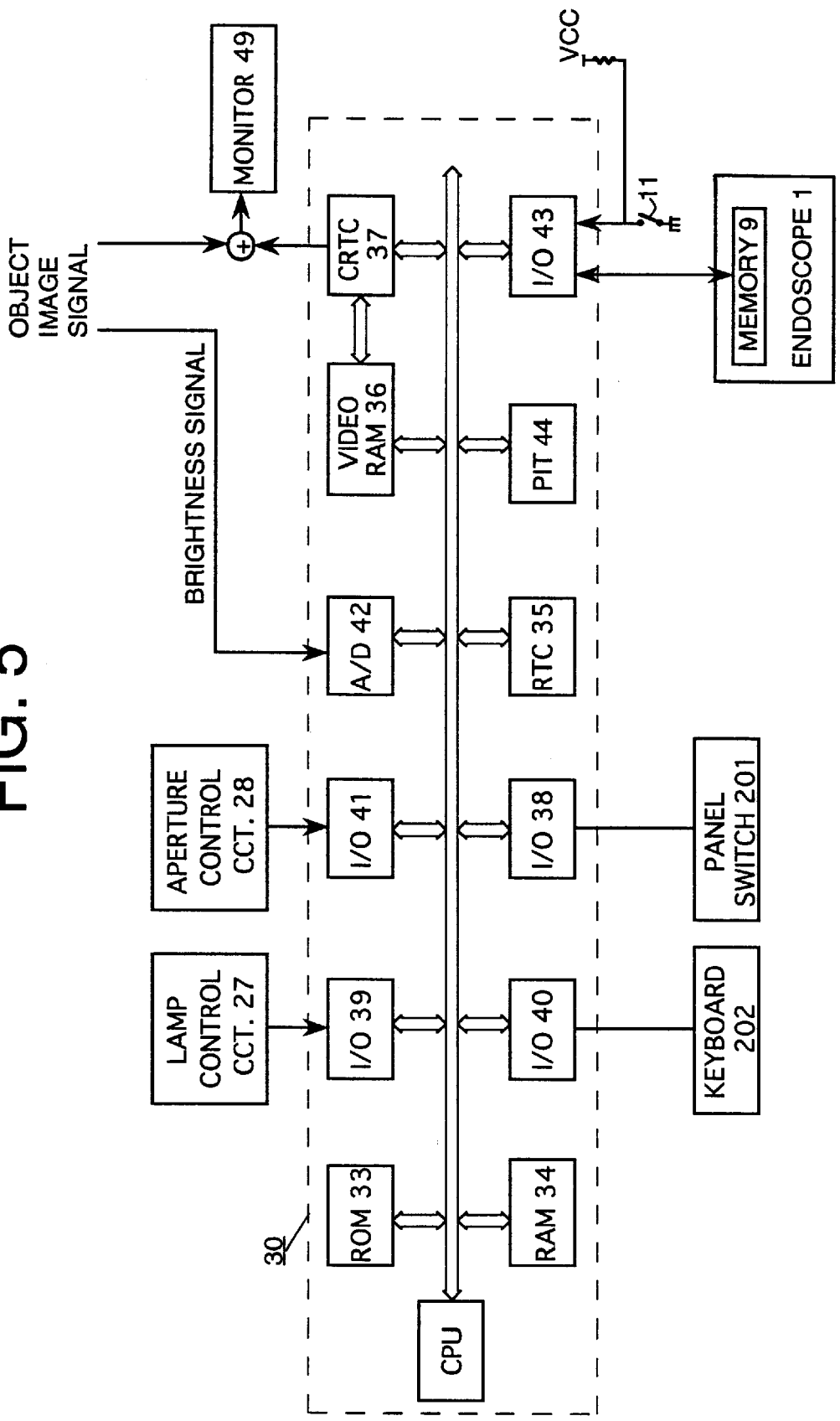
FIG. 5 shows a schematic diagram of a microprocessor used in the video processor shown in FIG. 1.

FIG. 5 shows a configuration of the microprocessor 30. The microprocessor 30 includes a CPU (Central Processing Unit) 31 and a system bus 32. A ROM (Read Only Memory) 33 stores programs to be executed, a RAM (Random Access Memory) 34, an RTC (Real Time Clock) 35, etc. are connected to the system bus 32.

Character data stored in a VRAM (Video Random Access Memory) 36 is transmitted to a CRTC (Cathode Ray Tube Microprocessor) 37, combined with the image data output by the image processing circuit 21, and viewed on the monitor 49.

The switch panel 201 of the video processor 20, an external keyboard 202 and the lamp control circuit 27, for controlling the lamp 22 are also connected to the system bus 32 through the I/O ports 38, 39 and 40, respectively.

The motor control circuit 28 receives/transmits signals through the I/O port 41. A brightness signal indicating the brightness of the observed screen which is output by the image signal processing circuit 21 is converted from an analog signal to a 256-step digital signal by an analog-digital converter 42, and then transmitted to the microprocessor 30.

By connecting the connector 6 with the video processor 20, a memory 9 provided inside the endoscope 1 is connected to the microprocessor 30 through an I/O port 43. The memory 9 stores data intrinsic to the endoscope 1, such as data which indicates the endoscope type.

A DIP switch 11 is connected with the I/O port 43. By turning the DIP switch 11 on or off, the input impedance of the I/O port 43 is toggled between a high or low level.

A programmable interval timer PIT 44 which can be programmed with different time intervals, is connected to the system bus, for providing the timing interval of the interrupt routine. A counter output terminal of the PIT 44 sends an interrupt to the CPU 31 at the programmed time intervals.

FIG. 6 shows a table of the input brightness levels IBL and reference values stored in the ROM 33. A brightness level of one through ten is selected by using the switch panel 201. The brightness level is the level of the brightness of the image of object observed on the monitor 49. The microprocessor 30 then sets a reference value corresponding to the brightness level. The reference values corresponding to the brightness levels are stored in the ROM 33.

The microprocessor 30 then compares the brightness signal output by the image signal processing circuit 21 and converted by the A/D converter 42 with the reference value. If necessary, microprocessor 30 controls the motor control circuit 28 to drive the stepping motor 26, thereby rotating the light shield 25, to change the amount of light emitted by the lighting unit of the endoscope.

FIG. 7 shows a table of the number of driving pulses output to the stepping motor 26 for a given brightness difference, according to a first embodiment of the present invention. The given brightness difference is defined as the absolute value of the difference between the digital brightness signal and the reference values stored in the ROM 33. The ROM 33 also stores eight values of the number of driving pulses, corresponding to the brightness difference, in two ROM tables (i.e., ROM table 1 and ROM table 2).

When the brightness difference is small, the number of driving pulses stored in both ROM tables is small. As the brightness difference increases, the number of driving pulses stored in both ROM tables becomes larger. However, for large brightness differences, the values of the number of driving pulses stored in ROM table 1 are larger than the corresponding number of driving pulses stored in ROM table 2.

FIG. 8 shows a flowchart of a main program stored in the ROM 33, according to the first embodiment of the present invention.

A predetermined initialization routine is executed in step S80. Then, steps S81 and S82 execute a procedure set by the switch panel 201 and a keyboard input, respectively. A procedure for controlling an operation of the lamp controlling circuit 27 is then executed in step S83.

Step S84 executes a normal operation of the endoscope 1, while step S85 executes a procedure for displaying the date and time. Other procedures are executed in step S86. The process then repeats.

In the first embodiment, information transmitted from the memory 9 of the endoscope 1 to the I/O port 43 is used for determining which one of the ROM tables 1 or 2 is used.

When the endoscope 1 is connected to the video processor 20, during the procedure of step S84, the endoscope type is read out of the memory 9. The information is substituted for a predetermined variable and stored in the RAM 34.

Stepping Motor Driven Using a Lookup Table

Figure 9:
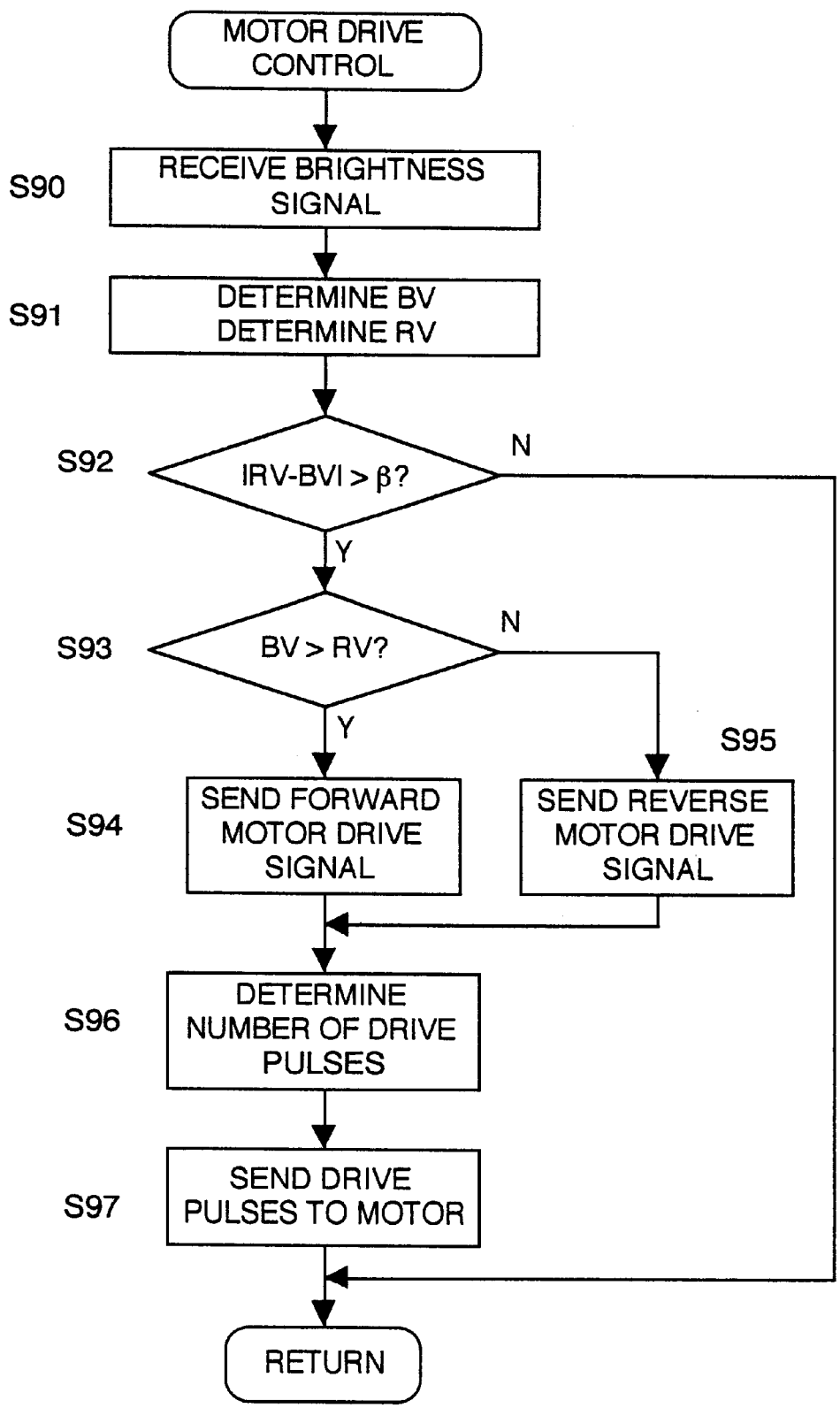
FIG. 9 shows a flowchart of an interrupt procedure used to control a driving of the stepping motor of the light amount controlling device, according to a first embodiment of the present invention.

FIG. 9 shows a flowchart illustrating the drive control of the stepping motor 26 according to the first embodiment of the present invention. The drive control of the stepping motor 26 is an interruption procedure executed at predetermined intervals. In this first embodiment, the predetermined interval is 0.05 seconds (i.e., 50 ms).

Initially in step S90, the brightness signal is transmitted from the image signal processing circuit 21. The brightness signal is then converted to a brightness value BV, in step S91. Also in step S91, an input brightness level IBL, which is set by an operator of the endoscope 1, is used to generate a reference brightness value, RV. Step S92 then compares the reference value RV with the brightness value BV to determine whether the brightness value BV is within an allowed brightness range β (i.e., step S92 determines whether |RV−BV|>β).

If the brightness value BV of the observed image is within the allowed range (S92:N) with respect to the input brightness level IBL, the interruption procedure is terminated and control returns to the main program.

If the difference between the brightness value BV and the reference value RV exceeds the allowed range (S92:Y), then step S93 determines whether the brightness value BV is greater than the reference value RV. If the brightness value BV is greater than the reference value RV (S93:Y), a forward rotation signal is sent to the motor control circuit 28 in step S94. This results in the light shield 25 being rotated such that the amount of light emitted by the lighting unit is made smaller.

Conversely, if the brightness value BV is smaller than the reference value RV (S93:N), a reverse rotation signal is sent to the motor control circuit 28 in step S95. This results in the light shield 25 being rotated such that the amount of light emitted by the lighting unit is made larger.

Step S96 determines the number of drive pulses to be sent to the motor during the interrupt routine. The number of pulses is determined in accordance with the difference between the brightness of the image signal processed by the image signal processing circuit 21, and the reference value. The number of pulses which corresponds to the difference on brightness is then read out from one of the ROM tables 1 or 2. Further, the use of ROM table 1 or 2 is determined by the type of endoscope being used, as explained in more detail below.

Then, in step S97, the number of drive pulses determined in step S96 is sent to the stepping motor 26, and the interruption procedure is terminated.

Figure 10A:
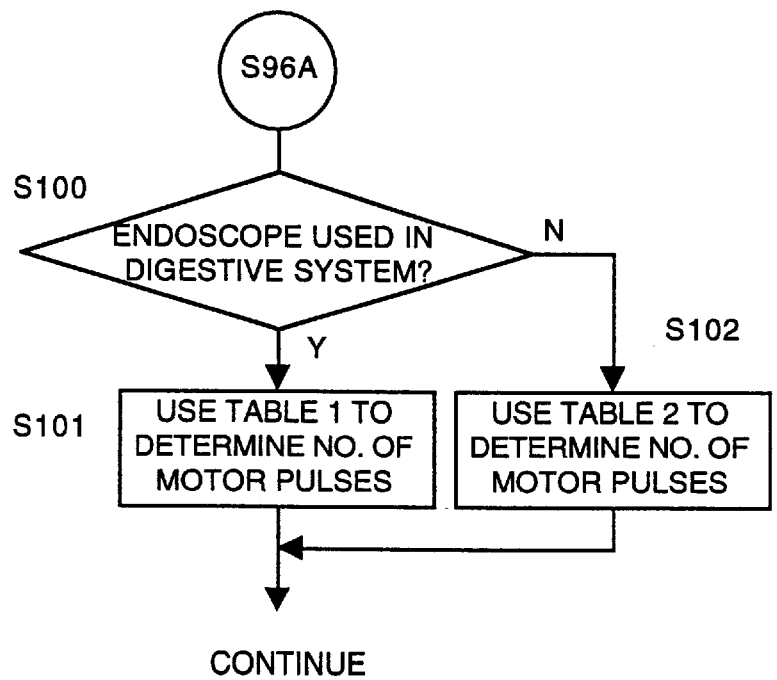
FIG. 10A shows a flowchart of a process for determining a number of pulses to send to the stepping motor, according to the first embodiment of the present invention.

FIG. 10A shows the process carried out in step S96, in order to determine the number of drive pulses to be sent to the pulse control circuit 281, according to the first embodiment.

Step S100 determines whether the type of endoscope 1 connected to the video processor 20, is used in the digestive system. The data corresponding to the endoscope type is stored in the memory 9 of the endoscope 1.

If the type of endoscope corresponds to one used for the digestive system (S100:Y), then ROM table 1 is used for determining the number of pulses for driving the stepping motor 26, in step S101. If the type of endoscope is for a system (i.e., such as the respiratory system) other than the digestive system (S100:N), then ROM table 2 is used for determining the number of pulses for driving the stepping motor 26, in step S102. Then control proceeds to step S97.

As described above, if the difference between the brightness value BV and the reference value RV is relatively large, a greater number of pulses are applied to the stepping motor 26, and therefore the light shield 25 rotates at a high speed during one interrupt procedure. When the difference between the brightness signal value and the reference value is relatively small, a smaller number of pulses are applied to the stepping motor 26. In the latter case, since the light shield 25 is rotated by a small amount during one interrupt procedure, the light shield 25 can be easily positioned at the optimum location.

Further, the number of pulses sent to the stepping motor 26 is different depending on the type of endoscope being used. Therefore, the control of the stepping motor 26 can be optimized for each type of endoscope.

Figure 10B:
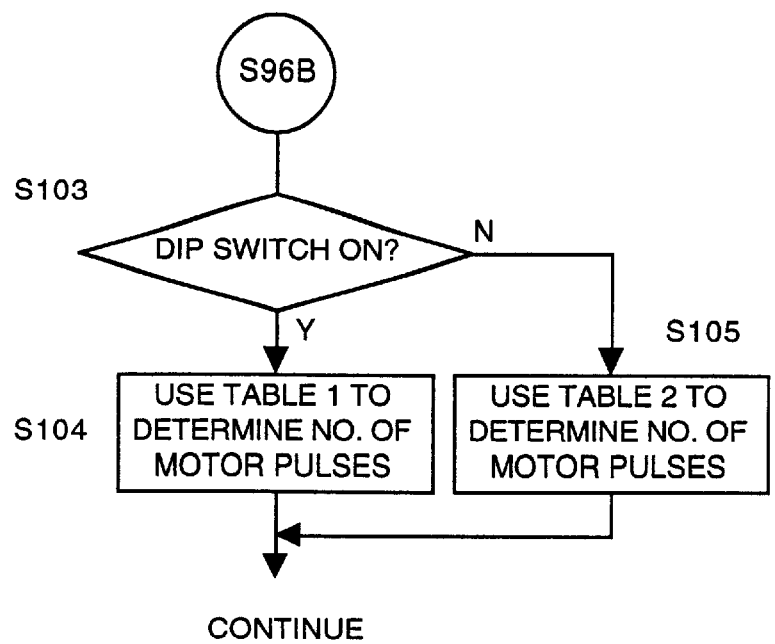
FIG. 10B shows a flowchart of a process carried out to determine a number of pulses to send to the stepping motor, according to a modification of the first embodiment of the present invention.

FIG. 10B shows the process carried out in step S96, in order to determine the number of drive pulses to be sent to the stepping motor 26, according to a modification of the first embodiment.

In modification of the first embodiment, the type of endoscope is determined in accordance with a position of the DIP switch 11. By setting the DIP switch 11 to one of two positions, the type of endoscope may be set.

Therefore, step S103, which is similar to step S100, determines whether the type of endoscope 1 connected to the video processor 20 is used in the digestive system.

If the type of endoscope corresponds to one used for the digestive system (S103:Y), then ROM table 1 is used for determining the number of pulses for driving the stepping motor 26, in step S104. If the type of endoscope is for a system (i.e., such as the respiratory system) other than the digestive system (S103:N), then ROM table 2 is used for determining the number of pulses for driving the stepping motor 26, in step S105. Then control proceeds to step S97.

Therefore, by employing a simple circuit, the type of endoscope may be easily selected by an operator. Further, since the type of endoscope can be selected, the control of the stepping motor 26 can be optimized for each type of endoscope, as explained above.

Figure 11A:
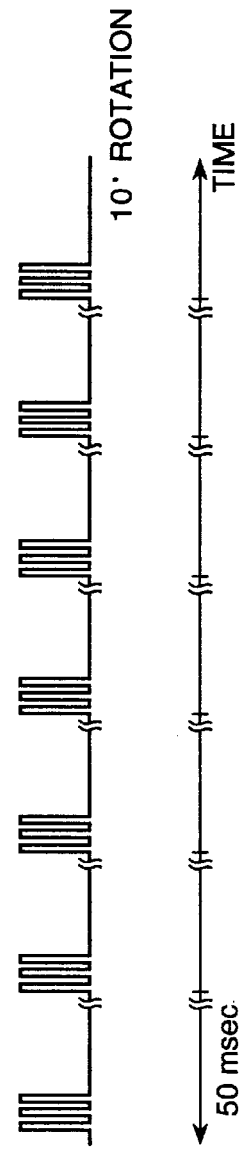
FIG. 11A shows a timing diagram of the drive control of the stepping motor of the prior art.
Figure 11B:
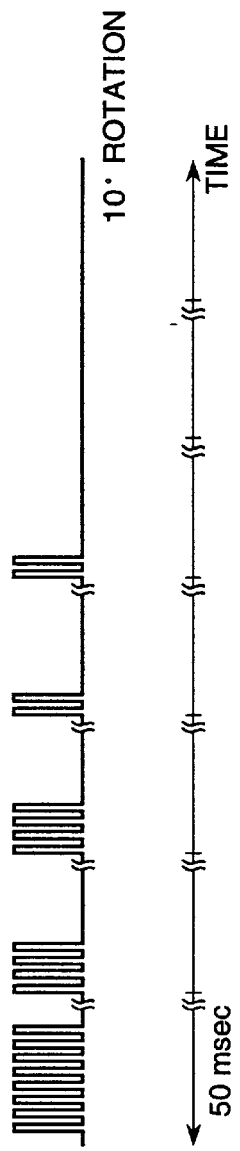
FIG. 11B shows a timing diagram of the drive control of the stepping motor, according to the first embodiment of the present invention.

FIG. 11B is a timing chart showing the drive control of the stepping motor 26, according to the first embodiment. The chart shows an example when the stepping motor 26 is rotated 10 degrees. In this example, it is assumed that the stepping motor 26 rotates 0.5 degrees for every drive pulse. According to the first embodiment, as shown in FIG. 11B, the number of pulses at every interruption procedure changes (i.e., 8, 4, 4, 2 and 2). As shown in FIG. 11B, only five interruption procedure are required, for a total time of 0.25 seconds. Furthermore, the light shield 25 is positioned at the optimum position, since the number of driving pulses is not limited to a multiple of three.

As described above, the stepping motor 26 is driven during five interrupt procedures. The number of pulses sent to the stepping motor 26 during each interrupt is determined from the ROM table 1 or 2. However, by programming another ROM table having different numbers of pulses corresponding to the range of brightness differences, all 20 pulses could have been sent to the motor during the first interrupt procedure. The number of pulses sent to the stepping motor 26 is only limited by the period of pulse and the interval between successive interrupts.

If the type of endoscope used is for the digestive system, the objective area is relatively wide and the object distance fluctuates. In this case, by using ROM table 1, the endoscope quickly responds to the change in the object distance. If the type of endoscope used is not for the digestive system, then the observing area is fairly narrow with a stable object distance. In this case, by using ROM table 2, the brightness can be precisely adjusted.

As described above, by adjusting the number of pulses sent to the stepping motor 26 in accordance with a difference between the brightness value BV and the reference brightness value RV, the amount of light emitted by the lighting unit can be changed quickly, thereby improving the response time of the endoscope. Further, since the number of steps can be reduced when the detected brightness is only slightly out of the allowed brightness range, the precision of control of the light amount is increased without reducing the response time of the endoscope. Furthermore, the stability of the control of the light amount is improved, and hunting is prevented.

In the first embodiment described above, two types of endoscopes are categorized (i.e., those used for the digestive system, and all other endoscopes). However, it is possible to have more than two categories of endoscopes, in which case, more than two ROM tables of stored numbers of driving pulses would be required.

Adjustable Intervals Between Successive Interrupts

Figure 12:
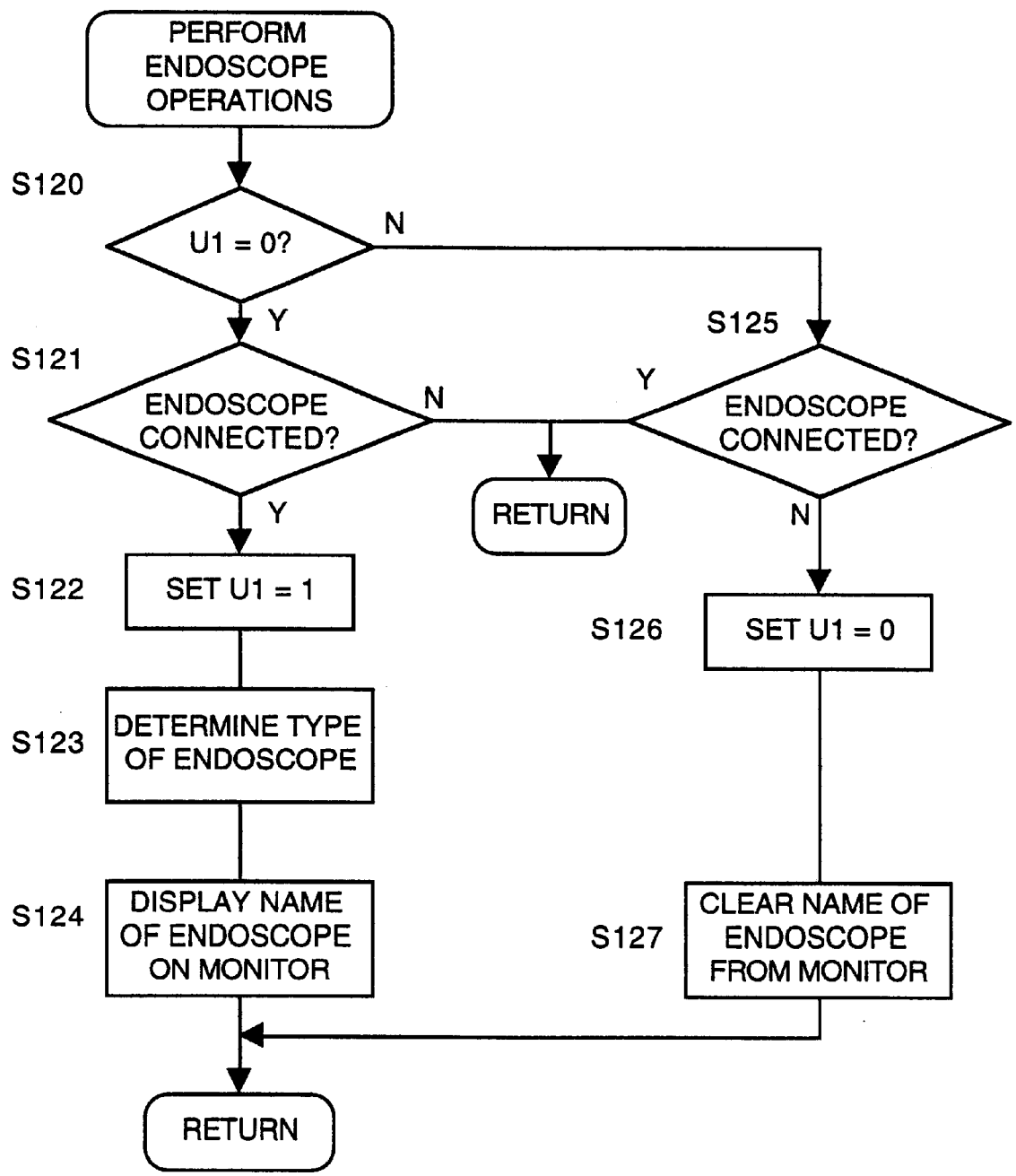
FIGS. 12 and 13 show flowcharts of a subroutine for performing endoscope operations, called from the main program shown in FIG. 8, according to a second embodiment of the present invention.
Figure 13:
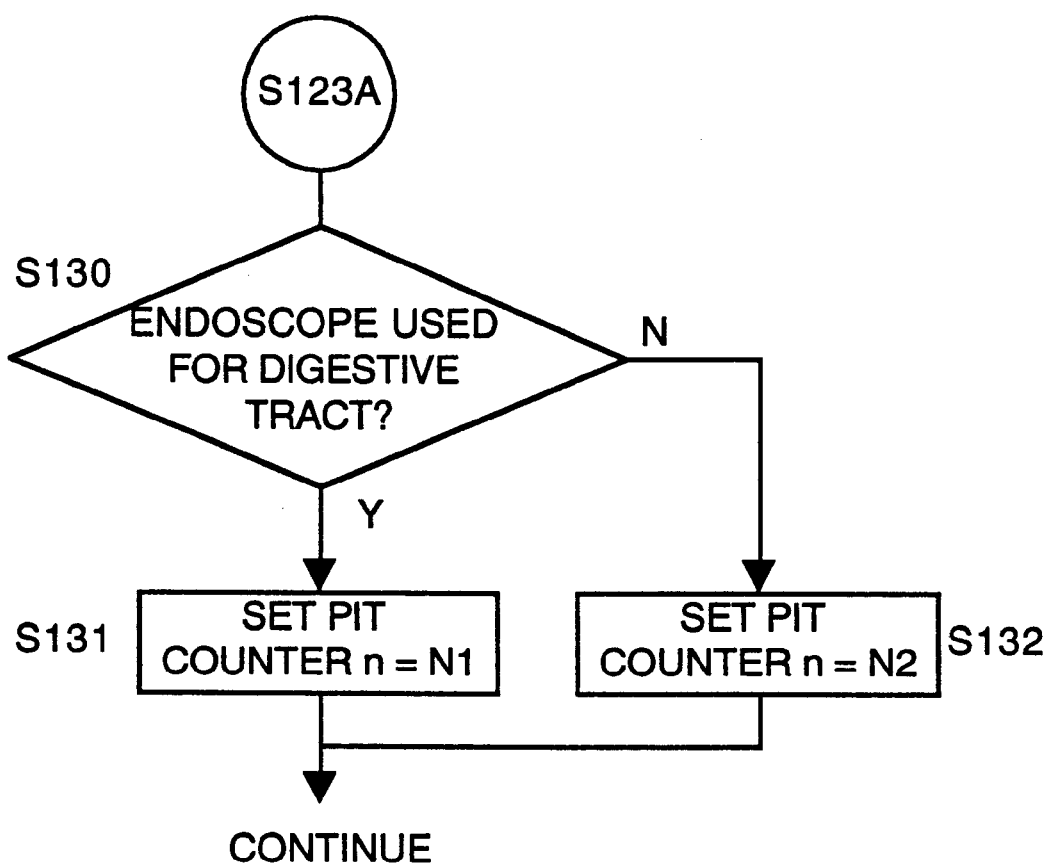

FIG. 8 also illustrates a flowchart of a main program according to a second embodiment of the present invention. FIGS. 12 and 13 illustrate a flowchart of a subroutine of the endoscope operations called from step S84 of the main program shown in FIG. 8.

In the second embodiment, the PIT 44 is programmed with one of two different interval timing values depending on the type of endoscope 1 that is connected to video processor 20. Further, a flag U1 is set equal to 1 when the endoscope 1 is connected to the video processor 20, and is set equal to 0 when the endoscope 1 is not connected to the video processor 20.

Step S120 determines whether the endoscope 1 is currently connected to the video processor 20, by examining the setting of the flag U1. The setting of the flag U1 is changed when the change in the physical connection of the endoscope 1 to the video processor 20, is detected. If U1 is equal to 0 (S120:Y), then the endoscope 1 is not currently connected to the video processor. Step S121 then monitors the connection status of the endoscope 1 to the video processor 20. If the endoscope 1 is not connected to the video processor 20 (S121:N), then the routine ends and control returns to the main program.

If the endoscope 1 is connected to the video processor 20 (S121:Y), then U1 is set equal to 1 step S122. Step S123 then determines the type of endoscope 1 connected to the video processor 20. The process carried out in this step is shown in FIG. 13, and will be described in more detail later. Then, the name of the endoscope type is displayed on the monitor 49, in step S126, and the routine ends.

In step S120, if the endoscope 1 was currently connected to the video processor 20 (S120:N) then step S127 monitors the connection status of endoscope 1 to the video processor 20. If the endoscope 1 remains connected to the video processor 20 (S125:Y), then the routine ends and control returns to the main program.

If the endoscope 1 is disconnected from the video processor 20 (S125:N), then U1 is set to 0 in step S126, and the name of the type of endoscope is cleared from the display on the monitor 49, in step S127. The routine then ends and control returns to the main program.

FIG. 13 shows the process carried out in step S123 in more detail.

Step S130 determines whether the endoscope 1 is the type used for the digestive system. In the second embodiment, the type of endoscope can be determined using data stored in the memory 9, or by a setting of the DIP switch 11.

If the endoscope 1 is the type used for the digestive system (S130:Y) then the PIT counter 44 has a count value n set equal to N1 in step S131. Otherwise, when the endoscope 1 is a different type of endoscope (S130:N), the count value n is set equal to N2 in step S132.

As described above, the interrupt time interval can be programmed in the PIT 44 to have one of two values, depending on the type of endoscope connected to the video processor 20. In the second embodiment, the two time interval values are 50 ms and 90 ms. Further, the number of pulses used to drive the stepping motor 26 is the same for each type of endoscope.

The interrupt routine used to control the drive of the stepping motor 26 in the second embodiment is similar to the drive control of the stepping motor 26 in the first embodiment, described above and shown in FIG. 9. However, in step S96, the number of pulses to drive the stepping motor is a fixed value.

Figure 14A:
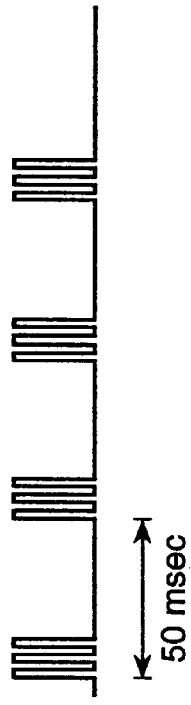
FIGS. 14A and 14B show timing diagrams of the drive control of the stepping motor, according to the second embodiment of the present invention.
Figure 14B:
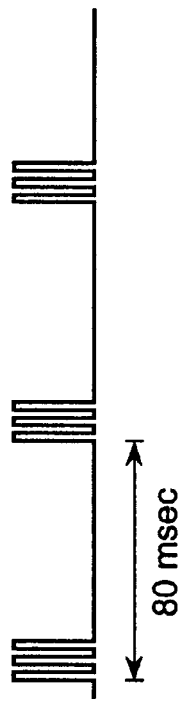

FIGS. 14A and 14B show timing diagrams of the drive control of the stepping motor 26 for an endoscope used for the digestive system, and another type of endoscope, such as an endoscope used for the respiratory system, respectively.

When using the endoscope for the digestive system, since the area to be observed in the digestive system is relatively wide and the object distance varies frequently, in the interruption time interval is set to 50 ms. Therefore, the light shield 25 can be moved quickly in response to a change in the object distance.

When using the endoscope for a different system, such as the respiratory system, since the area to be observed is small and the object distance is stable, the interruption time interval is set to 80 ms. Therefore, the light shield 25 can be moved with greater accuracy.

Figure 15:
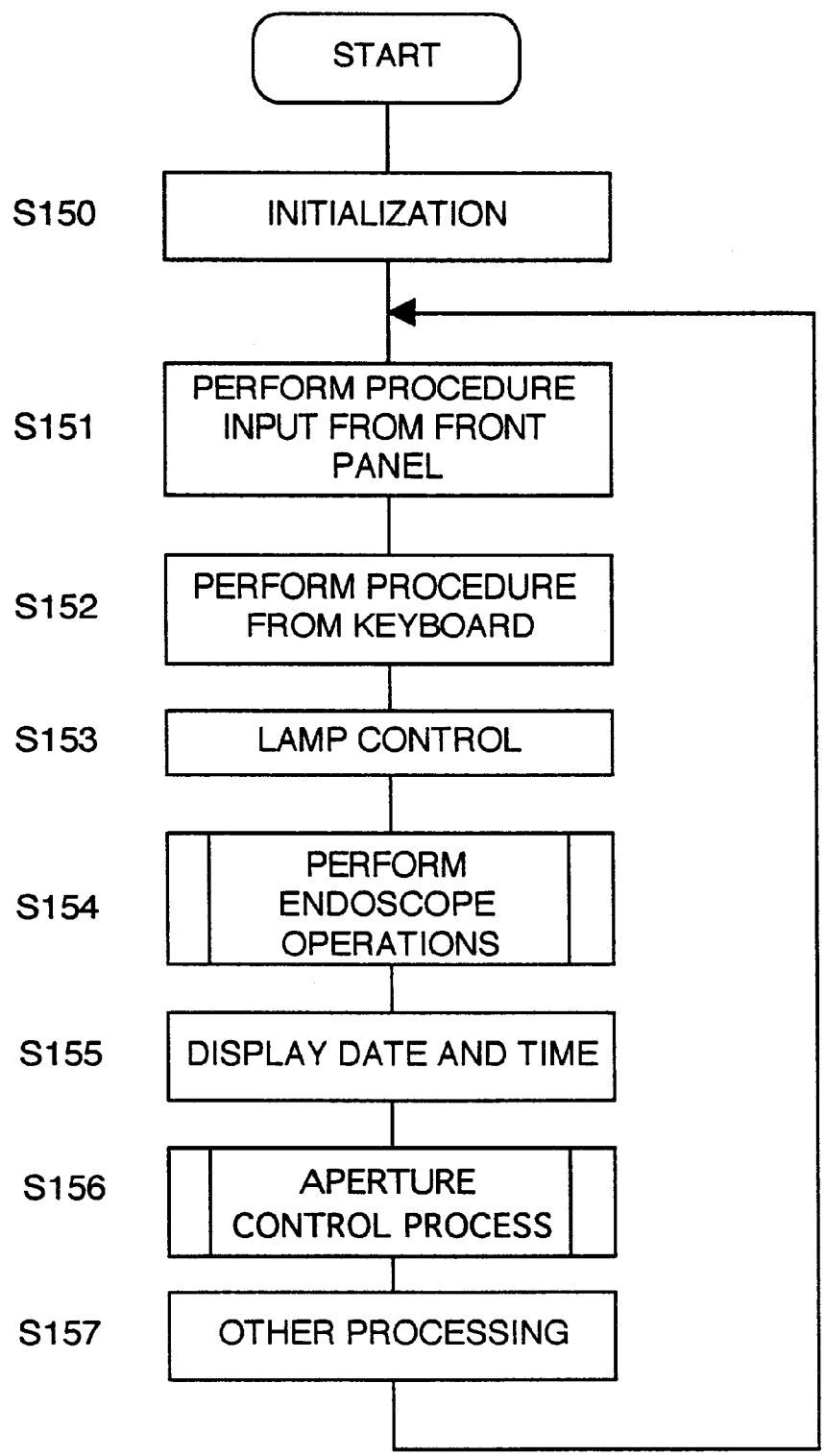
FIG. 15 shows a flowchart of a main program stored in the ROM of the microprocessor, shown in FIG. 5, according to a third embodiment of the present invention.

FIG. 15 illustrates a main program of the operation of a third embodiment of the present invention. In the third embodiment, the motor drive control is executed as a part of a subroutine for controlling the amount of light emitted by the lighting unit, and not as an interrupt procedure. Further, in this embodiment, the DIP switch 11 sets the values N1 and N2, using software in the microprocessor 30, in order to set the time interval between executions of the subroutine.

The main program for the third embodiment is similar to the main program for the first embodiment, shown in FIG. 8, with steps S150 through steps S155 the same as steps S80 through S85.

Thus, in step S150, the predetermined initialization routine is executed. Then, steps S151 and S152 execute a procedure set by the switch panel 201 and a keyboard input, respectively. A procedure for controlling an operation of the lamp controlling circuit 27 is then executed in step S153.

Step S154 executes a normal operation of the endoscope 1, while step S155 executes a procedure for displaying the date and time. In step S156, the subroutine for controlling the amount of light emitted by the lighting unit is called, and other processing is executed in step S157. The program is then repeated.

In step S154 of the main program, the subroutine called to perform the endoscope operations is similar to the subroutine in the second embodiment, shown in FIG. 12. However, in step S123, only the type of endoscope is determined (i.e., by reading the memory 9, or from a setting of the DIP switch 11), since the values N1 and N2 are set previously using the DIP switch 11.

Figure 16:
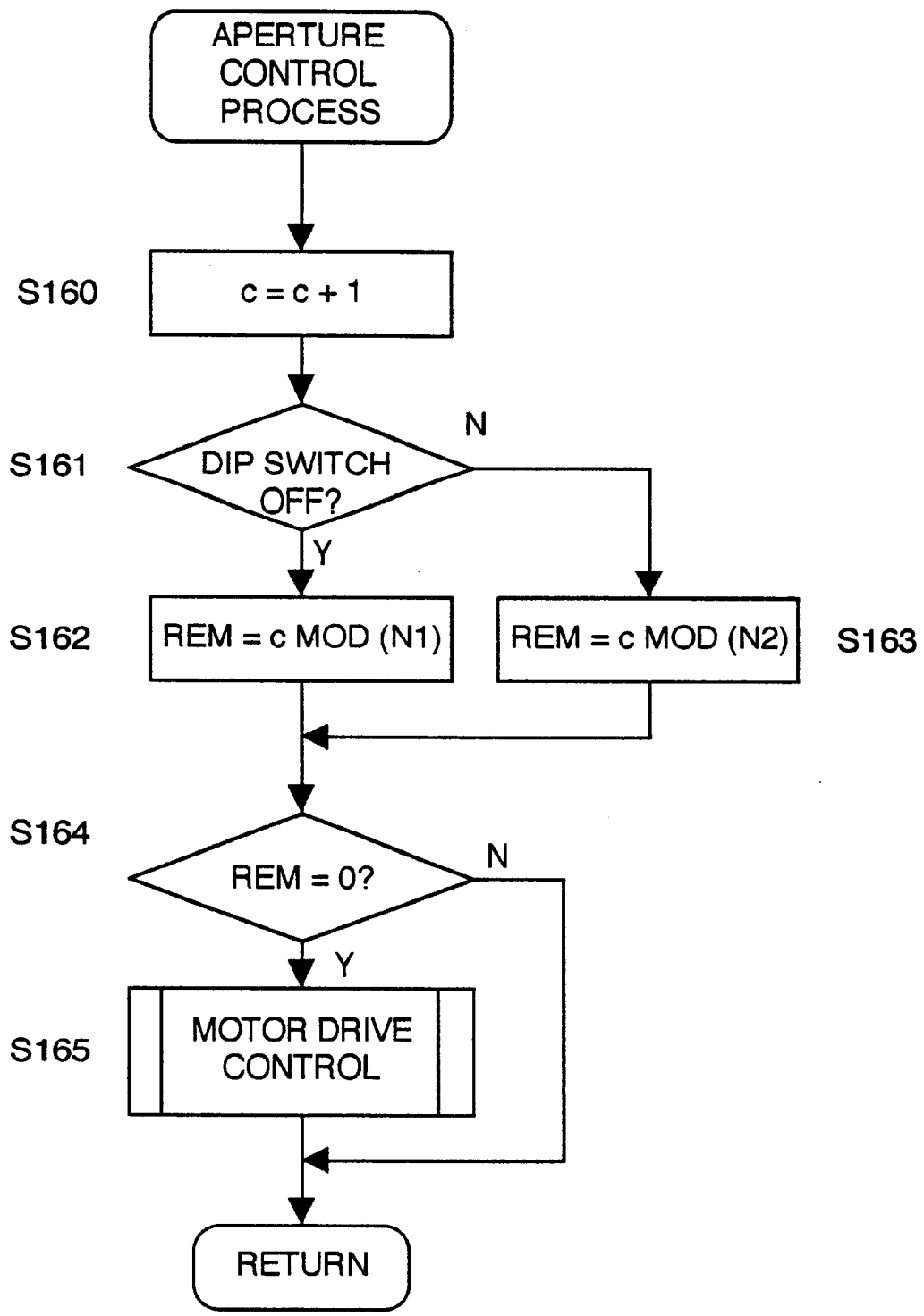
FIG. 16 shows a flowchart of a subroutine for a controlling the amount of light, according to the third embodiment of the present invention.

FIG. 16 shows a flowchart of a subroutine for controlling the amount of light emitted by the lighting unit, which is called in step S156 of the main program. In this routine a variable c is used as a counter. In step S160, the value of c is incremented by 1 (one). Step S161 determines whether the DIP switch 11 is OFF. If the DIP switch 11 is OFF (S161:Y), then c is divided by the value N1 in step S162, and a remainder REM is obtained. If the DIP switch 11 is ON (S161:N), then c is divided by the value N2 in step S163, and the remainder REM is obtained. Then, step S164 determines whether the remainder REM is equal to 0 (zero). If REM is equal to 0 (S164:Y), the motor driving subroutine shown in FIG. 9 is called in step S165, and then the routine ends. If REM is not equal to 0 (S164:N), the routine ends.

Thus, in the third embodiment, the interval at which the motor driving pulses are applied is controlled by the setting of the DIP switch 11. If, for example, N1 is set equal to 17 when the DIP switch 11 is turned OFF; the motor driving procedure is then executed approximately every 50 ms. Further, if N2 is set equal to 27 when the DIP switch is turned ON, then the motor driving procedure is executed approximately every 80 ms.

In the third embodiment, the DIP switch 11 can usually be set to its OFF position. Therefore, the control of the light amount emitted by the lighting unit is executed more frequently, and has a faster response time. If the light shield 25 does not coverage to a certain position as a result of a change in a characteristic of the light amount controlling device when the endoscope type is changed or the lamp is changed, by turning the DIP switch 11 ON, the hunting condition will be prevented.

In the above-described embodiment, with the DIP switch 11, one of only two conditions is selectable. However, more than two conditions, or more than two constants Nn (n=1, 2, 3, . . . ) can be used. In this case, the optimum time interval of driving the motor 26 can be selected depending on the kind of the endoscope, ambient conditions, mechanical characteristics, and/or preferences of an operator.

According to the third embodiment, since the time interval of the motor driving procedure is varied, the response of the movement of the light shield 25 can be made as quickly as possible without hunting. Further, even if hunting occurs as a result of a slow response in the changing of the brightness after driving the stepping motor 26, by elongating the time period, and without changing the software or hardware, the operation of the light amount controlling device can be made stable.

Further, as described above, the motor driving operation can be executed as an interruption procedure or a part of a normal procedure. Furthermore, the time interval can be determined in software or by a manual operation, or in accordance with the type of endoscope attached to the video processor, or by setting a DIP switch. The setting of the time interval is not, however, limited to these methods, but may another method, such as direct data entry etc.

Phase Controlled Driving Embodiments

Figure 17:
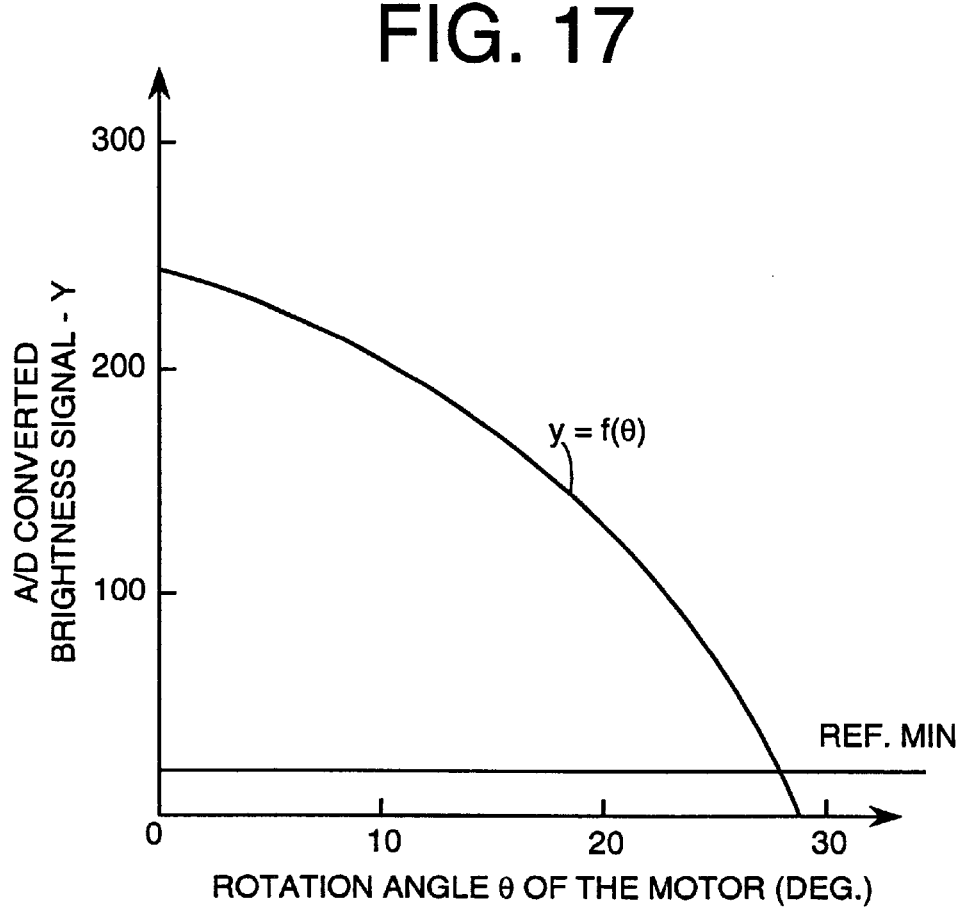
FIG. 17 shows a graph of a relationship between a rotation angle of the stepping motor and a brightness of an image observed using the endoscope.
Figure 18:
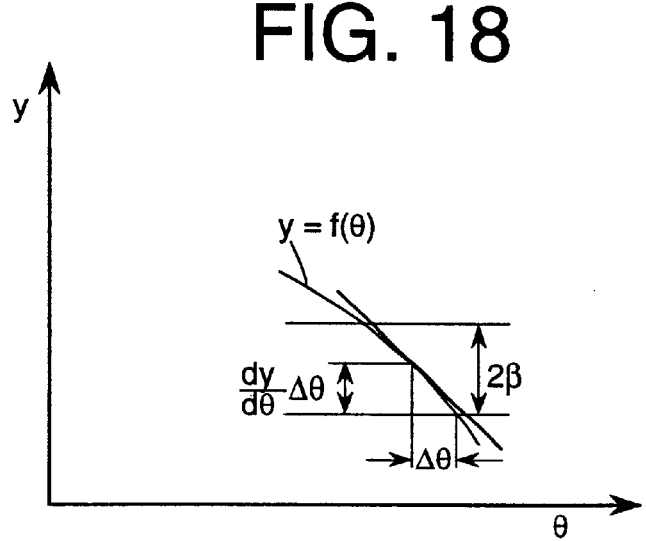
FIG. 18 shows an enlarged portion of the graph shown in FIG. 17.

FIG. 17 shows the curve y=f(θ) which is the relationship between the rotation angle θ and the brightness signal value (A/D converted value) y of the image observed using the endoscope 1. FIG. 18 shows an enlarged view of a portion of the curve y=f(θ) shown in FIG. 17. Hunting will not occur if the following equation, as illustrated in FIG. 18, is satisfied:

$$\left|\frac{dy}{d\theta}\right|\Delta\theta \le 2\beta \qquad (a)$$

therefore $$\left|\frac{dy}{d\theta}\right| \le \frac{2\beta}{\Delta\theta}$$

where,
  β is a limit relative to the reference brightness value, of the allowed brightness signal (i.e., the allowed brightness range is equal to the reference brightness signal±β),
  Δθ is a rotation angle at each motor driving operation, and 1|dy/dθ| is a slope of a tangent [on a tangent] of the curve y=f(θ) at the reference brightness value.

Further, the stepping motor 26 is considered to have no delay when driven by the control system.

If the curve of y=f(θ) is a monotonically decreasing convex function, then as shown in FIG. 17, the absolute value of |dy/dθ| increases as θ increases. Therefore, if θ is relatively high, equation (a) above may not be satisfied. In this case, the method of exciting the stepping motor 26 is switched from 2 phase excitation to 1–2 phase excitation (i.e., excitation of the motor alternates between single phase and two phase, with each driving pulse). When the motor is driven with 1–2 phase excitation, the rotation angle $\Delta\theta_1$ of the stepping motor 26 is equal to a half the rotation angle $\Delta\theta_2$ when the motor is driven with 2 phase excitation. Therefore by driving the stepping motor 26 with 1–2 phase excitation, 2β/Δθ is doubled and equation (a) is satisfied.

For example, if one pulse is applied to the stepping motor 26, when using 2 phase excitation, the resulting rotation angle $\Delta\theta_2$ is 0.5 degrees, and β equals 1. The right side of the equation (a) is therefore equal to 4.

According to the curve shown in FIG. 17, if θ is greater than 15 degrees, |dy/dθ| is greater than four. Therefore, in the range where θ is greater than 15 degrees, equation (a) is not satisfied. If the motor excitation method is switched to 1–2 phase method, however, 2β/Δθ is equal to 8. According to the curve shown in FIG. 17, in the range where θ is greater than 15 degrees, |dy/dθ| is less than 8. Therefore, by switching the motor to have 1–2 phase excitation, equation (a) is satisfied when θ is greater than 15 degrees. Thus, since the change in brightness per unit degree of rotation of the stepping motor 26 when 1–2 phase excitation is employed is equal to half the change in brightness per unit degree of rotation of the stepping motor 26 when 2 phase excitation is employed, the accuracy of the movement of the stepping motor 26 is increased, and the hunting problem can be avoided.

Figure 19:
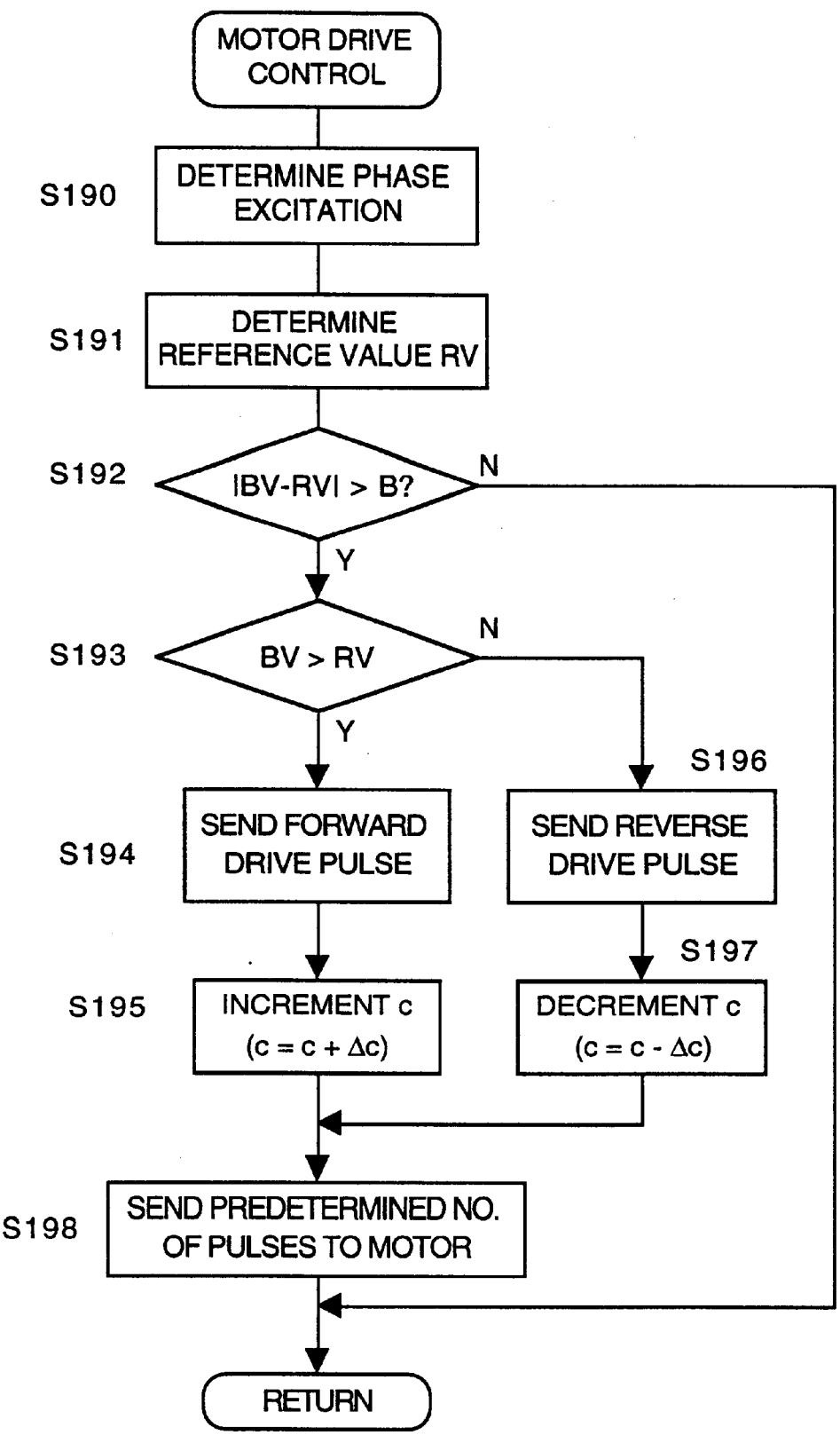
FIG. 19 shows a flowchart of an interrupt procedure used to control a driving of the stepping motor of the light amount controlling device, according to a fourth embodiment of the present invention.

FIG. 19 shows a flowchart of an interrupt routine for controlling the driving of the stepping motor 26 according to a fourth embodiment of the present invention. In this embodiment, the PIT 44 is programmed such that the interrupt routine is executed every 30 Ms. Further, the main program is the same program used in the first embodiment, and shown in FIG. 8.

In the fourth embodiment, a counter value c represents the cumulative number of pulses that have been applied to the stepping motor 26, and P represents a number of pulses to be applied to the stepping motor 26 during one execution of the interrupt routine. The motor excitation method is given by the flag U2. If U2=0, then 2 phase excitation is used. If U2=1, then 1–2 phase excitation is used. Further, a value N is equivalent to the number of pulses applied to the motor 26 when equation (a) is satisfied, and Δc is a value by which the counter c is incremented.

Figure 20A:
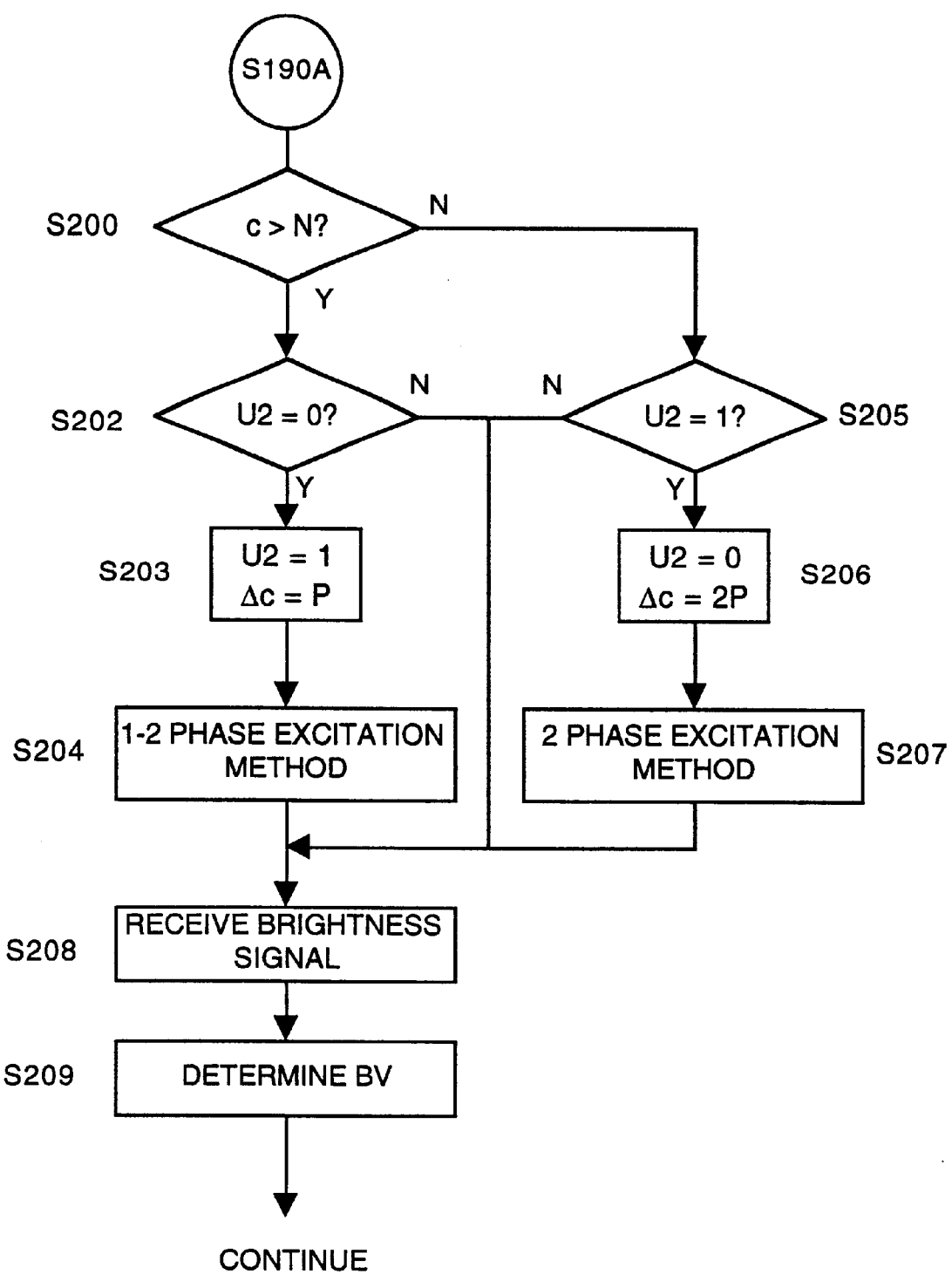
FIG. 20A shows a flowchart of a process for determining a number of phases of excitation of the stepping motor, according to the fourth embodiment.

In step S190, the phase of excitation of the stepping motor 26 is determined. FIG. 20A shows a flowchart of a process for determining a number of phases of excitation of the stepping motor 26 according to the fourth embodiment.

Initially, in step S200, the counter value c is compared with the predetermined value N. If c is not greater than N (S200:N), then step S205 determines whether the stepping motor 20 has 2 phase excitation by checking the setting of the flag U2. If U2 is equal to 1 (S205:Y), then the flag U2 is set to 0 and Δc is set equal to 2P, in step S206. Then, in step S207, the 2 phase excitation method is set. If the flag U2 is not equal to 1 (S205:N), then steps S206 and S207 are skipped.

If the value of c is greater than N (S200:Y), then control proceeds to step S202, which determines whether the stepping motor has 1–2 phase excitation by checking the setting of the flag U2. If U2 is equal to 0 (S202:Y), then the flag U2 is set to 1 and Δc is set equal to P, in step S203. Then, in step S204, the 1–2 phase excitation method is set. If the flag U2 is not equal to 0 (S202:N), then steps S203 and S204 are skipped.

In step S208, the brightness signal is received, and the brightness value BV corresponding to the received brightness signal is determined in step S209. Control then continues to step S191 of the flowchart shown in FIG. 19.

In step S191, the reference value RV is determined in accordance with the input brightness level IBL set by the operator of the endoscope 1. Step S192 then determines whether the brightness value BV of the received brightness signal is within the allowed brightness range (i.e., |RV−BV|>β).

If the brightness value BV is not within the allowed brightness range (S192:Y), the brightness value BV is compared with the reference value RV, in step S193. Otherwise (S192:N), the routine is ended.

Then, if the brightness level is greater than the reference brightness level (S193:Y), the forward drive pulse is sent, in step S194, and the counter value c is incremented by Δc, in step S195. Otherwise (S193:N), the reverse drive pulse is sent in step S196, and the counter value c is decremented by Δc, in step S197.

Step S198 then sends the predetermined number of pulses to the motor, and the routine is ended.

FIG. 21 is a table showing the relationship between the count c, the angle of rotation of the light shield 25, and the amount of light transmitted to the converging lens 24 from the light source 22. As shown in FIG. 21, when the count c is 0, the angle of rotation is 0°, and the amount of light transmitted is large. As the count c increases, the angle of rotation increases, and the amount of light transmitted becomes smaller. When the count c is 120, the angle of rotation is 30°, and the amount of light transmitted is small.

As described above, when the light shield 25 is rotated in order to reduce the amount of light transmitted, the method of exciting the motor 26 is changed from 2 phase excitation to 1–2 phase excitation. Further, if the cumulative number of pulses that has been sent to the stepping motor as counted by counter c is less than or equal to the predetermined value N, then the stepping motor 26 is driven with 2 phase excitation. Therefore, the light shield 25 is initially rotated quickly. After the cumulative number of pulses has exceed the predetermined value N, the stepping motor 26 is driven with 1–2 phase excitation. Thus, the light shield 25 is rotated in smaller steps, and therefore more accurately, during each successive interrupt. As a result of the control procedure described above, the light shield 25 is rotated such that the amount of light transmitted is changed quickly and accurately, while preventing hunting.

Figure 20B:
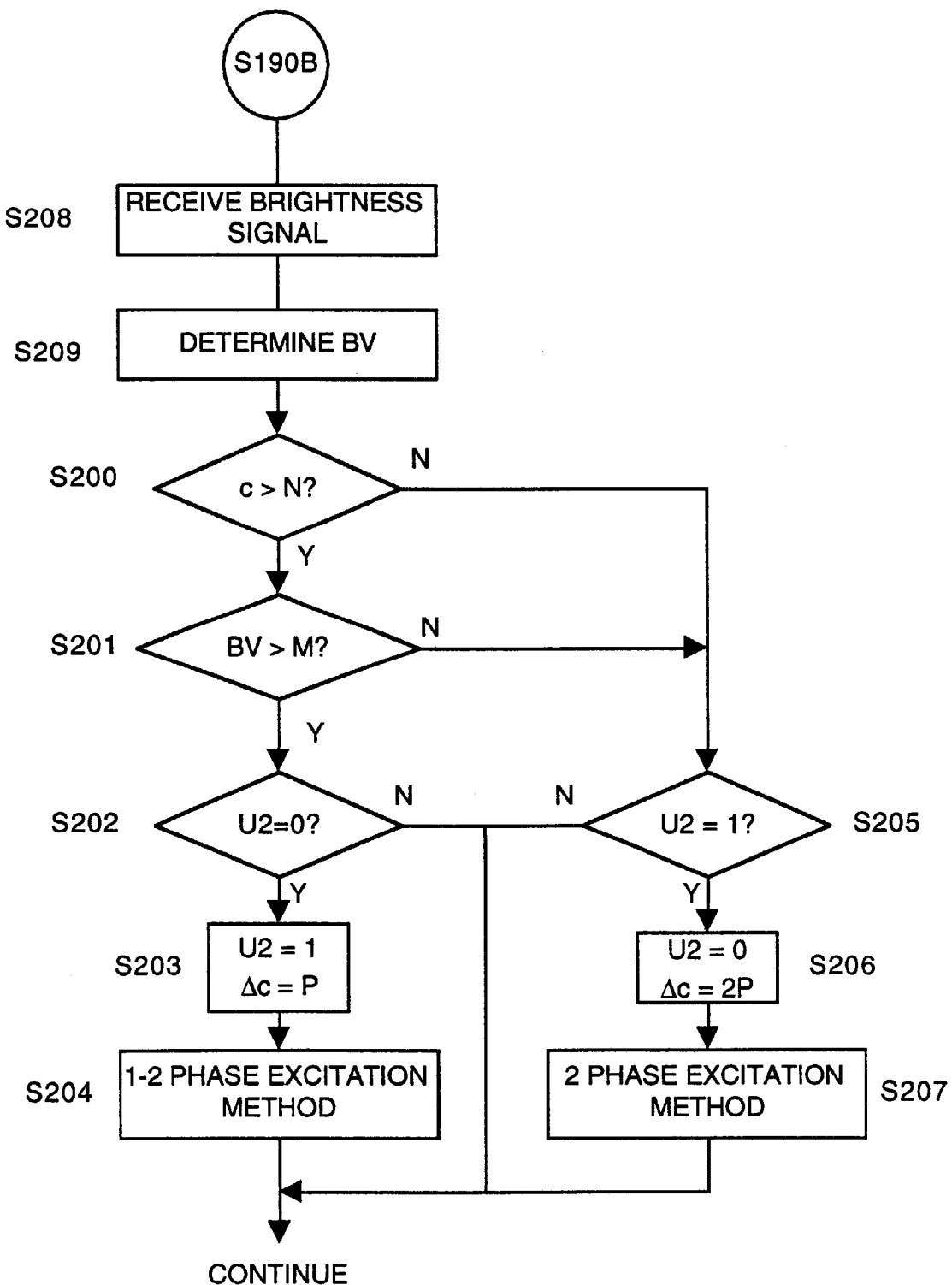
FIG. 20B shows a flowchart of a process for determining a number of phases of excitation of the stepping motor, according to a modification of the fourth embodiment.

FIG. 20B shows a flowchart of a process for determining a number of phases of excitation of the stepping motor 26 in step S190, according to a modified control of the fourth embodiment. The process carried out is similar to that described above and shown in the flowchart of FIG. 20A, except that steps S208 and S209 are performed before the type of excitation of the motor has been determined. Further, an additional step S201 is performed.

As shown in FIG. 20B, the brightness signal is received in step S208, and then the brightness value BV is determined in step S209. Then in step S200 the value of c is compared with the predetermined value N. If c is less than or equal to N (S200:N), steps S205 through S207 are executed as described above.

However, if c is greater than N (S200:Y), then step S201 is executed before step S202. In step S201, the value of BV is compared with a predetermined value M. The predetermined value M is smaller than the minimum reference value. If BV is greater than M (S201:Y), then steps S205 through S207 are executed, and the stepping motor 26 is set to be driven with 2 phase excitation. If BV is less than or equal to M (S201:N) then steps S202 through S204 are executed as described above and the stepping motor 26 is set to be driven with the 1–2 phase excitation.

As described above, in the modified fourth embodiment, even if the cumulative number of pulses as counted by counter c is larger than the predetermined value N, if the brightness value BV is larger than the predetermined value M, the stepping motor 26 is driven with 2 phase excitation. With this modified embodiment, in case the brightness value is large, the stepping motor 26 will be driven with 2 phase excitation for a longer time and therefore the time required to rotate the light shield 25 such that the brightness value is brought into the allowed brightness range is reduced. Further, when the value of BV is less than M, the stepping motor 26 is driven with 1–2 phase excitation, and therefore the accuracy of rotation of the light shield 25 remains high when the brightness value is near the allowed brightness range.

Figure 22:
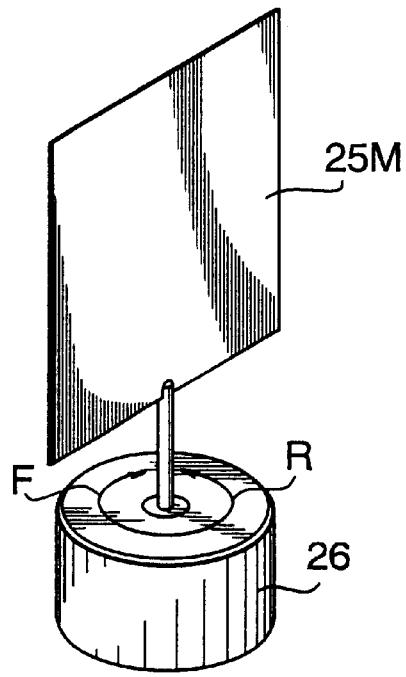
FIG. 22 is a perspective view of a light shield used in a modification of the fourth embodiment of the present invention.
Figure 23:
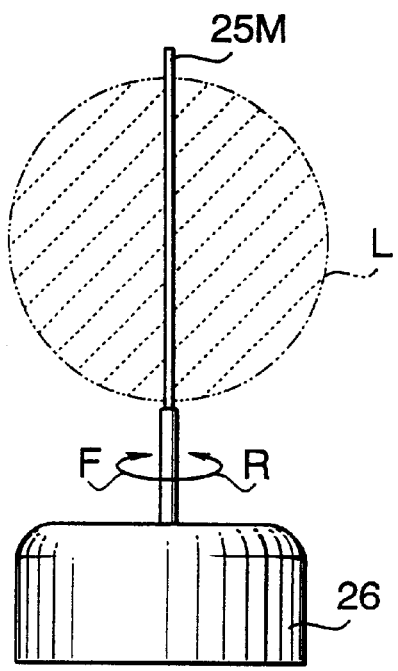
FIG. 23 is a side view of the light shield shown in FIG. 22.

FIGS. 22 and 23 show a light shield 25M used in a second modification of the fourth embodiment described above. The light shield 25M is operated with the control of the flowcharts shown in FIGS. 19 and 20A.

In the second modification of the fourth embodiment, the light shield 25M is planar and has a rectangular cross-section. Further, the relationship between the angle of rotation of the light shield 25 M and the A/D brightness signal y, illustrated in FIG. 24, is different than the relationship between the angle of rotation of the light shield 25 and the A/D brightness signal y shown in FIG. 17.

Figure 24:
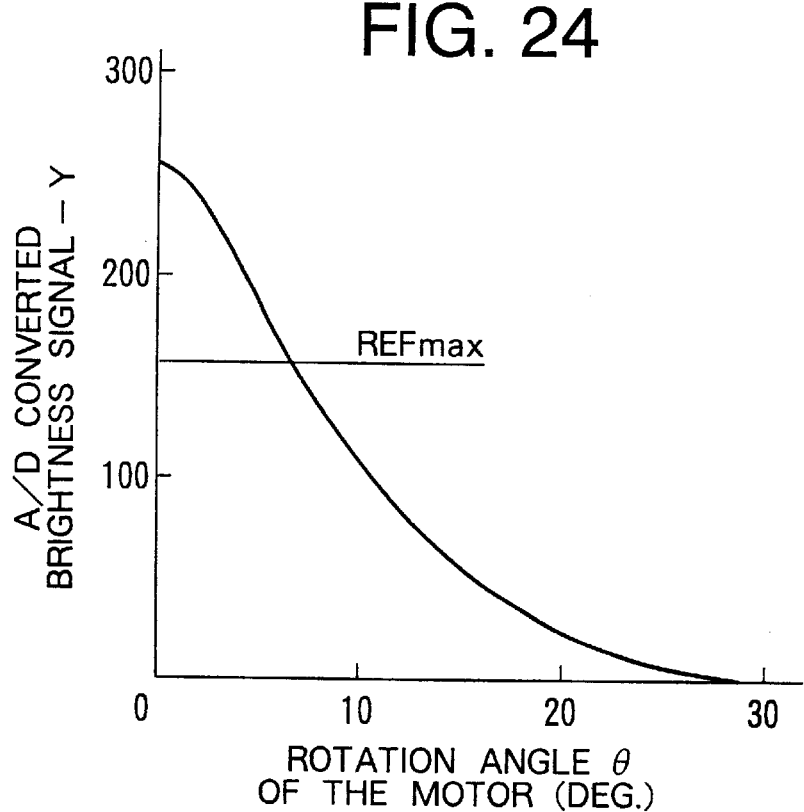
FIG. 24 shows a graph of a relationship between a rotation angle of the stepping motor and a brightness of an image observed using the light shield shown in FIG. 22.

As shown in FIG. 24, $y=g(\theta)$
where, y is the brightness and
$\theta$ is the angle of the rotation.

The curve $y=g(\theta)$ is also a monotonically decreasing function. Further, $|dy/d\theta|$ generally decreases as $\theta$ increases.

Therefore, in the second modification of the fourth embodiment, the stepping motor 26 is driven with 1–2 phase excitation if the angle of rotation $\theta$ is less than or equal to a predetermined angle, and 2 excitation if the angle of rotation $\theta$ is larger than the predetermined angle. In this case the predetermined angle is equal to the angular position of the stepping motor 26 when the counter value is equal to a value N.

If the light shield 25M is driven with the control of the flowcharts shown in FIGS. 19 and 20B, the stepping motor 26 is driven with 1–2 phase excitation when $\theta$ is less than or equal to a predetermined angle, and driven with 2 excitation when $\theta$ is greater than the predetermined value. Further, if the brightness signal value exceeds the maximum reference value REFmax, (REFmax=161, see FIG. 25), then the stepping motor 26 is driven with 2 excitation regardless of the counter value c.

Figure 25:
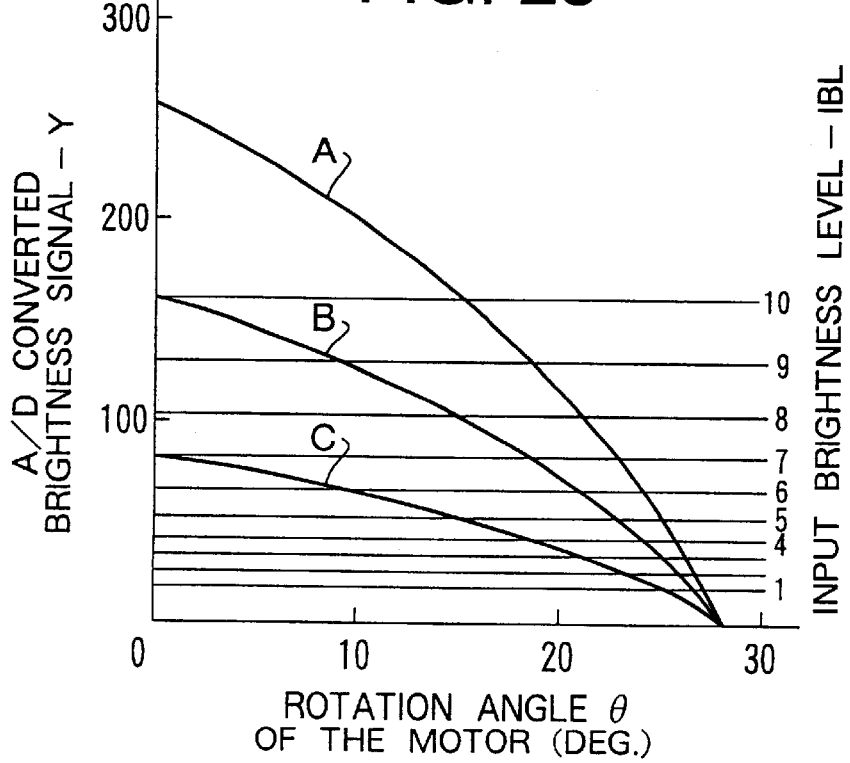
FIG. 25 shows a graph of a brightness of an object observed by three different types of endoscopes, as a function of an angle of rotation of the stepping motor.

FIG. 25 shows a graph of the brightness y of the object observed by three different types of endoscopes, as a function of the angle of rotation $\theta$ of the stepping motor 26. The endoscope A represents the endoscope 1 used for the digestive system, while endoscope C represents an endoscope used in the respiratory system. The difference in the brightness characteristics of the endoscopes can be attributed to the different f-numbers of the objective lenses and the different number of optical fibers used in the respective endoscopes.

As further shown in FIG. 25, the value of $|dy/d\theta|$ for the endoscope C is small for all values of $\theta$, and therefore the stepping motor 26 can always be driven with 2 phase excitation.

Therefore, in a third modification of the fourth embodiment, the type of endoscope is first transmitted to the video processor 20. If the endoscope 1 is a type A or B, then step S202 is performed as described above. However, if the endoscope is a type C, then control proceeds to step S207, where the stepping motor 26 is set to be driven with 2 excitation.

According to the third modification of the fourth embodiment, the method of driving the stepping motor 26 is determined in accordance with the type of endoscope being used, the brightness of the observed image, and position of the light shield 25. Therefore, the brightness of the observed image can be adjusted quickly without causing hunting.

Brightness Level Range Setting Embodiments

Figure 26:
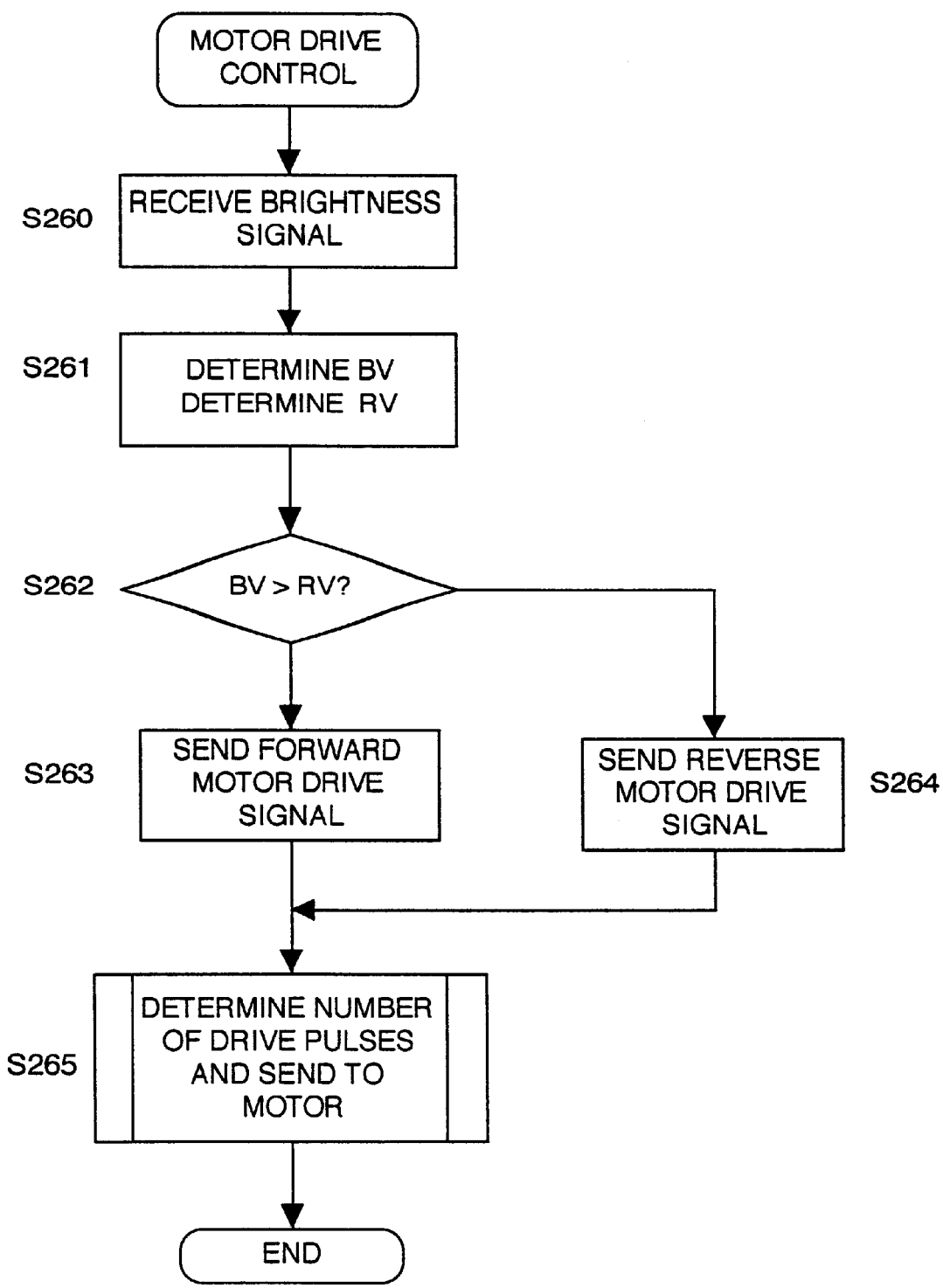
FIG. 26 shows a flowchart of an interrupt procedure used to control a driving of the stepping motor of the light amount controlling device, according to a fifth embodiment of the present invention.

FIG. 26 shows a flowchart illustrating the control of the driving of the stepping motor 26, according to a fifth embodiment of the present invention. The fifth embodiment also operates using the main program shown in FIG. 8, with the interrupt being executed every 30 ms. Further, the number of pulses to be applied to the stepping motor 26 during each interrupt is 2. Therefore, after each interrupt, the stepping motor 26 is rotated 1°.

In step S260, the brightness signal is received. Step S261 determines the brightness value BV of the brightness signal, and the reference value corresponding to an input brightness level IBL. Then, step S262 determines whether the brightness value BV is greater than the reference value RV. If the brightness value BV is greater than the reference brightness level RV (S262:Y), the forward drive signal is sent, in step S263. Otherwise (S262:N), the reverse drive signal is sent in step S264.

A subroutine for determining the number of drive pulses to be sent to the motor, is then called in step S265. After the number of drive pulses has been determined and then sent to the motor, the routine is ended.

FIG. 27 is a table showing the relationship between the change in the brightness signal value $\Delta y$ and the rotation angle $\theta$ of the stepping motor 26, which corresponds to the curve A of the graph in FIG. 25. As shown in FIG. 27, the brightness levels are arranged into 5 groups, with the change in brightness level $\Delta y$ per degree of rotation of the light shield 25, decreasing as the brightness level y increases.

Figure 28:
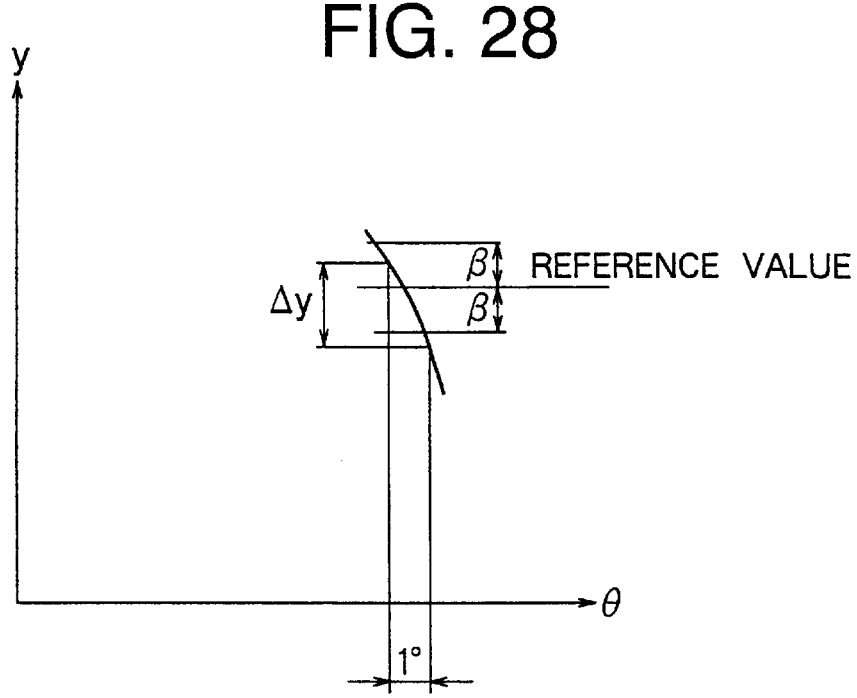
FIG. 28 shows an enlarged portion of the graph shown in FIG. 25.

FIG. 28 shows a partially enlarged view of the graph of FIG. 25. As shown in FIG. 28, in order to adjust the light shield 25 such that hunting does not occur, the change in brightness signal value $\Delta y$ per change in rotation of stepping motor 26 during an interrupt (i.e., 1°) must be less than the allowed brightness range (i.e., $2\beta$).

In the fifth embodiment, the allowable brightness ranges $\beta n$ (n=1, 2, 3) are determined such that $\beta 1=2$, $\beta 2=3$, and $\beta 3=4$. Further, the brightness range is selected in accordance with the input brightness level IBL set using the switch panel 201. The range $\beta 1$ is used when the selected brightness level is 10. If the selected input brightness level IBL is 9, 8, or 7, then the range $\beta 2$ is used. If the selected input brightness level IBL is 6 or lower, then the range $\beta 3$ is used.

As shown above, as the input brightness level IBL decreases, the allowed brightness range $\beta n$ increases, since the change in brightness per degree of rotation is small when the brightness value BV is high, and is large when the brightness value BV is low, as shown in FIG. 25. Or in other words, $|dy/d\theta|$ increases as $\theta$ increases. By selecting the allowed brightness range as described above, a quick response in rotation of the light shield can be obtained without hunting.

Figure 29:
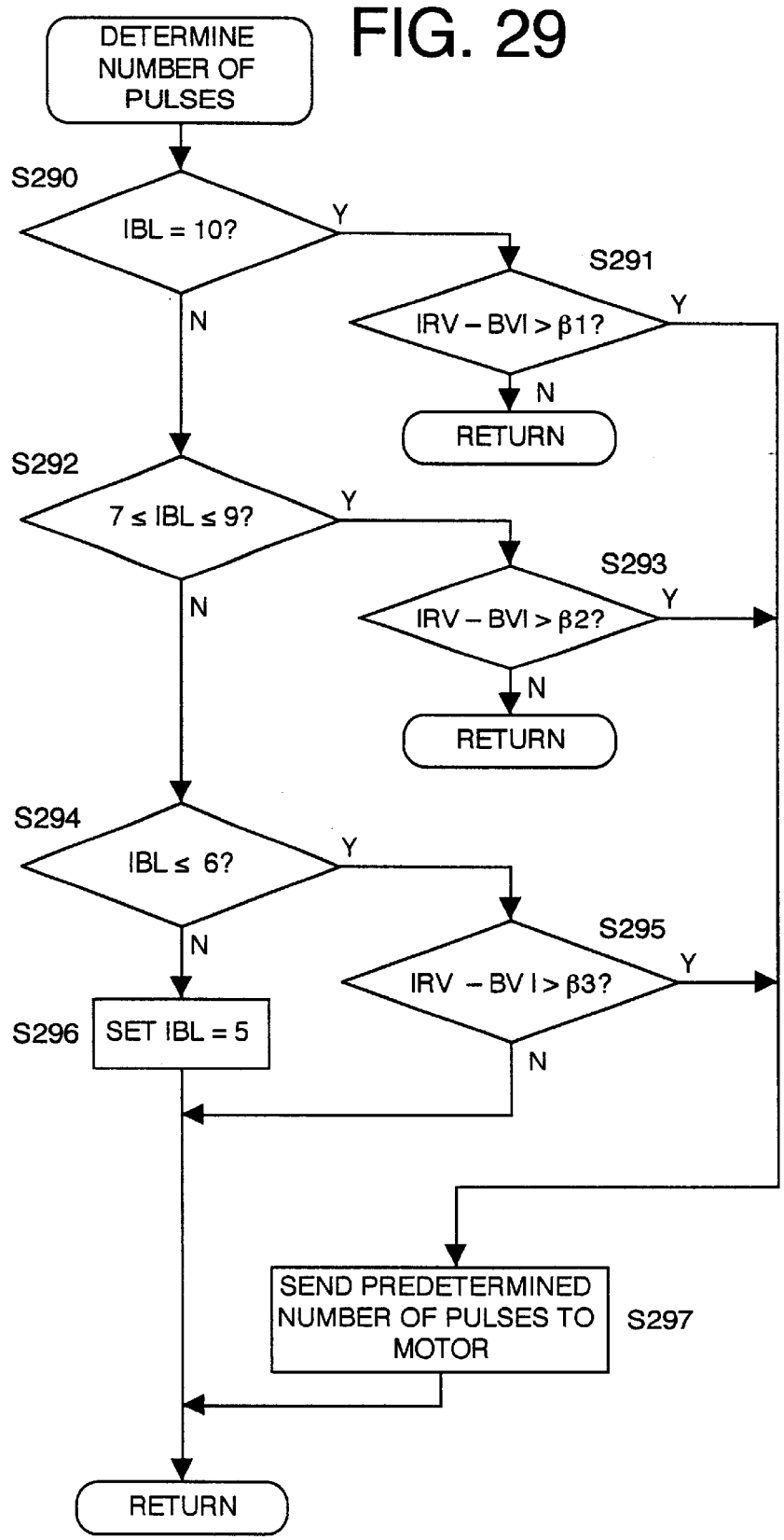
FIG. 29 shows a flowchart of a process for determining a number of pulses to send to the stepping motor, according to the fifth embodiment of the present invention.

FIG. 29 is a flowchart illustrating step S265 of FIG. 26, in accordance with the fifth embodiment.

Step S290 determines whether the input brightness level IBL is equal to 10. If the input brightness level IBL is equal to 10 (S290:Y), then step S291 determines whether $|RV-BV|$ is greater than $\beta 1$ (i.e., two) If $|RV-BV|$ is greater than $\beta 1$ (S291:Y), then the predetermined number of pulses (i.e., two) is applied to the stepping motor 26, in step S297.

If $|RV-BV|$ is not greater than $\beta 1$ (S291:N), then the subroutine ends, and the interrupt procedure shown in FIG. 26 is terminated.

If the input brightness level IBL is equal to 9, 8 or 7 (S290:N, S292:Y)), and $|RV-BV|$ is greater than $\beta 2$ (S293:Y), control proceeds to step S297 where the predetermined number of pulses are applied to the stepping motor 26. However, if |RV−BV| is not greater than β2 (S293:N), then the subroutine ends and the interruption procedure is terminated.

If the input brightness level IBL is 6 or lower (S294:Y), and |RV−BV| is greater than β3 (S295:Y), then control proceeds to step S297 where the predetermined number of pulses are applied to the stepping motor 26. If |RV−BV| is not greater than β3 (S295:N), then the subroutine ends and interruption procedure is terminated.

If the input brightness level IBL does not have a value between 1 through 10 inclusive, then the input brightness level IBL is forcibly set to a default value, e.g., 5, in step S296, and the interruption procedure is terminated.

As described above, in the fifth embodiment, the number of driving pulses sent to the stepping motor 26 is a constant number for all input brightness levels. However, the allowed brightness range β changes in accordance with the input brightness level IBL.

FIG. 30 is a table showing the relationship between the angle of rotation θ of the stepping motor 26, and the change in brightness level Δy per degree of rotation of the stepping motor 26, according to a modified control of the fifth embodiment. This table also corresponds to the curve A shown in FIG. 25. In the modified fifth embodiment, the range βn is changed in accordance with the angle of rotation θ of the stepping motor 26. Further, the number of pulses sent to the stepping motor 26 is two.

Figure 31:
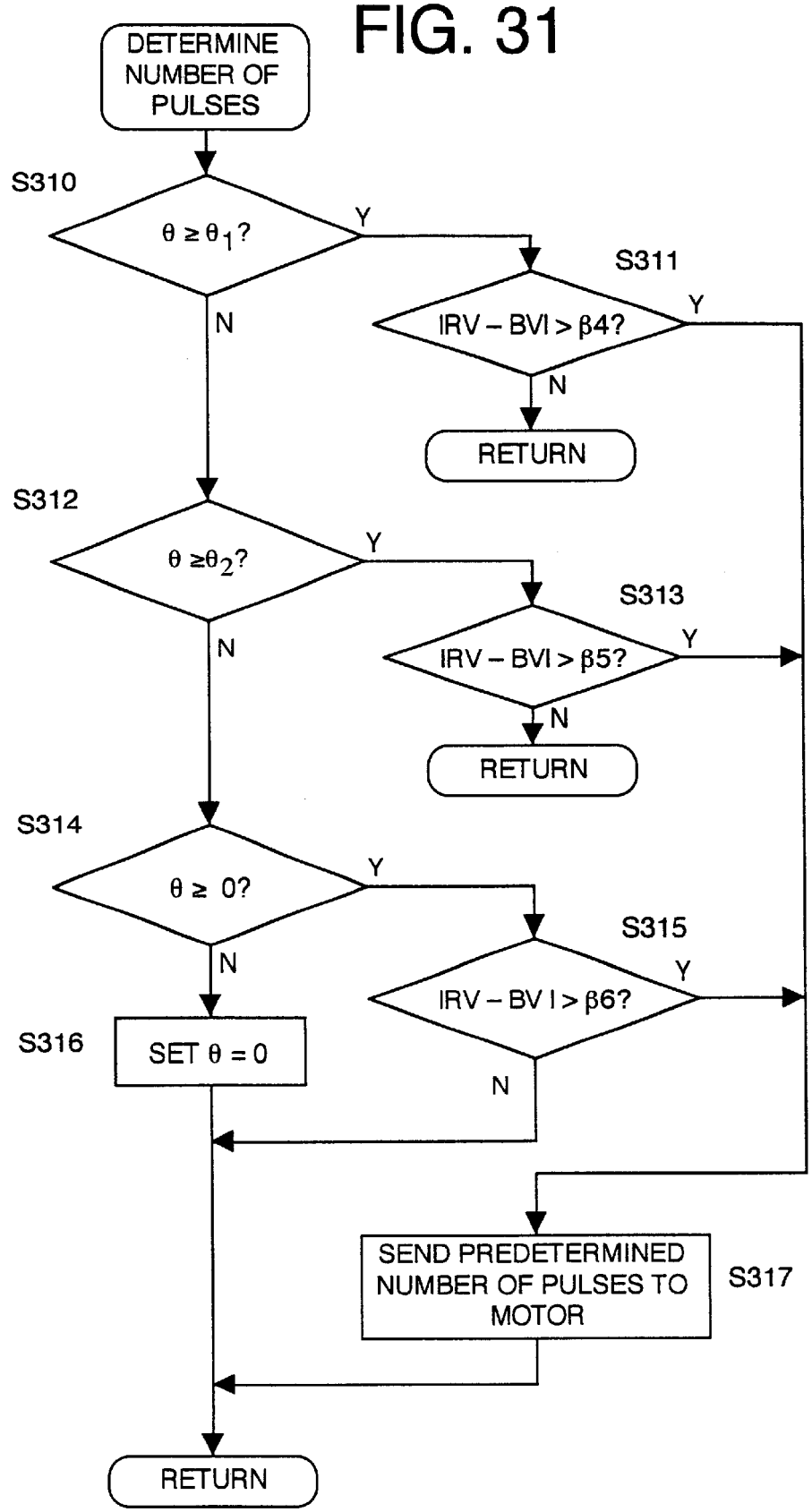
FIG. 31 shows a flowchart of a process for determining a number of pulses to send to the stepping motor, according to the first modification of the fifth embodiment of the present invention.

FIG. 31 shows the motor driving subroutine according to the modified fifth embodiment, called in step S265 of the interrupt routine, shown in FIG. 26.

In step S310, if the angle of rotation θ is greater than or equal to $\theta_1$ (S310=Y), then step S311 determines whether |RV−BV| is greater than β4. If |RV−BV| is greater than β4 (S311:Y), then the predetermined number of pulses (i.e., two) is applied to the stepping motor 26, in step S317. If |RV−BV| is not greater than β4 (S311:N), then the subroutine ends, and the interrupt procedure shown in FIG. 26 is terminated.

If the angle of rotation θ is greater than or equal to $\theta_2$ (S310:N, S312:Y), and |RV−BV| is greater than β5 (S313:Y), then the predetermined number of pulses are applied to the stepping motor 26, in step S317. However, if |RV−BV| is not greater than β5 (S313:N), then the subroutine ends and the interruption procedure is terminated.

If the angle of rotation θ is greater than or equal to 0 (S312:N, S314:Y), and |RV−BV| is greater than β6 (S315:Y), then the predetermined number of pulses are applied to the stepping motor 26, in step S317. If |RV−BV| is not greater than β6 (S315:N), then the subroutine ends and interruption procedure is terminated.

If the angle of rotation θ is less than 0 (S314:N), then the angle of rotation θ is reset to 0, and the interruption procedure is terminated.

In the modified fifth embodiment, the allowed brightness ranges βn are set such that β4=β5=3, and β6=2. Further, as described above, the allowed brightness range is set in accordance with the angular position of the light shield 25.

FIG. 32 has tables showing the relationship between the angle of rotation θ of the stepping motor 26, and the change in brightness level Δy per degree of rotation of the stepping motor 26, according to a second modified control of the fifth embodiment. The tables A, B and C correspond to the curves A, B and C, respectively, shown in FIG. 25. Curve A represents an endoscope used for the digestive system, curve B represents an endoscope used for the esophagus, and curve C represents an endoscope used for the respiratory system excluding the esophagus (i.e., such as the bronchial tubes, nose etc.).

In this embodiment, the range βn is changed in accordance with the angle of rotation θ of the stepping motor 26, and the type of endoscope.

Figure 33:
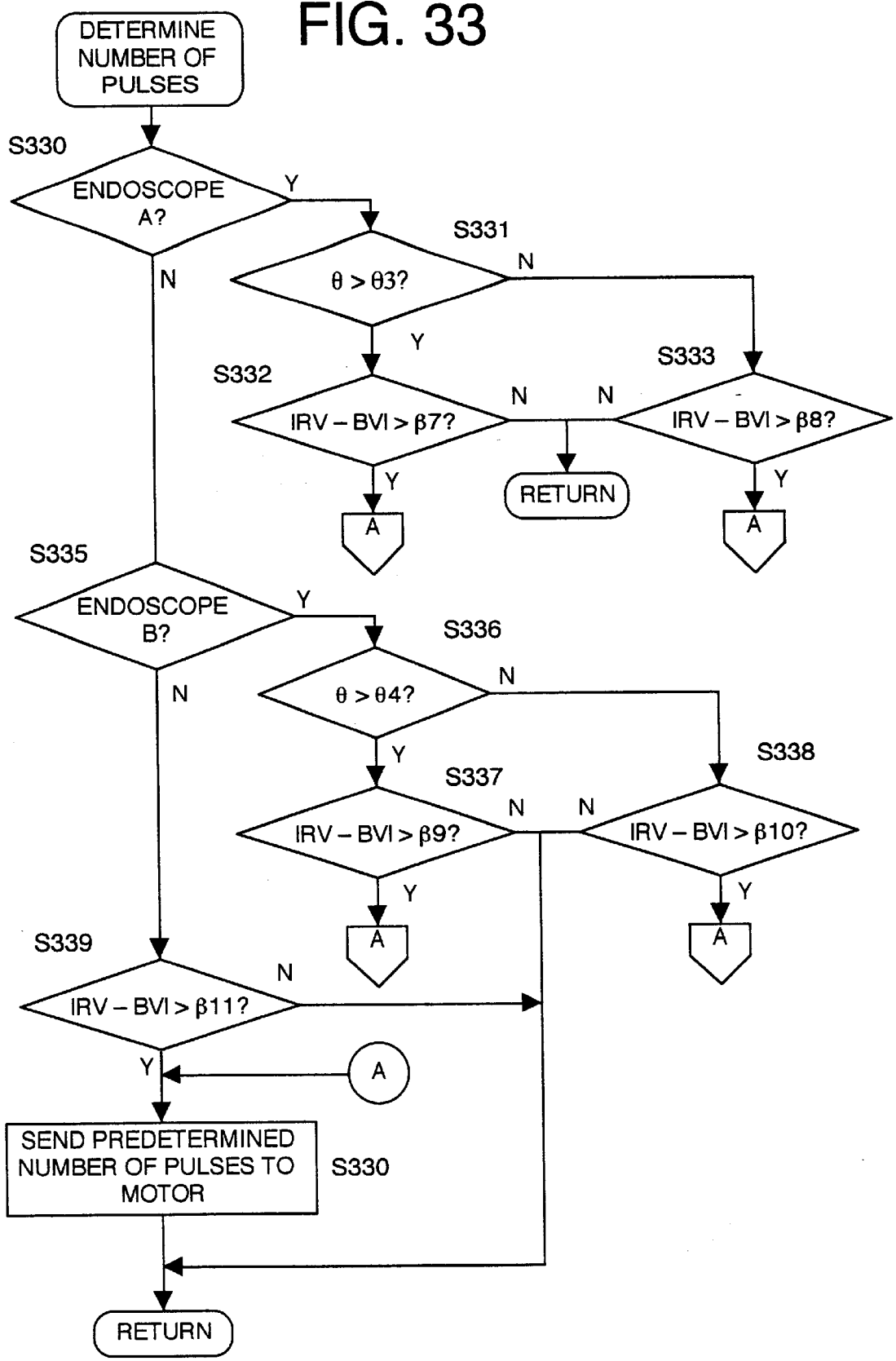
FIG. 33 shows a flowchart of a process for determining a number of pulses to send to the stepping motor, according to the second modification of the fifth embodiments of the present invention.

FIG. 33 shows the motor driving subroutine according to the second modified control of the fifth embodiment, called in step S265 of the interrupt routine, shown in FIG. 26.

Step S330 determines whether a type A endoscope is connected to the video processor 20. The endoscope type is stored in the memory 9, as described before.

If the endoscope is a type A endoscope (S330:Y), then step S331 determines whether the angle of rotation θ is greater than $\theta_3$. If the angle of rotation θ is greater than $\theta_3$, and |RV−BV| is greater than β7 (S331:Y, S332:Y), then the predetermined number of pulses is sent to the stepping motor 26 in step S340, and the subroutine is ended. If |RV−BV| is not greater than β7 (S332:N), then the subroutine ends, and the interrupt procedure is terminated.

If the angle of rotation θ is not greater than $\theta_3$, and |RV−BV| is greater than β8 (S331:N, S333:Y), then control proceeds to step S340 where the predetermined number of pulses is sent to the stepping motor 26. Otherwise (S334:N), the subroutine is ended, and the interrupt procedure is terminated.

If the endoscope is a type B endoscope (S330:N, S335:Y), then step S336 determines whether the angle of rotation θ is greater than $\theta_4$. If the angle of rotation θ is greater than $\theta_4$, and |RV−BV| is greater than β9 (S336:Y, S337:Y), then control proceeds to step S340 where the predetermined number of pulses is sent to the stepping motor 26. If |RV−BV| is not greater than β9 (S337:N), then the subroutine ends, and the interrupt procedure is terminated.

If the angle of rotation θ is not greater than θ4, and |RV−BV| is greater than β10 (S336:N, S338:Y), then control proceeds to step S340 where the predetermined number of pulses is sent to the stepping motor 26. Otherwise (S338:N), the subroutine is ended, and the interrupt procedure is terminated.

When the endoscope is a type C endoscope (S335:N), step S339 determines whether |RV−BV| is greater than β11. If |RV−BV| is greater than or equal to β11 (S337:Y) then the predetermined number of pulses is sent to the stepping motor 26, in step S340, and the subroutine is ended. Otherwise (S337:N), the subroutine is ended, and the interrupt procedure is terminated.

In the above described modified fifth embodiment, the allowed brightness ranges β7=4, β8=3, for the type A endoscope, β9=3, 10=2, for the type B endoscope, and β11=2, for the type C endoscope. Further, the threshold angle θ3 =23° and the threshold angle θ4=20°.

In the fifth embodiment described above, the number of pulses sent to the stepping motor 26 remains constant, while the allowed brightness range varies in accordance with the input brightness level. A sixth embodiment will be described below, in which the allowed brightness range remains constant for all input brightness levels, but the number of pulses sent to the stepping motor 26 is varied in accordance with the input brightness levels.

FIG. 34 is a table showing the relationship between the change in the brightness signal value Δy and the rotation angle θ of the stepping motor 26, according to a sixth embodiment of the present invention. As shown in FIG. 34, the brightness levels are arranged into 3 groups, with the change in brightness level Δy per degree of rotation of the light shield 25, decreasing as the brightness level y increases. In the sixth embodiment, the stepping motor 26 is rotated by 0.5° when one drive pulse is applied.

Figure 35:
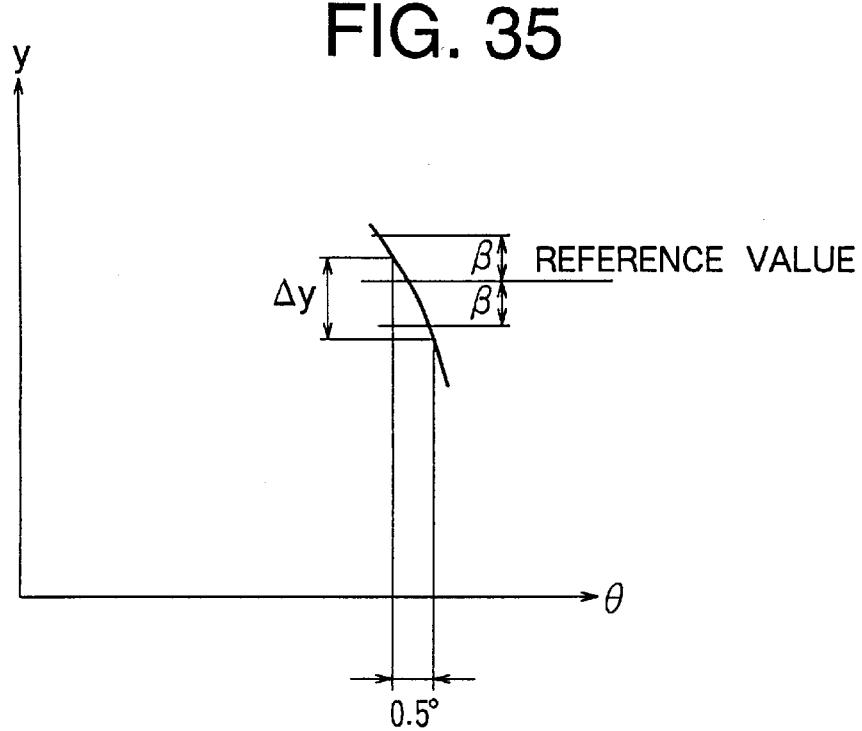
FIG. 35 shows another enlarged portion of the graph shown in FIG. 25.

FIG. 35 shows a partially enlarged view of the graph of FIG. 25. As shown in FIG. 35, in order to adjust the light shield 25 such that hunting does not occur, the change in brightness signal value Δy per change in rotation of stepping motor 26 during an interrupt (i.e., 0.5°) must be less than the allowed brightness range (i.e., 2β).

The sixth embodiment operates using the main program shown in FIG. 8, and the interrupt routine shown in FIG. 26.

Figure 36:
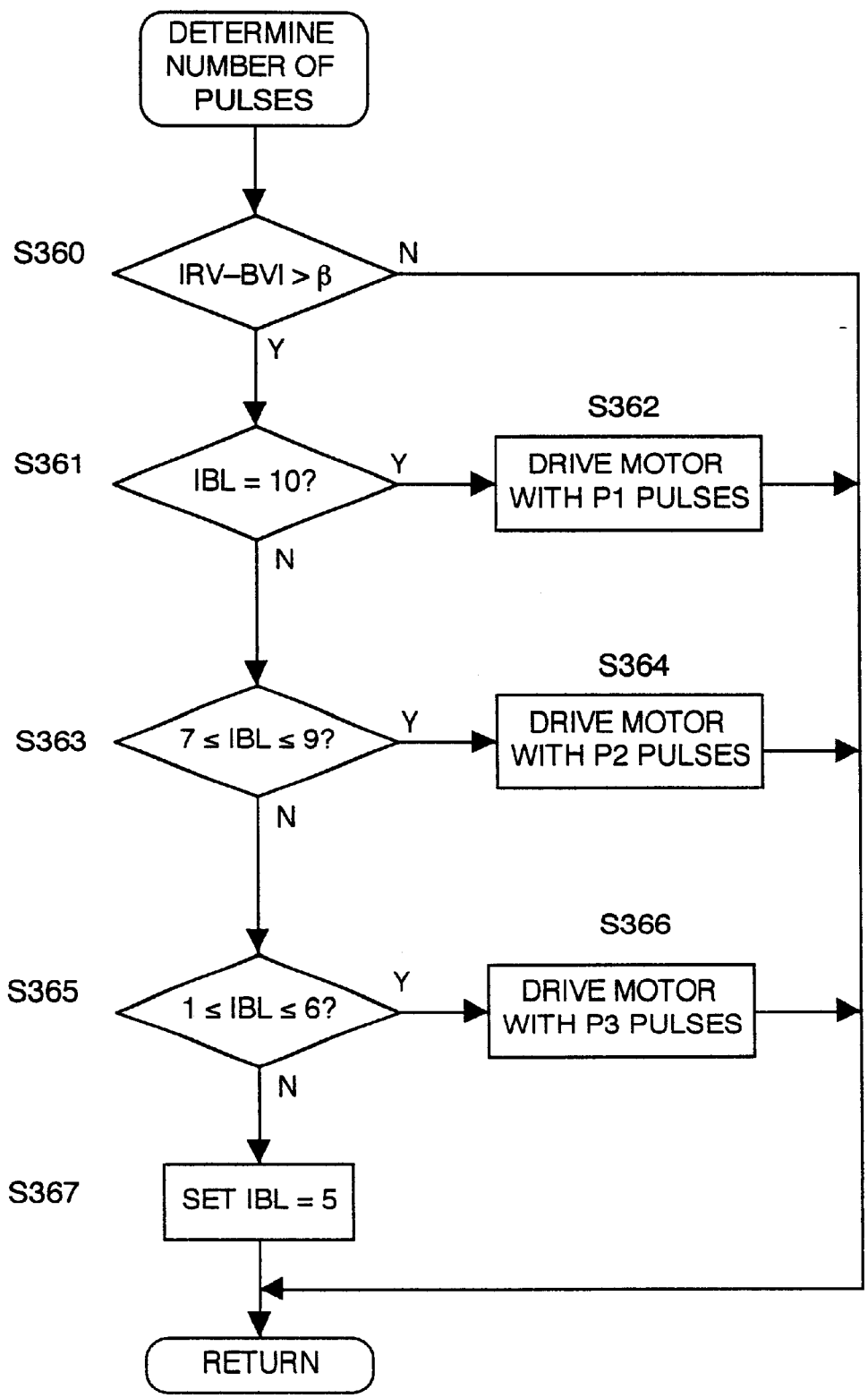
FIG. 36 shows a flowchart of a process for determining a number of pulses to send to the stepping motor, according to a sixth embodiment of the present invention.

FIG. 36 shows the subroutine according to the sixth embodiment, called in step S265 of the interrupt routine, shown in FIG. 26. In the sixth embodiment, the allowed brightness range, 2β is set equal to 6.

Step S360 determines whether the brightness value is within the allowed brightness range (i.e., |RV−BV|>β). If the brightness value is within the allowed brightness range (S360:N), then the subroutine is ended, and the interrupt routine is ended. Otherwise (S360:Y), if the input brightness level IBL is equal to 10 in step S361, then the stepping motor 26 is driven with P1 pulses, in step S362, and the subroutine is ended. In the sixth embodiment, P1=3.

If the input brightness level IBL is not equal to 10 (S361:N) but one of 9, 8 or 7, in step S363, then the stepping motor 26 is driven with P2 pulses, in step S364, and the subroutine is ended. In the sixth embodiment, P2=2. If the input brightness level IBL is less than or equal to 6 (S363:N), in step S365, then the stepping motor 26 is driven with P3 pulses, in step S366, and the subroutine is ended. In the sixth embodiment, P3=1.

If the brightness level is not sets or is erroneously set to a value outside the range 1 through 10, then the input brightness level IBL is set to 5 in step S367, and the routine ends.

As described above, the stepping motor 26 is driven with a higher number of pulses when the input brightness level IBL is high than when the input brightness level IBL is low. Therefore, the control of the rotation of the light shield 25 can be optimized depending on the desired input brightness level IBL.

FIG. 37 is a table showing the relationship between the change in the brightness signal value Δy and the rotation angle θ of the stepping motor 26, according to a modified control of the sixth embodiment. As shown in FIG. 37, the change in brightness level Δy per degree of rotation of the light shield 25 increases as the angle of rotation θ of the stepping motor 26 increases. In the modified sixth embodiment, the stepping motor 26 is rotated by 0.5° when one drive pulse is applied. Further, the number of pulses to be applied to the stepping motor 26 changes in accordance with the angle of rotation θ of the stepping motor 26.

Figure 38:
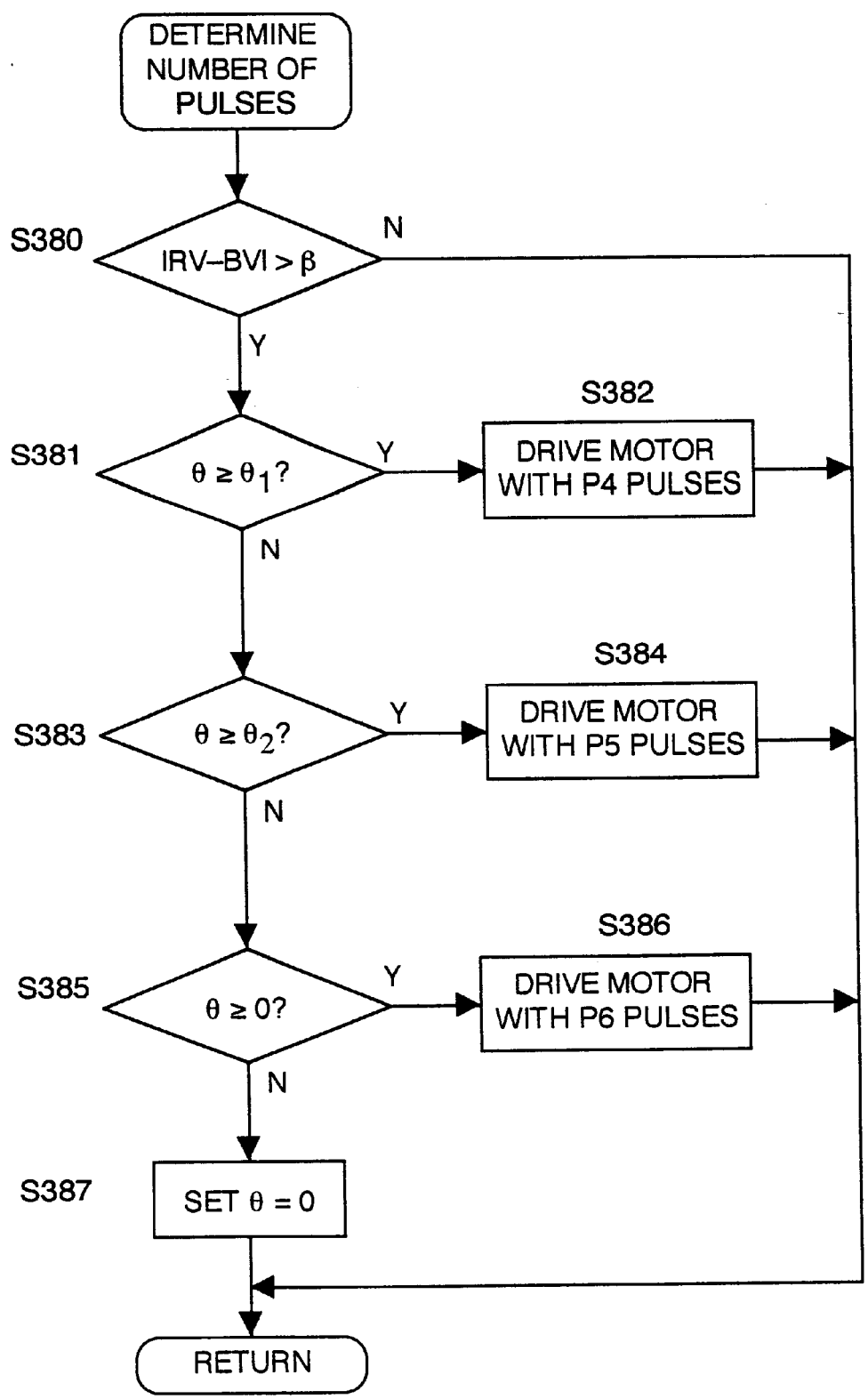
FIG. 38 shows a flowchart of a process for determining a number of pulses to send to the stepping motor, according to a first modification of the sixth embodiment of the present invention.

FIG. 38 shows the subroutine according to the modified control of the sixth embodiment, called in step S265 of the interrupt routine, shown in FIG. 26.

Step S380 determines whether the brightness value is within the allowed brightness range (i.e., |RV−BV|>β). If the brightness value is within the allowed brightness range (S380:N), then the subroutine is ended, and the interrupt routine is terminated. Otherwise (S380:Y), if the angle of rotation θ is greater than $\theta_1$, in step S381, then the stepping motor 26 is driven with P4 pulses, in step S382, and the subroutine is ended. In this embodiment, P4=1, and $\theta_1$=23°.

If the angle of rotation θ is less than $\theta_1$ (S381:N), but greater than $\theta_2$ in step S383, then the stepping motor 26 is driven with P5 pulses, in step S384, and the subroutine is ended. In this embodiment, P5=2, and $\theta_2$=16°.

If the angle of rotation θ is less than $\theta_2$ (S383:N), but greater than 0° in step S385, then the stepping motor 26 is driven with P6 pulses, in step S386, and the subroutine is ended. In this embodiment, P6=3.

If the angle of rotation θ is not set, or is erroneously set to a value outside the range, then the angle of rotation θ is set equal to 0° in step S387, and the routine ends.

As described above, the stepping motor 26 is driven with a higher number of pulses when the angle of rotation θ is low, than when the angle of rotation θ is high. Therefore, the control of the rotation of the light shield 25 can be optimized depending on the desired angle of rotation θ.

FIG. 39 shows a table of the relationship between the change in the brightness signal value Δy and the rotation angle θ of the stepping motor 26, for each of the endoscopes A, B and C, according to a second modified control of the sixth embodiment. As shown in FIG. 39, the change in brightness level Δy per degree of rotation of the light shield 25 increases as the angle of rotation θ of the stepping motor 26 increases. In this modified embodiment, the stepping motor 26 is rotated by 0.50° when one drive pulse is applied. Further, the number of pulses to be applied to the stepping motor 26 changes in accordance with the angle of rotation θ of the stepping motor 26.

Figure 40:
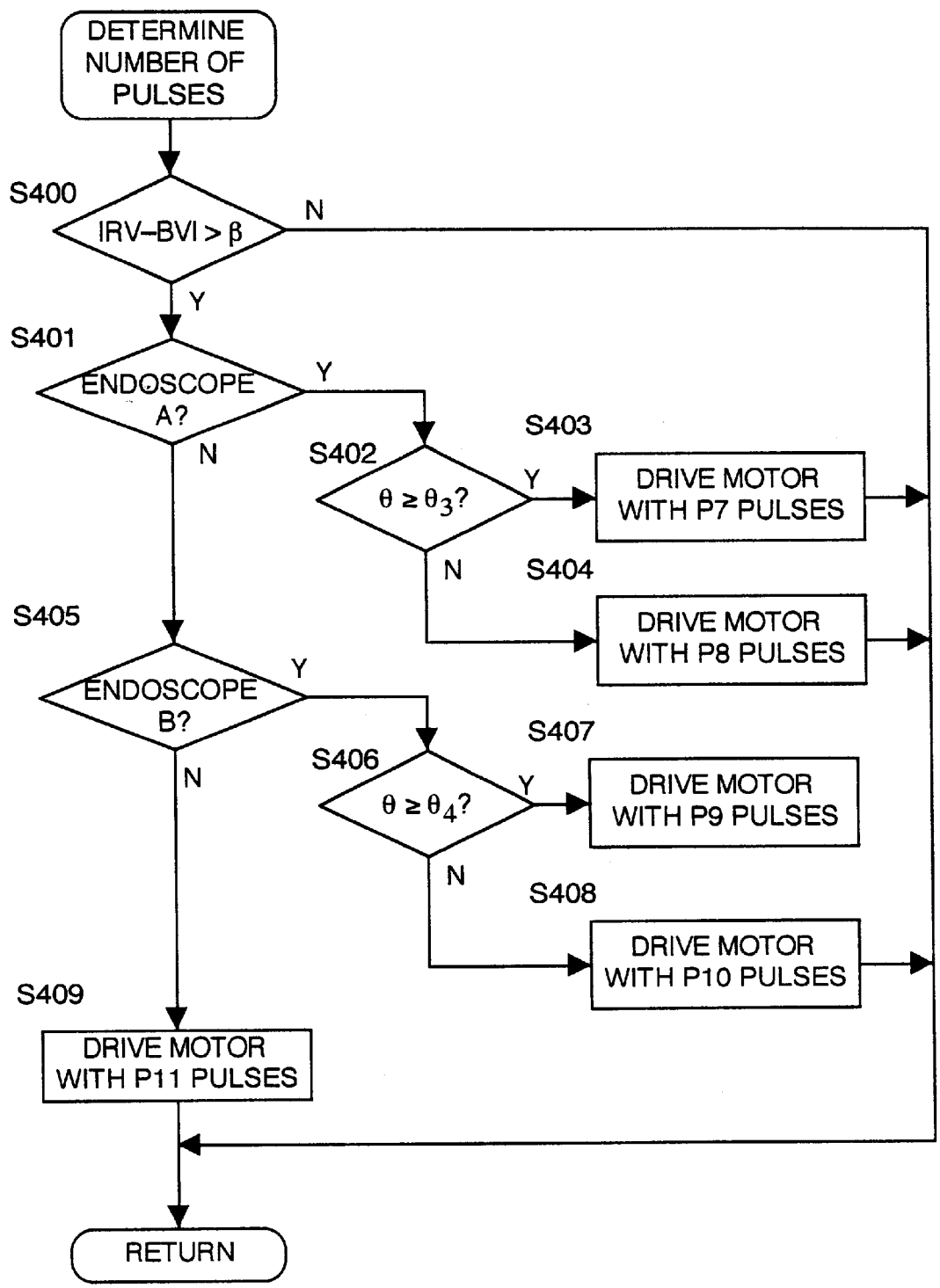
FIG. 40 shows a flowchart of a process for determining a number of pulses to send to the stepping motor, according to the second modification of the sixth embodiment of the present invention.

FIG. 40 shows a flowchart of the subroutine according to the second modified control of the sixth embodiment, called in step S265 of the interrupt routine, shown in FIG. 26.

Step S400 determines whether the brightness value is within the allowed brightness range (i.e., |RV−BV|>β). If the brightness value is within the allowed brightness range (S400:N), then the subroutine is ended, and the interrupt routine is ended. Otherwise (S400:Y), step S401 determines whether a type A endoscope is connected to the video processor 20. If a type A endoscope is connected (S401:Y) and the angle of rotation θ is greater than $\theta_3$, in step S402, then the stepping motor 26 is driven with P7 pulses, in step S403, and the subroutine is ended. In this embodiment, P7=1, and $\theta_3$=23°.

If the angle of rotation θ is less than $\theta_3$ (S401:N), then the stepping motor 26 is driven with P8 pulses, in step S404, and the subroutine is ended. In this embodiment, P8=2.

If a type A endoscope is not connected to the video processor 20 (S401:N), then step S405 determines whether a type B endoscope is connected. If a type B endoscope is connected (S405:Y) and the angle of rotation θ is greater than $\theta_4$, in step S406, then the stepping motor 26 is driven with P9 pulses, in step S407, and the subroutine is ended. In this embodiment, P9=2, and $\theta_3$=20°.

If the angle of rotation θ is less than $\theta_4$ (S406:2), then the stepping motor 26 is driven with P10 pulses, in step S408, and the subroutine is ended. In this embodiment, P10=3.

However, if a type C endoscope is connected, then the stepping motor 26 is driven with P11 pulses, in step S409, for all angles of rotation θ. In this embodiment, P11=4.

Thus, as described above, the number of pulses to be sent to the motor is determined in accordance with the type of endoscope and the angle of rotation of the light shield 25.

In the six embodiments described above, the light shield 25 is rotated by the stepping motor 26 in order to vary the amount of light emitted by the lighting unit. Then, the brightness value BV of the received brightness signal is detected, and a determination is made as to whether the light shield 25 should be adjusted. Therefore, the interval at which the interrupt may be executed is limited by the mechanical construction and stability of the light amount controlling device.

The seventh embodiment described below employs an electronic feedback control of the light amount controlling device. Therefore, the interval between successive interrupts can be shortened, and thus the light amount controlling device can be adjusted more quickly.

Electronically Controlled Embodiment

Figure 41:
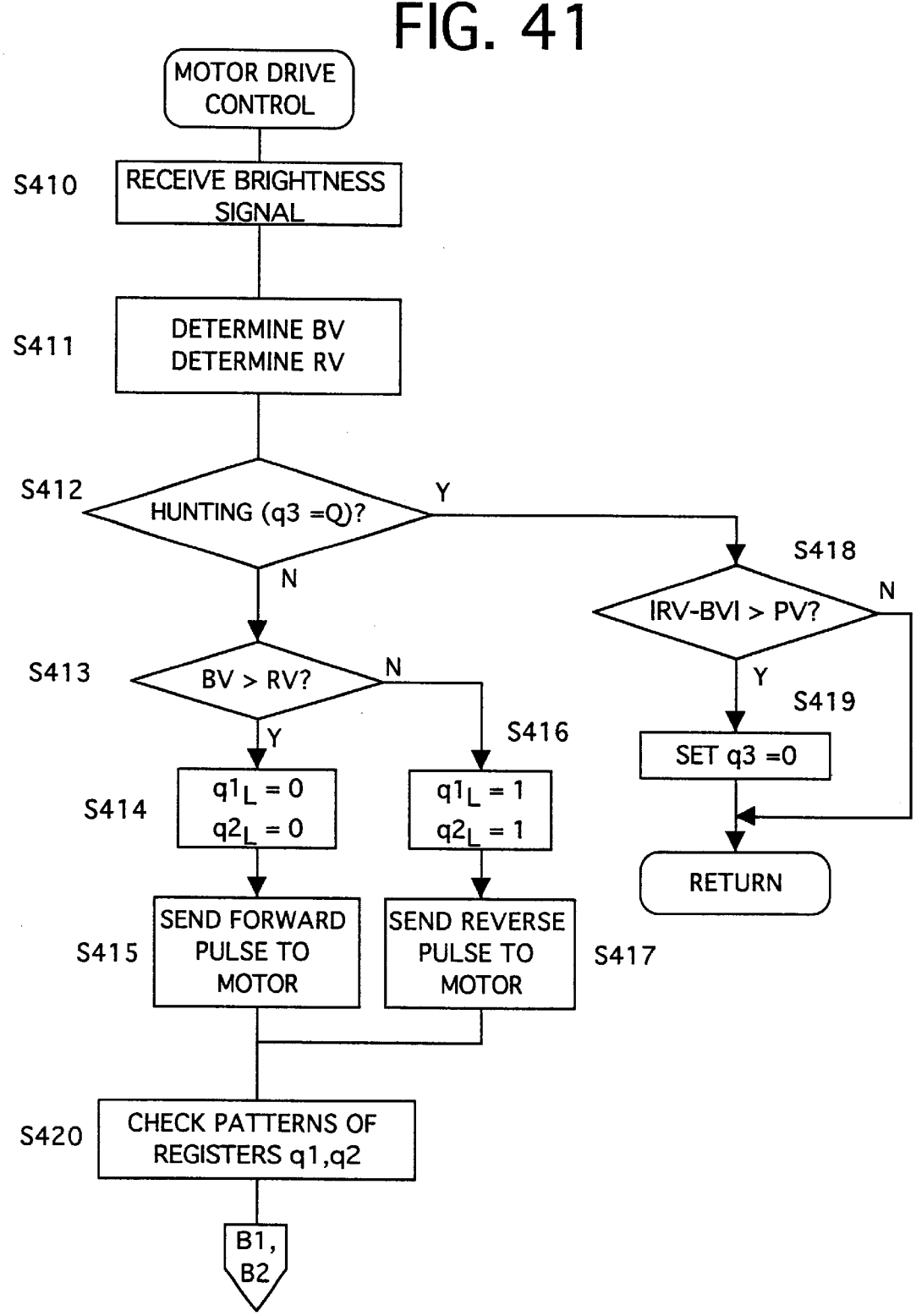
FIGS. 41 and 42 show a flowchart of an interrupt procedure used to control a driving of the stepping motor of the light amount controlling device, according to a seventh embodiment of the present invention.
Figure 42:
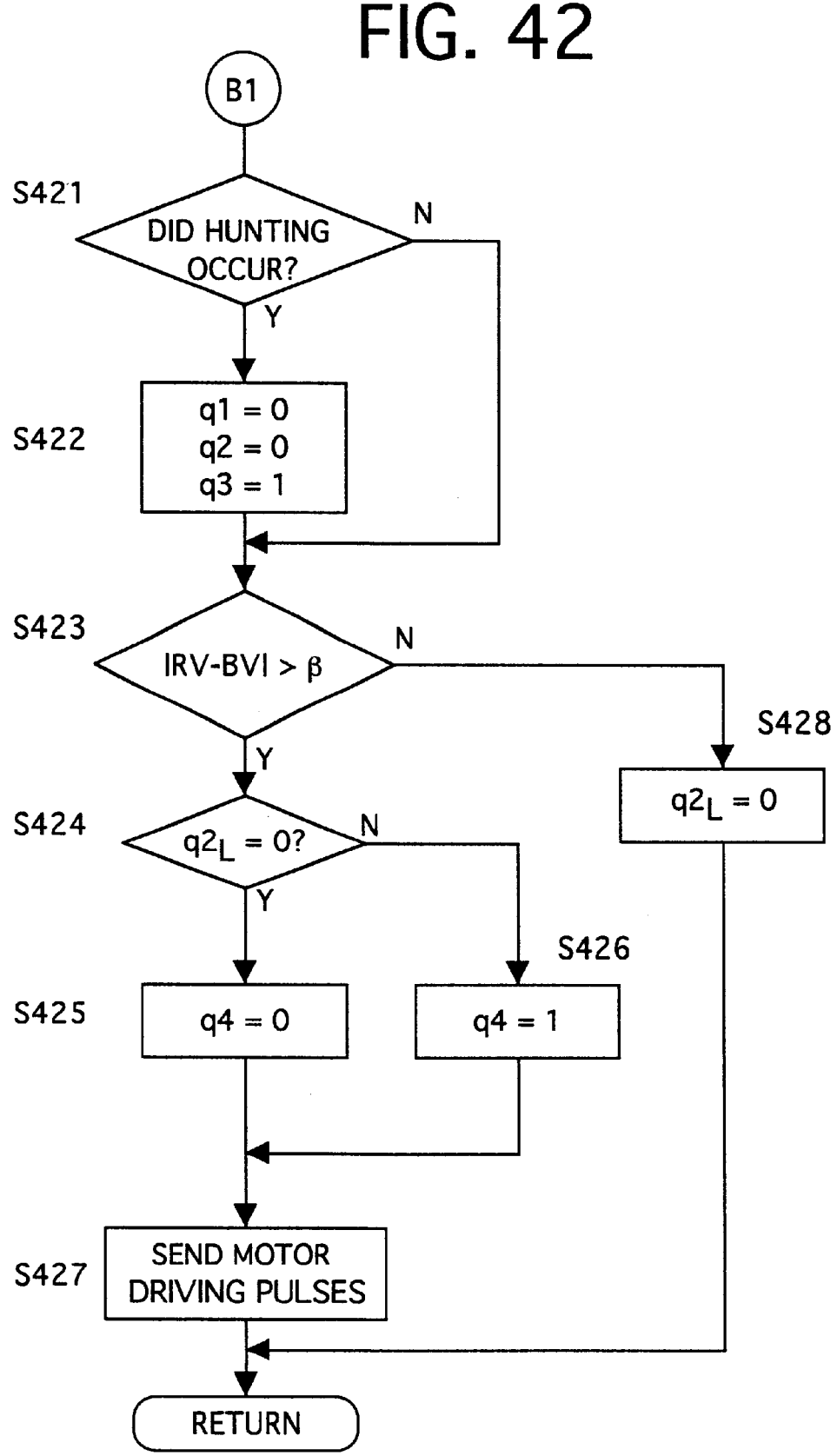

FIGS. 41 and 42 are flowcharts illustrating the drive control of the stepping motor 26, according to the seventh embodiment. The drive control of the stepping motor 26 is an interrupt procedure executed at a predetermined interval. In the seventh embodiment, the predetermined interval is 20 ms. The number of pulses applied to the stepping motor 26 is either one or two.

In the seventh embodiment, four storage registers q1 through q4 are used. As shown in FIG. 43, the register q1 is an eight-bit shift register with the least significant bit (i.e., $q1_L$) indicating whether the brightness value BV of the received image signal is greater than the reference value RV. If the brightness value BV is greater than the reference value RV, then $q1_L$ is set equal to 1, otherwise $q1_L$ is set equal to 0.

When the subsequent interrupt procedure is executed, the value in the $q1_L$ is shifted to the next highest order bit (i.e., shifted to the left). The received brightness value BV and the reference value RV are then compared as described above and $q1_L$ is set with the appropriate value. Thus, the register q1 stores the result of the comparison of the brightness value BV and the reference value RV, for eight consecutive interrupts. Further, the data of the most significant bit of the variable will be lost when the register is shifted to the left.

The register q2 is also an eight-bit register with the least significant bit $q2_L$ indicating whether the stepping motor 26 has been rotated in a forward or reverse direction during the currently executed interrupt procedure. If the stepping motor 26 is rotated in the forward direction, then $q2_L$ is set to 0, otherwise $q2^L$ is set to 1. When the stepping motor 26 is not driven, $q2_L$ is set to 0.

When the subsequent interrupt procedure is executed, the value in the $q2_L$ is shifted to the next highest order bit (i.e., shifted to the left). Thus, the register q2 stores the value indicating the direction of rotation of the stepping motor 26, for eight consecutive interrupts. Further, the data of the most significant bit of the variable will be lost when the register is shifted to the left.

The register q3 is a one-bit register variable representing whether the light shield 25 is in a hunting condition. The register q3 is set to 0 if the light shield 25 is being normally driven. If the light shield 25 is in a hunting condition, then the register q3 is set to 1.

The register q4 is used to indicate the direction of rotation of the stepping motor 26 during the last interrupt procedure. If the stepping motor 26 was driven in the forward direction, then q4 will be set to 0, otherwise (i.e., for the reverse direction) q4 is set to 1.

As shown in FIGS. 41 and 42, the brightness signal is received, in step S410. In step S411, the brightness value BV and reference value RV are determined. Step S412 then checks the value of the register q3 to determine whether hunting is occurring.

If q3 is equal to Q, then hunting is occurring. In this embodiment Q is equal to 1. If hunting is occurring (i.e., q3=1, S412:Y), step S418 determines whether the absolute value of the difference between the reference value RV and the brightness value BV is greater than a predetermined value PV (e.g., 8). If |RV−BV|>PV, then q3 is set to 0, in step S419, and the interrupt procedure is terminated. Otherwise (S418:N), the interruption procedure is terminated. Therefore, the light shield 25 is not driven during the current interrupt, however, by setting q3 equal to 0, it is possible to drive the light shield 25 during the next interrupt, even if hunting is currently occurring.

If hunting is not occurring (i.e., q3=0, S412:N), step S413 determines whether the brightness value BV is greater than the reference value RV. If the brightness value BV is greater than the reference value RV (S413:Y), then $q1_L$ and $q2_L$ are set to 0, in step S414, and the forward rotation instruction signal is sent to the stepping motor 26, in step S415. However, if the brightness value BV is not greater than the reference value RV (S413:N), then $q1_L$ and $q2_L$ are set to 1, in step S416, and the reverse rotation instruction signal is sent to the stepping motor 26, in step S417. The forward or reverse instruction signals are signals for determining the rotation direction of the stepping motor 26. The stepping motor 26 is not rotated in steps S415 or S417, but is rotated when it receives a motor driving pulse.

Continuing in FIG. 42, in step S420 each bit of the registers q1 and q2 is checked. If at least one of the registers q1 or q2 has the bits of its register alternating between "1" or "0", then step S421 determines that hunting is occurring. Further, this decision may be made by checking only one of the registers q1 or q2.

If it is determined that hunting is not occurring, control proceeds to step S423, otherwise all of the bits of the registers q1 and q2 are set at 0, and the register q3 is set to 1, in step S422.

Step S423 determines whether the brightness value BV is in the allowed brightness range (i.e., |RV−BV|>β, β having a value of 3 for example), where RV±β is the allowed brightness range. If |RV−BV|>β (S423:N), then step S428 sets $q2_L$ equal to 0, and the routine is ended. Otherwise (S423:Y), step S424 determines whether $q2_L$ is equal to 0. If $q2_L$ is equal to 0 (S424:Y), then q4 is set equal to 0, in step S425. Otherwise (S424:N), q4 is set equal to 1, in step S426.

Then in step S427 a driving pulse is sent to the stepping motor 26, and the routine ends.

As described above, in the seventh embodiment, by examining the registers q1 and/or q2, the occurrence of hunting can be determined. Therefore, since the examination of the registers q1, q2 is performed electronically, the determination as to whether hunting is occurring can be made quickly.

Further, as described above, when hunting is occurring, no pulses are sent to the stepping motor 26, and thus the stepping motor 26 is not normally driven. However, if the difference in brightness (|BV−RV|) is greater than the predetermined value PV, the value of q3 is set to 0, and the stepping motor 26 can be driven during the next interrupt procedure. This reduces the amount of time required to rotate the light shield 25.

Figure 44:
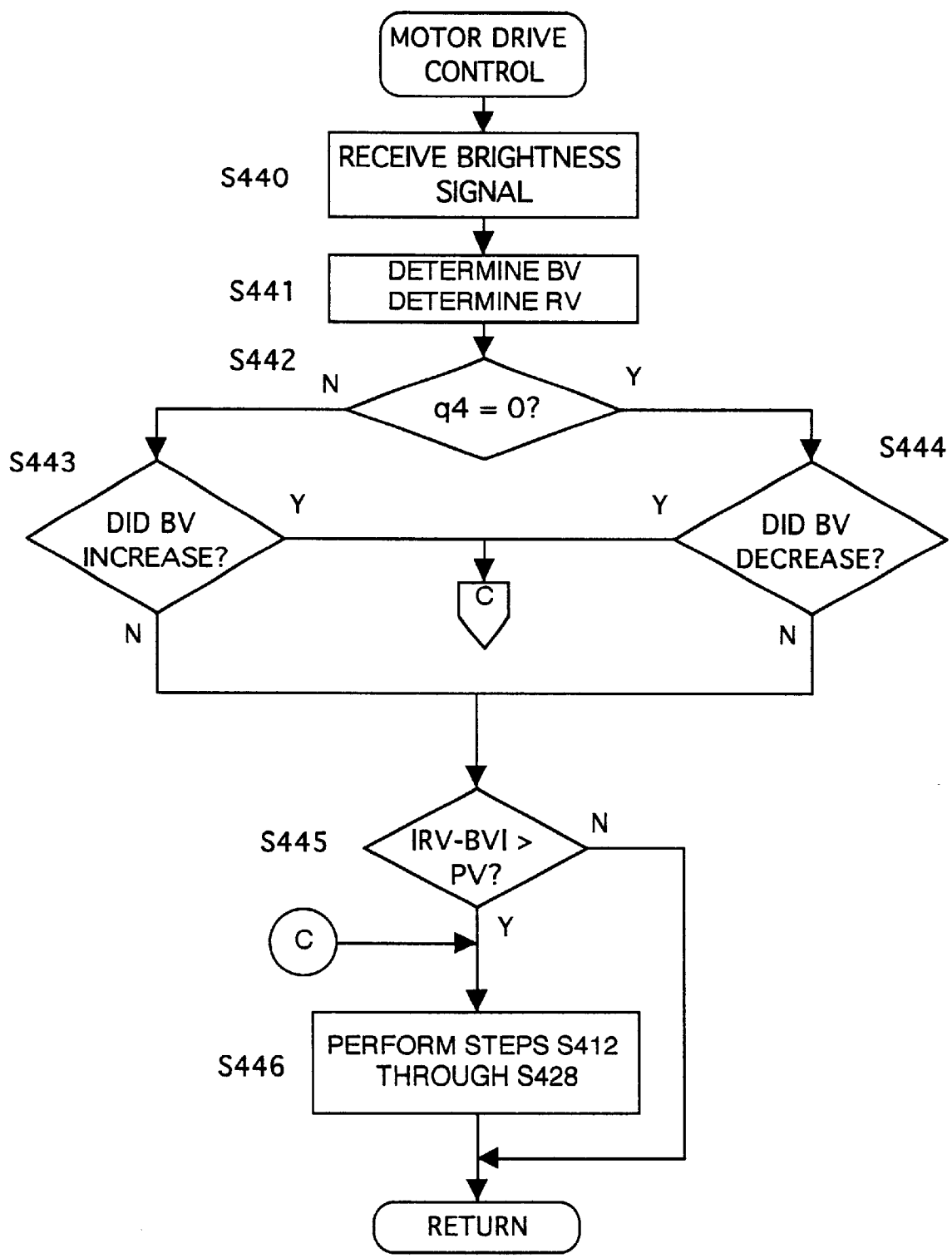
FIG. 44 shows a flowchart of an interrupt procedure used to control a driving of the stepping motor of the light amount controlling device, according to a modification of the seventh embodiment of the present invention.

FIG. 44 shows a flowchart of the drive control procedure of the stepping motor 26 according to a modification of the seventh embodiment of the present invention. The modified seventh embodiment is similar to the seventh embodiment described above, except that the processing steps S440 through S446 are performed before the interrupt procedure shown in FIGS. 41 and 42 is executed.

Step S440 receives the image signal from the image processing circuit 21. Then step 441 determines the brightness value BV of the image signal and the reference value RV. Step S442 determines whether the value of the register q4 is equal to 0. If q4 is equal to 0, then the motor was rotated in the forward direction, and control proceeds to step S444, which determines whether the brightness value BV has decreased. If the brightness value BV has decreased (S444:Y), then control proceeds to step S446. Otherwise (S444:N), control proceeds to step S445 which determines whether the difference between the brightness value BV and the reference value RV is greater than the predetermined value PV. If |RV−PV|>BV (S445:Y), then control proceeds to step S446. Otherwise (S445:N), the routine is terminated.

In the case that q4 is not equal to 0 (S442:N), step S443 determines whether the brightness value BV has increased.

If the brightness value BV has increased (S443:Y), then control proceeds to step S446. Otherwise (S443:N), step S445 determines whether the difference between the brightness value BV and the reference value RV is greater than the predetermined value PV (PV being 10, for example). If |RV−BV|>PV (S445:Y), then control proceeds to step S446. Otherwise (S445:N), the routine is terminated.

At step S446, steps S412 through S424 of the flowchart of FIGS. 41 and 42, are performed.

According to the modification of the seventh embodiment, when the brightness value BV does not change after the stepping motor 26 has rotated the light shield 25 (e.g. as a result of mechanical delay in rotating the light shield 25), if the difference between the brightness value BV and the reference value RV is greater than the predetermined value PV, the motor drive signal is sent to the driving circuit 28. This reduces the amount of time required to locate the light shield 25, in the cases that the difference in brightness (|BV−RV|) is greater If the difference (|BV−RV|) is not greater than the predetermined value PV, the motor drive signal is not sent to the driving circuit 28.

In the modified seventh embodiment, the register q4 is employed to easily determine the direction that the motor was driven during the previous interrupt. However, by examining $q2_L$ in step S442, the same result can be achieved.

Figure 45:
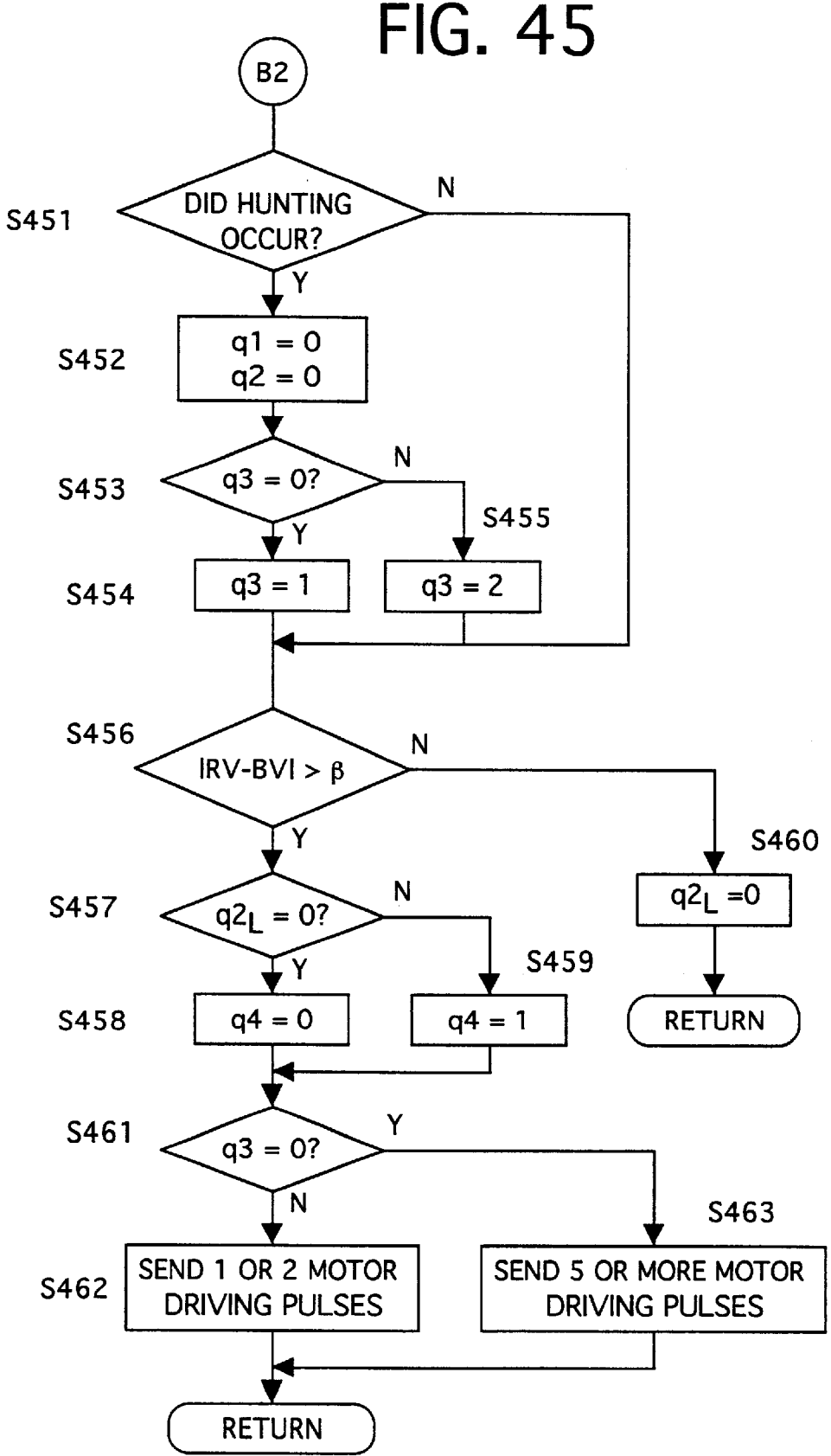
FIG. 45 shows a flowchart of a process for determining a number of pulses to send to the stepping motor, according to an eighth embodiment of the present invention.

FIGS. 41 and 45 show a flowchart of a drive control procedure of the stepping motor 26, according to an eighth embodiment of the present invention. The eighth embodiment is similar to the seventh embodiment described above. However, in the eighth embodiment, the interval between successive interrupts is 50 ms. Further, the register q3 is a two bit register. If the light shield 25 is driven normally, q3 has the value 0. If hunting occurs, and the number of motor drive pulses is high (i.e., 5 through 10), then q3 is set equal to 1. If hunting occurs, and the number of motor drive pulses is low (i.e., 1 or 2), then q3 is set equal to 2.

Therefore, in the eighth embodiment the value of Q is 2, and step S412 determines whether q3 is equal to 2. Further, the interval between successive interrupts is 50 ms. Still further, the number of pulses applied to the motor during an interrupt can be made small or large.

In the eighth embodiment, after the patterns of the registers q1 and q2 have been checked in step S420, if one of the registers q1, $q2^L$ has an alternating pattern of "1"s and "0"s, then step S451 determines that hunting is occurring. If hunting is occurring (S451:Y), q1 and q2 are set to 0 in step S452. Step S453 checks whether q3 is set equal to 0. If q3 is set to 0 (S453:Y), then q3 is set equal to 1 in step S454. Otherwise (S453:N), q3 is set equal to 2 in step S455, and control proceeds to step S456. If hunting is not occurring (S451:N), then control proceeds to step S456.

Step S456 determines whether |RV−BV|>β, where RV±β, where RV±β is the allowed brightness range. If the difference is within the allowed brightness range (S456:N), then $q2_L$ is set equal to 0 in step S460, and the routine is terminated.

If the difference is not within the allowed brightness range (S456:Y), then step S457 determines whether $q2_L$ is equal to 0. If $q2_L$ is equal to 0 (S457:Y), then q4 is set equal to 0, in step S458. Otherwise (S458:N), q4 is set equal to 1, in step S459.

Step S461 determines whether q3 is equal to 0. If q3 is equal to 0 (S461:Y), then 5 or more driving pulses are sent to the stepping motor 26 in step S463, and the routine is terminated. Otherwise (S461:N), only one or two driving pulses are sent to the stepping motor 26 in step S462, and the routine is terminated.

As described above, in the eighth embodiment, if the number of drive pulses sent to the stepping motor 26 is large, and hunting is occurring, then in the next interrupt procedure the number of drive pulses is made smaller and the driving of the stepping motor 26 is continued. However, if the number of drive pulses sent to the stepping motor 26 is small, and hunting is still occurring, then no drive pulses are sent to the stepping motor 26.

Thus, with this control, the stepping motor 26 is initially driven with a large number of driving pulses in order to quickly rotate the light shield 25. Then, if hunting occurs, the number of drive pulses is reduced, and the motor driving is continued. Therefore, the light shield 25 can be rotated with high speed and accuracy.

Figure 46B:
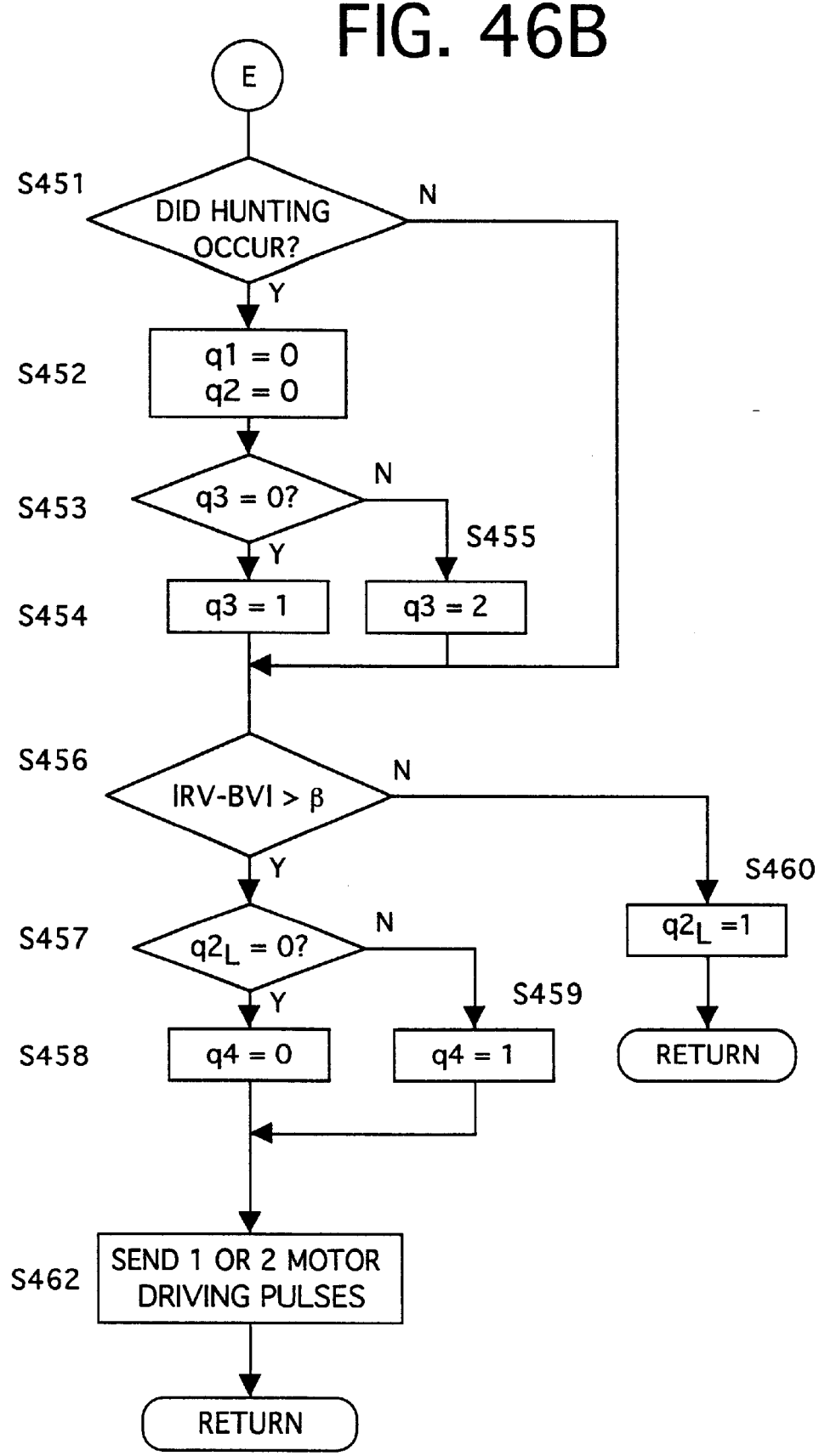

FIGS. 46A and 46B show a flowchart of the drive control procedure of the stepping motor 26 according to a modification of the eighth embodiment of the present invention. The modified eighth embodiment is similar to the modified seventh embodiment shown in FIG. 44, and described above.

As shown in FIG. 46A, the same steps S440 through S445, shown in FIG. 44, are executed. However, in step S443, if BV increased (S443:Y) then control proceeds to step S447. In step S447 the steps S412 through S420 and S451 through S462, shown in FIGS. 41 and 45 are executed. Similarly, in step S444, if BV decreases, control also goes to step S447. After step S447 is executed the interrupt procedure is terminated. Further, in step S445, if |RV−BV|>PV, then step S447 is executed. Otherwise (S445:N), control proceeds to step S448, where steps S412 through S420 are performed. Then steps S451 through S462 as shown in FIG. 46B are executed. These steps are similar to the steps shown in FIG. 45. However, in the modified eighth embodiment, after q4 has been set to 0 in step S458 or q4 has been set to 1 in step S459, step S462 is executed.

Therefore in the modified eighth embodiment, when the brightness value BV does not change after the stepping motor 26 has rotated the light shield 25 (e.g. as a result of mechanical delay in rotating the light shield 25), if |RV−BV| is greater than the PV, a relatively large number of motor driving pulses is sent to the driving circuit 28. However, if |BV−RV| is not greater than PV, but is greater than β, a relatively small number of motor driving pulses is sent to the driving circuit 28. In this case, the value of q3 has no effect on the number of driving pulses sent to the motor.

In the eighth embodiments described above, a single light shield 25 was employed in order to vary the amount of light emitted by the lighting unit. In the ninth embodiment described below, two light shields are employed.

Two Light Shield Embodiment

Figure 47:
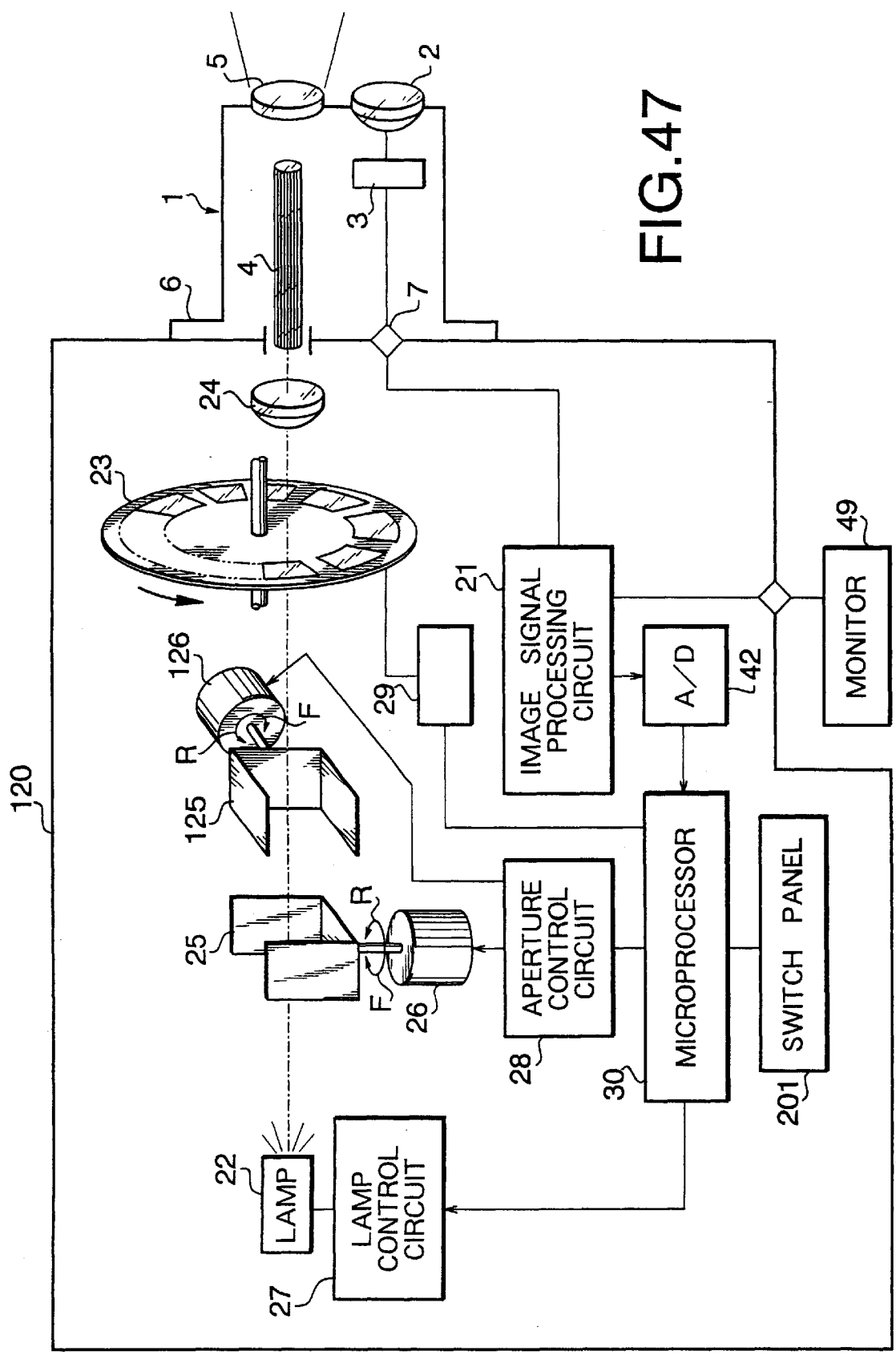
FIG. 47 shows a schematic diagram of an endoscope and video processor which employ a light amount controlling device of the present invention, according to a ninth embodiment of the present invention.

FIG. 47 shows a schematic diagram of the construction of the endoscope according to the ninth embodiment of the present invention. The construction of ninth embodiment is similar to the construction of the first embodiment shown in FIG. 1, with the common elements having the same reference numbers.

As shown in FIG. 47, the video processor 120 has the light shield 25 arranged to be rotated by the stepping motor 26 along a vertical axis, in a similar manner to the first embodiment. The video processor 120 also includes a light shield 125 arranged to be rotated by a stepping motor 126 along a horizontal axis. The light shield 125 is positioned between the lamp 22 and the light shield 125. The motor control circuit 28 controls the operation of the stepping motor 25 and the stepping motor 125. Information related to an operation of the endoscope 1 is input using the switch panel 201.

Figure 48:
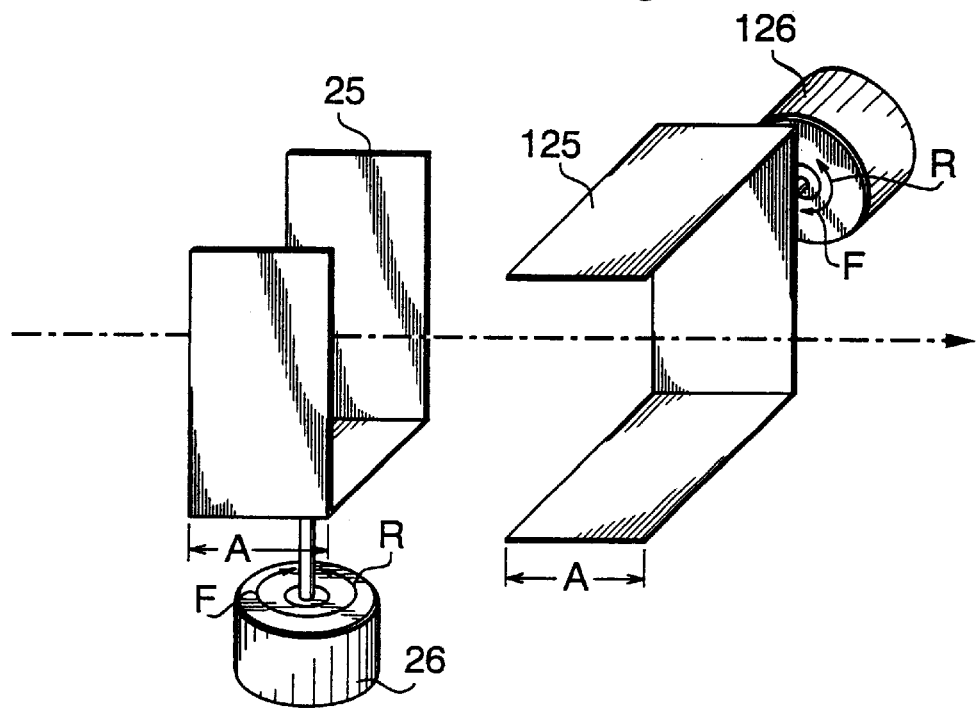
FIG. 48 is a perspective view of light shields used in the light amount controlling device shown in FIG. 47.

FIG. 48 shows a perspective view of the light shields 25 and 125. The light shields 25, 125 have a U-shape, and are rotated about the vertical and horizontal axes, respectively, by the stepping motors 26 and 126. Further, the light shields 25, 125 have the same size.

The light shield 25 varies the size of the light path L in the horizontal direction, while the light shield 125 varies the size of the light path L in the vertical direction. Thus, the amount of light which enters the optical fiber 4 can be controlled quickly and accurately.

The brightness level can be selected from amongst ten levels 1 through 10, using the switch panel 201. The selected brightness level is read by a microprocessor 130, and determines which of the light shields 25, 125 is to be rotated. Further, the direction of rotation and amount of rotation of the selected light shield is also determined by the microprocessor 130.

FIG. 49 is a block diagram illustrating the controller 130. As shown in FIG. 49, the microprocessor 130 includes an operation control circuit 131, a direction control circuit 132 and a motor selection circuit 133. The operation control circuit 131 receives a brightness value from the switch panel 201. Further, the integrated output of the CCD 3 is output from the integration circuit 109 to the operation control circuit 131. The operation control circuit 131 compares the brightness of the integrated CCD signal with a reference brightness level corresponding to the brightness level input from switch panel 201.

Based on the comparison of the two signals, the operation control circuit 131 controls the direction control circuit 132 to output a forward or reverse drive signal to the motor control circuit 28. Further, the operation control circuit 131 controls the motor selection circuit 133 to output a motor select signal to the motor control circuit 28. The motor control circuit 28 controls the operation of the motors 26 and 126 in accordance with the signals received from the direction control circuit 132 and the motor selection circuit 133.

The operation control circuit 131, the direction control circuit 132, and the motor selection circuit 133 may be implemented as discrete hardware units. Alternatively, the functions of these blocks may be implemented in software using a CPU, RAM, and a ROM etc.

Figure 50:
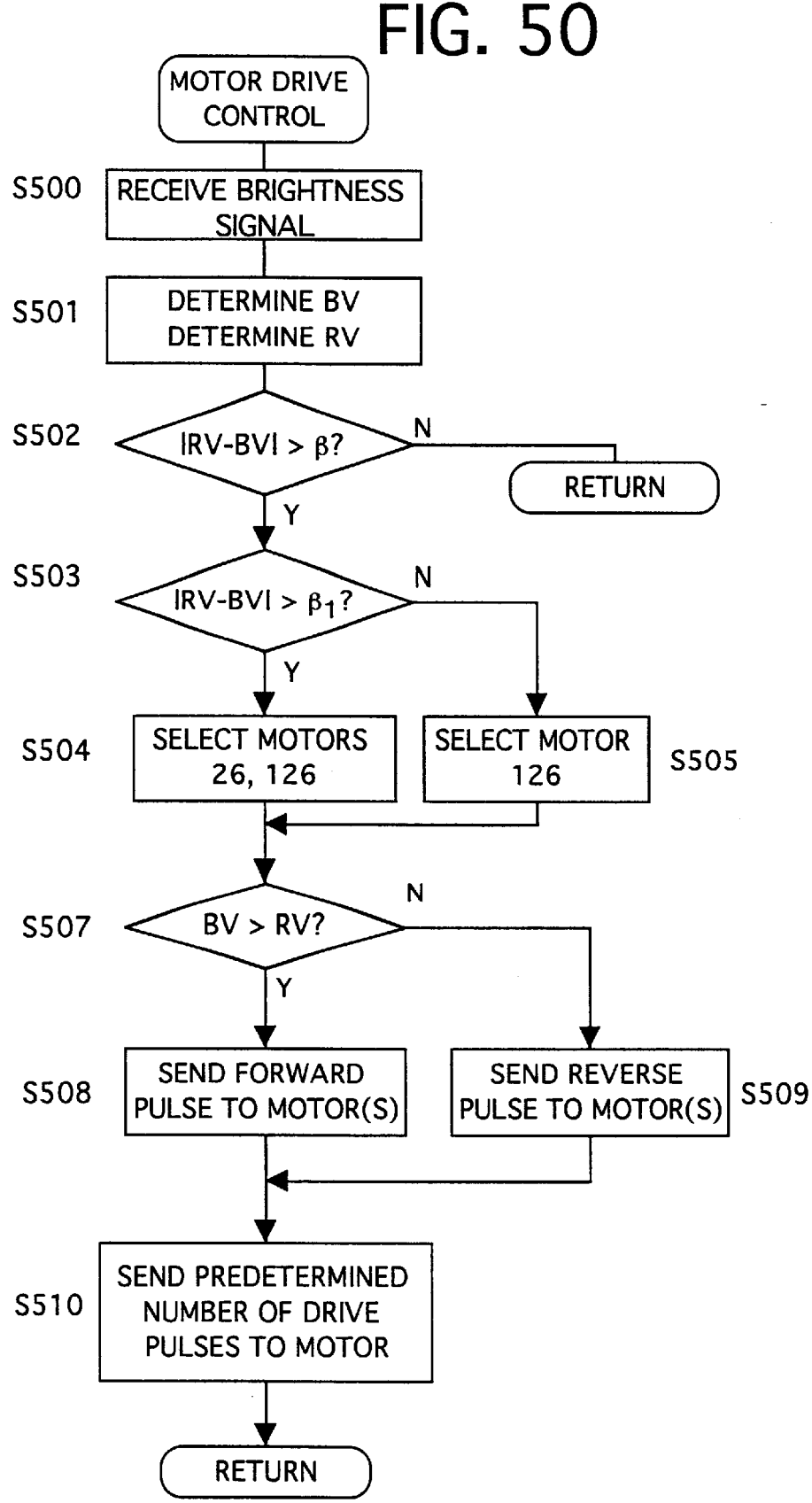
FIG. 50 shows a flowchart of an interrupt procedure used to control a driving of the stepping motor of the light amount controlling device, according to the ninth embodiment of the present invention.

FIG. 50 illustrates a flowchart of the drive control procedure of the stepping motors 26 and 126, according to the ninth embodiment. In this embodiment, the interrupt procedure is executed every 50 ms.

At step S500, the brightness signal is received from the CCD. Step S501 determines the brightness value BV and the reference value RV. Step S502 determines whether the difference between the received brightness value BV and the reference value RV is greater than an allowed brightness range $\beta$. If |RV−BV| is not greater than $\beta$(S502:N), then the routine is terminated. Otherwise (S502:Y), control proceeds to step S503 which determines whether |RV−BV| is greater than another allowed brightness range $\beta1$, where $\beta1$ is greater than $\beta$. If |RV−BV| is greater than $\beta1$ (S503:Y), then the motor selection circuit 133 selects both stepping motors 26, 126 to be driven by the motor control circuit 28, in step S504. Otherwise (S503:N), the motor selection circuit 133 selects only stepping motor 126, to be driven by the motor control circuit 28, in step S504.

After the motor to be driven has been selected, step S507 determines whether the brightness value BV is greater than the reference value RV. If the brightness value BV is greater than the reference value RV (S507:Y), then the forward pulse is sent to the stepping motor(s) 26, 126 in step S508. Otherwise (S507:N), the reverse pulse is sent to the stepping motor(s) 26, 126 in step S509. Then a predetermined number of pulses is sent to the stepping motor(s), in step S510, and the routine is ended.

As described above, if the difference between the brightness value and the reference value is larger than the allowed brightness range $\beta1$, then both stepping motors 26, 126 arc driven to adjust the amount of light emitted by the lighting unit. Therefore, the amount of light can be adjusted quickly and accurately. Further, by using two light shields 25, 125, the amount of light can be adjusted quickly, while at the same time the number of pulses sent to the stepping motors 26, 126 can be kept low. Thus, the hunting problem can be avoided.

Figure 51:
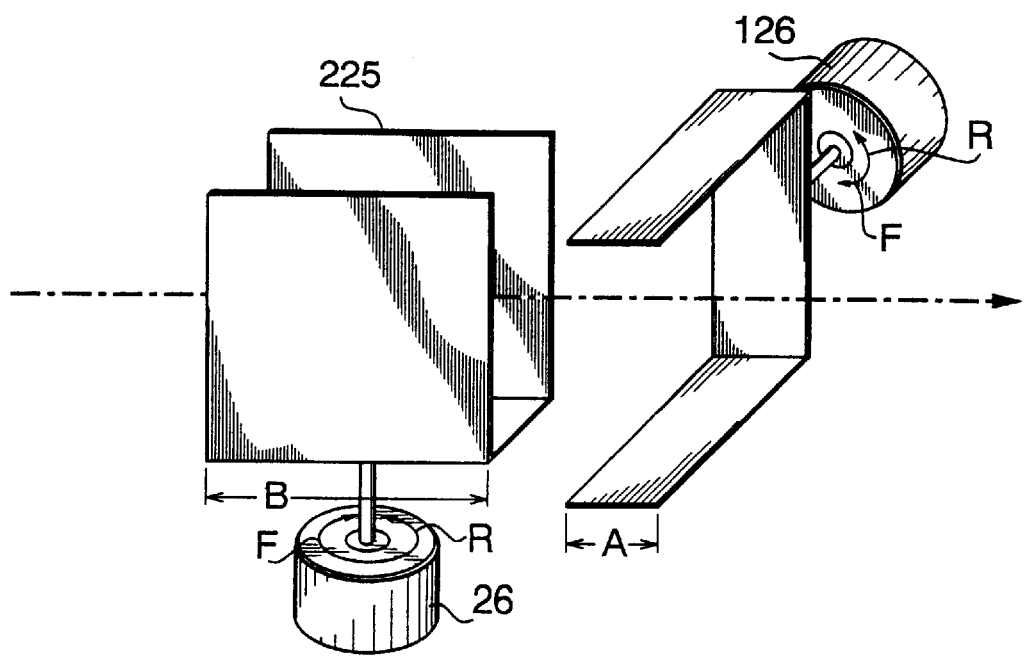
FIG. 51 is a perspective view of another set of light shields used in a modification of the ninth embodiment.

FIG. 51 shows a modification of the ninth embodiment. In this modification, the light shield 25a is designed such that the length of side B is longer than the length A of the corresponding side of the light shield 125. With this construction, when the light shield 25a is rotated, the change in the amount of light is greater than when the light shield 125 is rotated.

FIG. 52 illustrates a flowchart of the drive control procedure of the stepping motors 26 and 126, according to the modified ninth embodiment. This is similar to the flowchart shown in FIG. 50 with steps S500 through S510 being executed. However, at step S503, if |RV−BV|>$\beta1$, then step S506 is executed instead of step S504. In step S506, only the motor 26 is selected to be driven by the motor control circuit 28.

Thus, as described above, if the difference between the brightness value and the reference value is larger than the allowed brightness range $\beta1$, then the stepping motor 26 is driven to adjust the amount of light. Therefore, the amount of light can be adjusted quickly and accurately, since rotation of the light shield 25a has a greater effect on the change in the amount of light than the rotation of the light shield 125. Further, by using two light shields 25a, 125, each one having a different effect on the amount of light, the amount of light can be adjusted quickly, while at the same time entering that the number of pulses sent to the stepping motors 26, 126 can be kept low. Thus, the hunting problem can be avoided.

The present disclosure relates to subject matter contained in Japanese Patent Application Nos. HEI 6-185832 filed on Aug. 8, 1994; HEI 6-196362 filed on Aug. 22, 1994; HEI 6-196363 filed on Aug. 22, 1994; HEI 6-196364 filed on Aug. 22, 1994; HEI 6-196365 filed on Aug. 22, 1994; HEI 6-200682 filed on Aug. 25, 1994; and HEI 6-203164 filed on Aug. 29, 1994; which are expressly incorporated herein by reference in its entirety.

What is claimed is:

1. A device for controlling an amount of light of a lighting unit for use in an endoscope, said endoscope being used to view an image of an object, said device comprising:

a light shielding system that shields light generated by a light source and transmitted to said endoscope;

a stepping motor that drives said light shielding system to change an angular position of said light shielding system to change a light shielding amount;

a system that detects a brightness of said image during each of a plurality of predetermined time intervals;

an input system that inputs a desired brightness of said image;

a driving system that applies a predetermined number of driving pulses to said stepping motor during each of said plurality of predetermined time intervals if a difference between the detected brightness and the desired brightness exceeds a predetermined level; and a system that determines said predetermined number of pulses applied by said driving system in accordance with a variation of a predetermined parameter.

2. The device according to claim 1, said predetermined parameter comprising said desired brightness.

3. The device according to claim 1, said predetermined parameter comprising a rotation angle of said stepping motor.

4. The device according to claim 1, said predetermined parameter comprising a type of an endoscope used with said device.

5. The device according to claim 1 further comprising a system that determines an angular position of said light shielding system, said number of predetermined pulses applied by said driving system being determined in accordance with said determined angular position.

6. The device according to claims 1, further comprising a system for determining a type of the endoscope with which said device is used, said number of predetermined driving pulses applied by said driving system being determined in accordance with said determined endoscope type.

7. A device for controlling an amount of light of a lighting unit for an endoscope, comprising:

a light source;

a light guide that directs light emitted by said light source to the endoscope, the light guide having a light receiving surface;

a light shielding mechanism including a light shielding member positioned in a light path from said light source to said light receiving surface of said light guide;

a stepping motor that drives said light shielding member to change a light shielding amount;

a detecting system that detects a brightness of an observation frame of the endoscope at predetermined time intervals;

a brightness inputting system through which a desired brightness of the image can be input;

a pulse generating system that generates pulses during each of said predetermined time intervals, a number of said pulses generated being used to control a driving amount of said stepping motor during each of said plurality of predetermined time intervals; and a determining system that determines said number of pulses generated by said pulse generating system in accordance with variation in a predetermined parameter.

8. The device according to claim 7, said predetermined parameter comprising said desired brightness.

9. The device according to claim 7, said predetermined parameter comprising a rotation angle of said stepping motor.

10. The device according to claim 7, said predetermined parameter comprising a type of an endoscope used with said device.

11. The device according to claim 7, further comprising a system that controls said stepping motor to drive said light shielding mechanism in response to said detected brightness of said image being outside an allowed brightness range of said image.

* * * * *